US 9,505,750 B2

(12) United States Patent
Hubschwerlen et al.

(10) Patent No.: US 9,505,750 B2
(45) Date of Patent: Nov. 29, 2016

(54) 5-AMINOCYCLYLMETHYL-OXAZOLIDIN-2-ONE DERIVATIVES

(75) Inventors: Christian Hubschwerlen, Durmenach (FR); Georg Rueedi, Allschwil (CH); Jean-Philippe Surivet, Kembs (FR); Cornelia Zumbrunn Acklin, Basel (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 1240 days.

(21) Appl. No.: 12/809,555

(22) PCT Filed: Dec. 17, 2008

(86) PCT No.: PCT/IB2008/055374
§ 371 (c)(1),
(2), (4) Date: Jun. 18, 2010

(87) PCT Pub. No.: WO2009/077989
PCT Pub. Date: Jun. 25, 2009

(65) Prior Publication Data
US 2011/0003789 A1    Jan. 6, 2011

(30) Foreign Application Priority Data

Dec. 18, 2007  (WO) .................. PCT/IB2007/055194
Oct. 10, 2008  (WO) .................. PCT/IB2008/054170

(51) Int. Cl.
| A61K 31/422 | (2006.01) |
| C07D 413/14 | (2006.01) |
| C07D 487/04 | (2006.01) |
| C07D 471/04 | (2006.01) |
| C07D 417/14 | (2006.01) |

(52) U.S. Cl.
CPC ........... *C07D 471/04* (2013.01); *C07D 413/14* (2013.01); *C07D 417/14* (2013.01)

(58) Field of Classification Search
CPC ........................... C07D 487/04; C07D 413/14
See application file for complete search history.

(56) References Cited

FOREIGN PATENT DOCUMENTS

| DE | 103 16 081 A1 | 10/2004 |
| WO | WO 00/40554 | 7/2000 |
| WO | WO 01/81347 | 11/2001 |
| WO | WO 02/50040 | 6/2002 |
| WO | WO 02/096907 | 10/2002 |
| WO | WO 02/096426 | 12/2002 |
| WO | WO 03/087098 | 10/2003 |
| WO | WO 2004/002490 | 1/2004 |
| WO | WO 2004/032856 | 4/2004 |
| WO | WO 2004/050036 | 6/2004 |
| WO | WO 2004/089947 | 10/2004 |
| WO | WO 2005/019215 | 3/2005 |
| WO | WO 2006/021448 | 3/2006 |
| WO | WO 2006/024741 | 3/2006 |
| WO | WO 2006/032466 | 3/2006 |
| WO | WO 2006/046552 | 5/2006 |
| WO | WO 2007/012210 | 2/2007 |
| WO | WO 2007/105154 | 9/2007 |
| WO | WO 2007/107965 | 9/2007 |

(Continued)

OTHER PUBLICATIONS

Benz, Comprehensive Organic Synthesis, vol. 6, pp. 381-417 (1991).
Blakemore, Journal Chemical Society, Perkin Transactions, vol. 1, pp. 2563-2585 (2002).
Cha, Chemical Reviews, vol. 95, No. 6, pp. 1761-1795 (1995).
Chen et al., Organic Letters, vol. 8, No. 24, pp. 5609-5612 (2006).
Del Bosco et al., Tetrahedron, vol. 51, No. 31, pp. 8545-8554 (1995).
Donnecke et al., Bioorganic & Medicinal Chemistry Letters, vol. 17, pp. 3322-3329 (2007).
Gould, International Journal of Pharmacology, vol. 33, pp. 201-217 (1986).
Greene Protecting Groups in Organic Synthesis, 3rd Edition, pp. 494-653 (1999).
Greene, Protecting Groups in Organic Synthesis, 3rd Edition, pp. 17-245-specifically 133-139 and 142-143 (1999).

(Continued)

Primary Examiner — Brian McDowell
(74) Attorney, Agent, or Firm — Arent Fox LLP

(57) ABSTRACT

The invention relates to antibacterial compounds of formula I wherein one or two of U, V, W, and X represent N, the rest represent CH or, in the case of X, may also represent $CR^a$ wherein $R^a$ is fluorine; $R^1$ represents alkoxy, halogen or cyano; $R^2$ represents H, $CH_2OH$, $CH_2N_3$, $CH_2NH_2$, alkylcarbonylaminomethyl or triazol-1-ylmethyl; $R^3$ represents H, or, when n is 1, $R^3$ may also represent OH, $NH_2$, $NHCOR^6$ or triazol-1-yl; A represents $CR^4$; K represents O, NH, $OCH_2$, NHCO, $NHCH_2$, $CH_2NH$, $CH_2CH_2$, CH=CH, CHOHCHOH or $CHR^5$; $R^4$ represents H or together with $R^5$ forms a bond, or also $R^4$ can represent OH when K is not O, NH, $OCH_2$ or NHCO; $R^5$ represents OH or together with $R^4$ forms a bond; $R^6$ represents alkyl; m is 0 or 1 and n is 0 or 1; and G is as defined in the description;
and to salts of such compounds.

12 Claims, No Drawings

(56) References Cited

FOREIGN PATENT DOCUMENTS

| WO | WO 2008/126024 | 10/2008 |
|---|---|---|
| WO | WO 2008/126034 | 10/2008 |

OTHER PUBLICATIONS

Greene, Protecting Groups in Organic Synthesis, 3rd Edition, pp. 369-453 (1999).
Klapars et al., Journal of the American Chemical Society, vol. 123, pp. 7727-7729 (2001).
Kolb et al., Chemical Reviews, vol. 94, No. 8, pp. 2483-2547 (1994).
Larock, Comprehensive Organic Transformations A guide to Functional Group Preparations, 2nd Edition, pp. 779-784 (1999).
Larock, Comprehensive Organic Transformations A Guide to Functional Group Preparations 2nd Edition, pp. 1075 to 1111(1999).
Larock, Comprehensive Organic Transformations A guide to Functional Group Preparations 2nd Edition, pp. 1114-1123 (1999).
Larock, Comprehensive Organic Transformations, A Guide to Functional Group Preparations $2^{nd}$ Edition, pp. 1941-1949 (1999).
Margolis et al., Journal of Organic Chemistry, vol. 72, pp. 2232-2235 (2007).
Mitsunobu, Synthesis pp. 1-28 (1981).
Palucki et al., Journal American Chemical Society, vol. 119, pp. 3395-3396 (1997).
Radinov, Synthesis, pp. 886-891 (1986).
Sato et al., Tetrahedron, vol. 60, pp. 7899-7906 (2004).
Schaus et al, Journal of the American Chemical Society, vol. 124, No. 7, pp. 1307-1315 (2002).
Schultz et al., The Journal of Organic Chemistry, vol. 28, No. 4, pp. 1140-1142 (1963).
Shi, Accounts of Chemical Research, vol. 37, pp. 488-496 (2004).
Talbot et al. Clinical Infectious Diseases, vol. 42, pp. 657-668 (2006).
Tokitoh et al., Chemistry Letters, vol. 10, pp. 1517-1520 (1985).
Tokunaga et al., Science, vol. 277, pp. 936-938 (1997).
Toto et al., Tetrahedron Letters, vol. 47, pp. 1181-1186 (2006).
Trost et al., Tetrahedron Letters, vol. 22, No. 14, pp. 1287-1290 (1981).
Tsuzuki et al., Tetrahedron: Asymmetry, vol. 12, pp. 2989-2997 (2001).
Unknown, Index of the Science and Practice of Pharmacy , 21st Edition, Part 5, "Pharmaceutical Manufacturing" [published by Lippincott Williams & Wilkins] (2005).
Van Rheenen et al, Tetrahedron Letters, vol. 23, pp. 1973-1976 (1976).
Comprehensive Organic Transformations: A guide to Functional Group Preparation, Section nitriles, carboxylic acids and derivatives pp. 1646-1648, 2nd Edition (1999).

5-AMINOCYCLYLMETHYL-OXAZOLIDIN-2-ONE DERIVATIVES

This application is a national phase filing of International Patent Application No. PCT/IB2008/055374, filed Dec. 17, 2008, which claims priority to PCT/IB2007/055194, filed Dec. 18, 2007, and to PCT/IB2008/054170, filed Oct. 10, 2008. The disclosures of each of these applications are hereby incorporated by reference in their entirety.

The present invention concerns novel 5-aminocyclylmethyl-oxazolidin-2-one derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND

The intensive use of antibiotics has exerted a selective evolutionary pressure on microorganisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus*, *Streptococcus pneumoniae*, *Enterococcus* spp., and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- Enteroccocci are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Furthermore, the incidence of multi-drug-resistant Gram-negative strains such as Enterobacteriacea and *Pseudomonas aeruginosa*, is steadily increasing and new emerging organisms like *Acinetobacter* spp., which have been selected during therapy with the currently used antibiotics, are becoming a real problem in hospital settings. Therefore, there is a high medical need for new antibacterial agents which overcome multidrug-resistant Gram-negative bacilli such as *A. baumannii*, ESBL-producing *E. coli* and *Klebsiella* species and *Pseudomonas aeruginosa* (George H. Talbot et al. *Clinical Infectious Diseases* (2006), 42, 657-68).

In addition, microorganisms that are causing persistent infections are increasingly being recognized as causative agents or cofactors of severe chronic diseases like peptic ulcers or heart diseases.

WO 02/50040 describes certain piperazine derivatives as antibacterial agents, among which two compounds which have the structures (A1) and (A2) as shown below:

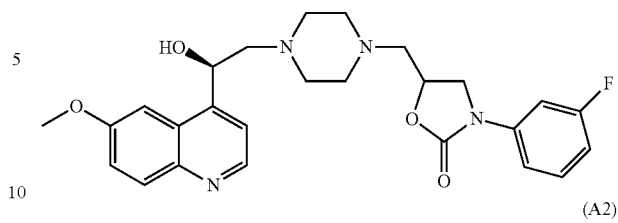

(A1)

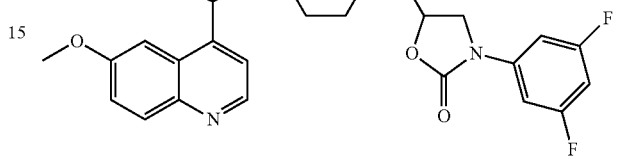

(A2)

WO 2004/032856 discloses inhibitors of the chemokine receptor CCR8 of formula (A3)

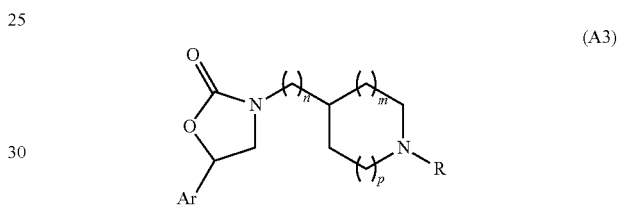

(A3)

wherein
n is 0 or 1; m is 0 or 1; p is 1, 2 or 3;
Ar is unsubstituted quinolinyl, [1,5]naphthyridinyl or pyridinyl; or quinolinyl, [1,5]naphthyridinyl or pyridinyl substituted with one or more radicals selected from the (notably) $C_1$-$C_6$ alkoxy, halogen and cyano; and
R is (notably) unsubstituted or substituted phenyl lower alkyl, unsubstituted or substituted pyridyl lower alkyl, unsubstituted or substituted indolyl lower alkyl, unsubstituted or substituted N-(lower alkyl)indolyl lower alkyl, unsubstituted or substituted quinolinyl lower alkyl, unsubstituted or substituted naphthyl lower alkyl, unsubstituted or substituted benzofuranyl lower alkyl, unsubstituted or substituted benzothiophenyl lower alkyl; wherein, when substituted, a group is substituted by one or more radicals selected from the group consisting of $C_1$-$C_6$ alkoxy, $C_1$-$C_6$ alkyl, halogen, cyano and trihalomethyl.

Besides, WO 2004/050036 describes antibacterial compounds of formula (A4)

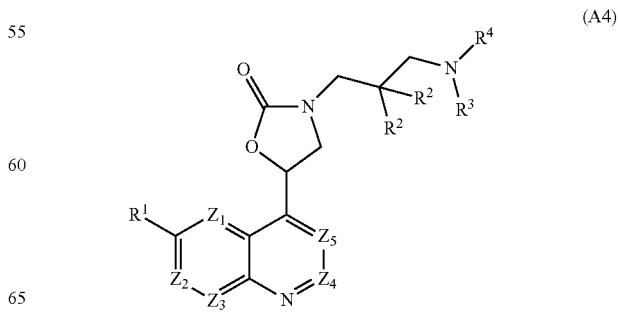

(A4)

wherein one of $Z_1$, $Z_2$, $Z_3$, $Z_4$ and $Z_5$ is N, one is $CR^{1a}$ and the remainder are CH, or one or two of $Z_1$, $Z_2$, $Z_3$, $Z_4$ and $Z_5$ are independently $CR^{1a}$ and the remainder are CH;

$R^1$ and $R^{1a}$ are independently (notably) hydrogen, halogen, ($C_1$-$C_6$)alkoxy or cyano;

each $R^2$ is independently (notably) hydrogen, OH or $NH_2$;

$R^3$ is H or unsubstituted or substituted ($C_1$-$C_6$)alkyl;

$R^4$ is a group —U—$R^5$ where U is $CH_2$, C=O or $SO_2$ and $R^5$ is notably a bicyclic heterocyclic ring system such as 4H-benzo[1,4]oxazin-3-one-6-yl, 4H-benzo[1,4]thiazin-3-one-6-yl, 3-oxo-3,4-dihydro-2H-pyrido[3,2-b][1,4]oxazine-6-yl or 3-oxo-3,4-dihydro-2H-pyrido[3,2-b][1,4]thiazine-6-yl.

The applicant has now surprisingly found that the compounds of formula I described hereafter are useful antibacterial agents.

SUMMARY OF INVENTION

Various embodiments of the invention are presented hereafter:

i) The invention firstly relates to compounds of formula I

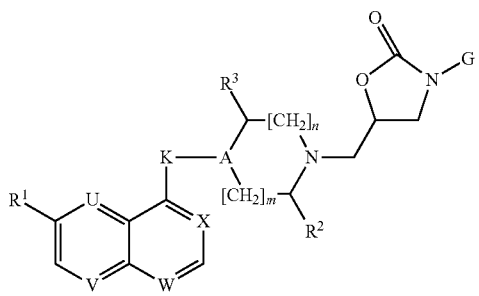

I wherein one or two (and preferably two) of U, V, W, and X represent N, the rest represent CH or, in the case of X, may also represent $CR^a$ wherein $R^a$ is fluorine;

$R^1$ represents alkoxy, halogen or cyano;

$R^2$ represents H, $CH_2OH$, $CH_2N_3$, $CH_2NH_2$, alkylcarbonylaminomethyl or triazol-1-ylmethyl;

$R^3$ represents H, or, when n is 1, $R^3$ may also represent OH, $NH_2$, $NHCOR^6$ or triazol-1-yl;

A represents $CR^4$;

K represents O, NH, $OCH_2$, NHCO, $NHCH_2$, $CH_2NH$, $CH_2CH_2$, CH=CH, CHOHCHOH or $CHR^5$;

$R^4$ represents H or together with $R^5$ forms a bond, or also $R^4$ can represent OH when K is not O, NH, $OCH_2$ or NHCO;

$R^5$ represents OH or together with $R^4$ forms a bond;

$R^6$ represents alkyl;

m is 0 or 1 and n is 0 or 1; and

G represents the group

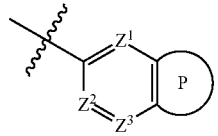

wherein $Z^1$ represents N, $Z^2$ represents CH, and $Z^3$ represents CH; or $Z^1$ represents CH, $Z^2$ represents N, and $Z^3$ represents CH or N; or $Z^1$ represents CH, $Z^2$ represents CH, and $Z^3$ represents CH or N;

and the ring P is selected from the following:

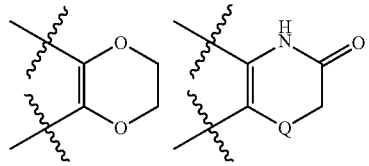

in which Q is O or S;

and to salts (in particular pharmaceutically acceptable salts) of compounds of formula I.

The compounds of formula I may contain one or more stereogenic or asymmetric centers, such as one or more asymmetric carbon atoms. Substituents at a double bond may be present in the Z- or E-configuration unless indicated otherwise. The compounds of formula I may thus be present as mixtures of stereoisomers or preferably as pure stereoisomers. Mixtures of stereoisomers may be separated in a manner known to a person skilled in the art.

The relative configuration of (xR*,yR*) stereoisomers, x and y being integers, is denoted as summarised by the following example: 6-{(R)-5-[(3R*,4R*)-3-(6-methoxy-quinazolin-4-yloxy)-4-[1,2,3]triazol-1-yl-pyrrolidin-1-ylmethyl]-2-oxo-oxazolidin-3-yl}-4H-benzo[1,4]thiazin-3-one denominates 6-{(R)-5-[(3R,4R)-3-(6-methoxy-quinazolin-4-yloxy)-4-[1,2,3]triazol-1-yl-pyrrolidin-1-ylmethyl]-2-oxo-oxazolidin-3-yl}-4H-benzo[1,4]thiazin-3-one, or 6-{(R)-5-[(3S,4S)-3-(6-methoxy-quinazolin-4-yloxy)-4-[1,2,3]triazol-1-yl-pyrrolidin-1-ylmethyl]-2-oxo-oxazolidin-3-yl}-4H-benzo[1,4]thiazin-3-one, or mixtures of these two stereoisomers.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group containing from one to four carbon atoms. Representative examples of alkyl groups include methyl, ethyl, propyl, iso-propyl, n-butyl, iso-butyl, sec-butyl and tert-butyl. The term "($C_1$-$C_x$)alkyl" (x being an integer) refers to a straight or branched chain alkyl group containing 1 to x carbon atoms.

The term "alkoxy", used alone or in combination, refers to a saturated straight or branched chain alkoxy group containing from one to four carbon atoms. Representative examples of alkoxy groups include methoxy, ethoxy, propoxy, iso-propoxy, n-butoxy, iso-butoxy, sec-butoxy and tert-butoxy. The term "($C_1$-$C_x$)alkoxy" refers to a straight or branched chain alkoxy group containing 1 to x carbon atoms.

The term "halogen" refers to fluorine, chlorine, bromine or iodine, preferably to fluorine or chlorine.

The term "alkylcarbonylaminomethyl" refers to a methyl group wherein one hydrogen has been replaced by an alkylcarbonylamino group wherein the alkyl is an alkyl as defined previously. Representative examples of alkylcarbonylaminomethyl groups include, but are not limited to, methylaminocarbonylmethyl and ethylaminocarbonylmethyl (especially methylaminocarbonylmethyl).

In this text, a bond interrupted by a wavy line shows the point of attachment of the radical drawn. For example, the radical drawn below

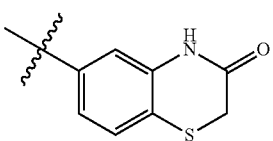 [SMILES: *c1ccc2c(c1)NC(=O)CS2]

is the 3-oxo-3,4-dihydro-2H-benzo[1,4]thiazine-6-yl group.

Moreover, in this text, when K is a dissymmetric radical, the left part of the radical as written (e.g. O in $OCH_2$) is attached to the aromatic motif

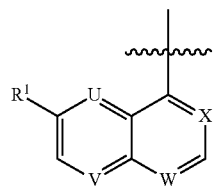

whereas the right part of the radical as written (e.g. $CH_2$ in $OCH_2$) is attached to the piperidine motif

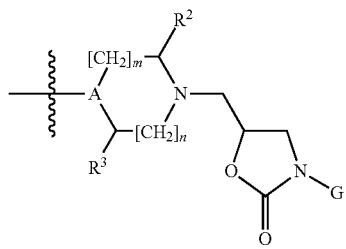

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) In another embodiment, the invention relates to compounds of formula I as defined in embodiment i) above or their salts (among which the pharmaceutically acceptable salts will be preferred), wherein G represents the following groups:

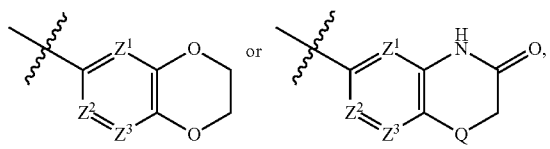

wherein $Z^1$, $Z^2$, $Z^3$ and Q are as defined in embodiment i) above.

iii) In another embodiment, the invention relates to compounds of formula I as defined in embodiment i) or ii) above or their salts (among which the pharmaceutically acceptable salts will be preferred), wherein $R^1$ represents alkoxy;

$R^3$ represents H, or, when n is 1, $R^3$ may also represent OH, $NH_2$ or triazol-1-yl;

K represents O, NH, $OCH_2$, NHCO, $NHCH_2$, $CH_2CH_2$, CH=CH, CHOHCHOH or $CHR^5$, wherein $R^5$ is as defined in embodiment i) above; and G represents the group

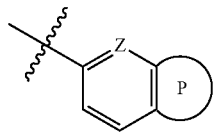

wherein Z is N or CH and the ring P is selected from the following:

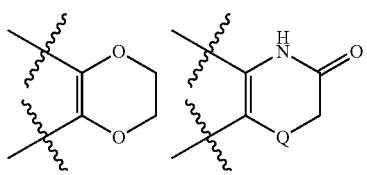

in which Q is O or S.

iv) In particular, the invention relates to compounds of formula I that are also compounds of formula $I_{CE}$

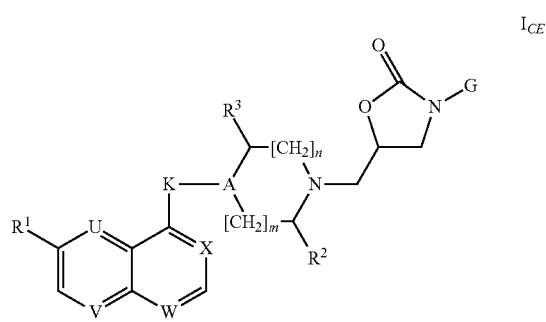

wherein

U and V each represent N and W and X each represent CH, or U and V each represent CH and W and X each represent N, or also U and W each represent N and V and X each represent CH;

$R^1$ represents alkoxy (and preferably methoxy);

$R^2$ represents H, $CH_2OH$, $CH_2N_3$, $CH_2NH_2$, alkylcarbonylaminomethyl or triazol-1-ylmethyl;

$R^3$ represents H, or, when n is 1, $R^3$ may also represent OH, $NH_2$ or triazol-1-yl;

A represents $CR^4$;

K represents O, NH, NHCO, $NHCH_2$, $CH_2CH_2$, CH=CH, CHOHCHOH or $CHR^5$;

$R^4$ represents H or together with $R^5$ forms a bond, or also $R^4$ can represent OH when K is not O, NH or NHCO;

$R^5$ represents OH or together with $R^4$ forms a bond;

m is 0 or 1 and n is 0 or 1; and

G represents one of the groups below

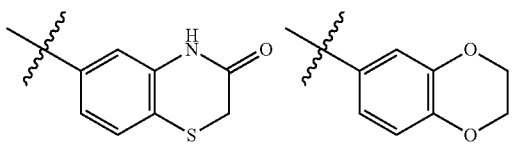

and to salts (in particular pharmaceutically acceptable salts) of compounds of formula $I_{CE}$.

v) According to a preferred embodiment of this invention, the compounds of formula I as defined in one of embodiments i) to iv) above or their salts (among which the pharmaceutically acceptable salts will be preferred) will be such that $R^1$ is $(C_1-C_3)$alkoxy (notably methoxy or ethoxy and in particular methoxy).

vi) Another preferred embodiment of this invention relates to the compounds of formula I as defined in one of embodiments i) to v) above or their salts (among which the pharmaceutically acceptable salts will be preferred) wherein U and V each represent N and W and X each represent CH, or U and V each represent CH and W and X each represent N, or also U and W each represent N and V and X each represent CH.

vii) According to one variant of the preferred embodiment vi) above, the compounds of formula I or their salts (among which the pharmaceutically acceptable salts will be preferred) will be such that U and V each represent N and W and X each represent CH.

viii) According to another variant of the preferred embodiment vi) above, the compounds of formula I or their salts (among which the pharmaceutically acceptable salts will be preferred) will be such that U and V each represent CH and W and X each represent N.

ix) According to a further variant of the preferred embodiment vi) above, the compounds of formula I or their salts (among which the pharmaceutically acceptable salts will be preferred) will be such that U and W each represent N and V and X each represent CH.

x) Yet another preferred embodiment of this invention relates to the compounds of formula I as defined in one of embodiments i) to ix) above or their salts (among which the pharmaceutically acceptable salts will be preferred) wherein:

K represents NHCO or $NHCH_2$, A represents CH, m and n are each 0 and $R^2$ and $R^3$ each represent H;

K represents O, A represents CH, m and n are each 0 and $R^2$ and $R^3$ each represent H;

K represents O, NHCO, $CH_2CH_2$ or CH=CH, A represents CH, m is 1 and n is 0 and $R^2$ and $R^3$ each represent H;

K represents O, A represents CH, m is 0 and n is 1, $R^2$ represents H and $R^3$ represents OH;

K represents O, A represents CH, m and n are each 1 and $R^2$ and $R^3$ each represent H;

K represents O, A represents CH, m is 0 and n is 1, $R^2$ represents H and $R^3$ represents $NH_2$ or triazol-1-yl;

K represents O, A represents CH, m is 1 and n is 0, $R^2$ represents $CH_2OH$, $CH_2NH_2$, acetylaminomethyl or triazol-1-ylmethyl and $R^3$ represents H;

K represents $CR^5$, A represents $CR^4$, $R^4$ and $R^5$ together forming a bond (that is, the group KA represents CH=C), m and n are each 1 and $R^2$ and $R^3$ each represent H;

K represents $CHR^5$, $R^5$ represents OH, A represents $CR^4$, $R^4$ represents OH, m and n are each 1 and $R^2$ and $R^3$ each represent H; or K represents CHOHCHOH, A represents CH, m is 1 and n is 0 and $R^2$ and $R^3$ each represent H.

xi) According to one variant of the preferred embodiment x), the compounds of formula I or their salts (among which the pharmaceutically acceptable salts will be preferred) wherein:

K represents NHCO or $NHCH_2$, A represents CH, m and n are each 0 and $R^2$ and $R^3$ each represent H;

K represents O, A represents CH, m and n are each 0 and $R^2$ and $R^3$ each represent H;

K represents O, NHCO, $CH_2CH_2$ or CH=CH, A represents CH, m is 1 and n is 0 and $R^2$ and $R^3$ each represent H;

K represents O, A represents CH, m is 0 and n is 1, $R^2$ represents H and $R^3$ represents OH;

K represents O, A represents CH, m and n are each 1 and $R^2$ and $R^3$ each represent H;

K represents O, A represents CH, m is 0 and n is 1, $R^2$ represents H and $R^3$ represents $NH_2$ or triazol-1-yl;

K represents O, A represents CH, m is 1 and n is 0, $R^2$ represents $CH_2OH$, $CH_2NH_2$, acetylaminomethyl or triazol-1-ylmethyl and $R^3$ represents H; or K represents $CR^5$, A represents $CR^4$, $R^4$ and $R^5$ together forming a bond (that is, the group KA represents CH=C), m and n are each 1 and $R^2$ and $R^3$ each represent H.

xii) Preferably, the compounds of formula I according to embodiment xi) or their salts (among which the pharmaceutically acceptable salts will be preferred) will be such that:

K represents NHCO or $NHCH_2$, A represents CH, m and n are each 0 and $R^2$ and $R^3$ each represent H;

K represents O, A represents CH, m and n are each 0 and $R^2$ and $R^3$ each represent H;

K represents O, NHCO, $CH_2CH_2$ or CH=CH, A represents CH, m is 1 and n is 0 and $R^2$ and $R^3$ each represent H;

K represents O, A represents CH, m is 0 and n is 1, $R^2$ represents H and $R^3$ represents OH;

K represents O, A represents CH, m and n are each 1 and $R^2$ and $R^3$ each represent H;

K represents O, A represents CH, m is 0 and n is 1, $R^2$ represents H and $R^3$ represents $NH_2$ or triazol-1-yl;

K represents O, A represents CH, m is 1 and n is 0, $R^2$ represents $CH_2OH$ or triazol-1-ylmethyl and $R^3$ represents H; or K represents $CR^5$, A represents $CR^4$, $R^4$ and $R^5$ together forming a bond (that is, the group KA represents CH=C), m and n are each 1 and $R^2$ and $R^3$ each represent H.

xiii) More preferably, the compounds of formula I according to embodiment xi) or their salts (among which the pharmaceutically acceptable salts will be preferred) will be such that A represents CH and:

K represents NHCO or $NHCH_2$, m and n are each 0 and $R^2$ and $R^3$ each represent H;

K represents O, m and n are each 0 and $R^2$ and $R^3$ each represent H;
K represents O, NHCO, $CH_2CH_2$ or CH=CH, m is 1 and n is 0 and $R^2$ and $R^3$ each represent H;
K represents O, m is 0 and n is 1, $R^2$ represents H and $R^3$ represents OH; or
K represents O, m and n are each 1 and $R^2$ and $R^3$ each represent H.

xiv) According to another variant of the preferred embodiment x), the compounds of formula I or their salts (among which the pharmaceutically acceptable salts will be preferred) wherein:
K represents $CHR^5$, $R^5$ represents OH, A represents $CR^4$, $R^4$ represents OH, m and n are each 1 and $R^2$ and $R^3$ each represent H;
K represents CHOHCHOH, A represents CH, m is 1 and n is 0 and $R^2$ and $R^3$ each represent H.

xv) According to one main variant of this invention, the compounds of formula I or their salts (among which the pharmaceutically acceptable salts will be preferred) as defined in one of embodiments i) to xiii) will be such that m and n are each 0.

xvi) According to further main variant of this invention, the compounds of formula I or their salts (among which the pharmaceutically acceptable salts will be preferred) as defined in one of embodiments i) to xiii) will be such that m is 0 and n is 1.

xvii) According to another main variant of this invention, the compounds of formula I or their salts (among which the pharmaceutically acceptable salts will be preferred) as defined in one of embodiments i) to xiv) will be such that m is 1 and n is 0.

xviii) According to yet another main variant of this invention, the compounds of formula I or their salts (among which the pharmaceutically acceptable salts will be preferred) as defined in one of embodiments i) to xiv) will be such that m and n are each 1.

xix) According to yet another main variant of this invention, the compounds of formula I as defined in one of embodiments i) to xviii) above or their salts (among which the pharmaceutically acceptable salts will be preferred) will be such that the ring P of the group G is

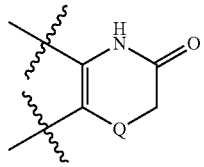

in which Q is O or S (and in particular S).

xx) According to yet another main variant of this invention, the compounds of formula I as defined in one of embodiments i) to xviii) above or their salts (among which the pharmaceutically acceptable salts will be preferred) will be such that the ring P of the group G is

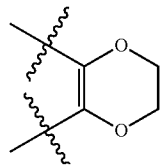 [SMILES: *C1=C(*)OCCO1]

xxi) Preferably, the compounds of formula I as defined in embodiments xix) or xx) above or their salts (among which the pharmaceutically acceptable salts will be preferred) will be such that Z is CH.

xxii) More preferably, the compounds of formula I as defined in embodiments xix) or xx) above or their salts (among which the pharmaceutically acceptable salts will be preferred) will be such that the group G is 3-oxo-3,4-dihydro-2H-benzo[1,4]thiazine-6-yl or 2,3-dihydro-benzo[1,4]dioxin-6-yl (especially 3-oxo-3,4-dihydro-2H-benzo[1,4]thiazine-6-yl). xxiii) A particular variant of this invention relates to the compounds of formula I as defined in one of embodiments i) to xiii) and xv) to xxii) above or to their salts (among which the pharmaceutically acceptable salts will be preferred) wherein K represents O or $OCH_2$.

xxiv) Another particular variant of this invention relates to the compounds of formula I as defined in one of embodiments i) to xiii) and xv) to xxii) above or to their salts (among which the pharmaceutically acceptable salts will be preferred) wherein K represents NH, NHCO or $NHCH_2$.

xxv) According to a sub-variant of particular variant xxiv), the compounds of formula I as defined in one embodiments xxiv) above or their salts (among which the pharmaceutically acceptable salts will be preferred) will be such that K represents NH.

xxvi) According to another sub-variant of particular variant xxiv), the compounds of formula I as defined in one embodiments xxiv) above or their salts (among which the pharmaceutically acceptable salts will be preferred) will be such that K represents NHCO.

xxvii) According to yet another sub-variant of particular variant xxiv), the compounds of formula I as defined in one embodiments xxiv) above or their salts (among which the pharmaceutically acceptable salts will be preferred) will be such that K represents $NHCH_2$.

xxviii) Yet another particular variant of this invention relates to the compounds of formula I as defined in one of embodiments i) to xxii) above or to their salts (among which the pharmaceutically acceptable salts will be preferred) wherein K represents $CH_2CH_2$, CH=CH, CHOHCHOH or $CHR^5$.

xxix) Particularly preferred are the following compounds of formula I as defined in one of embodiments i) to iv):
6-{(R)-5-[3-(6-methoxy-[1,5]naphthyridin-4-yloxy)-azetidin-1-ylmethyl]-2-oxo-oxazolidin-3-yl}-4H-benzo[1,4]thiazin-3-one;
6-{(R)-5-[(R)-3-(6-methoxy-quinazolin-4-yloxy)-pyrrolidin-1-ylmethyl]-2-oxo-oxazolidin-3-yl}-4H-benzo[1,4]thiazin-3-one;
6-{(R)-5-[(S)-3-(6-methoxy-quinazolin-4-yloxy)-pyrrolidin-1-ylmethyl]-2-oxo-oxazolidin-3-yl}-4H-benzo[1,4]thiazin-3-one;
(R)-3-(2,3-dihydro-benzo[1,4]dioxin-6-yl)-5-[3-(6-methoxy-quinazolin-4-yloxy)-pyrrolidin-1-ylmethyl]-oxazolidin-2-one;
6-{(R)-5-[(2S,4S)-2-hydroxymethyl-4-(6-methoxy-quinazolin-4-yloxy)-pyrrolidin-1-ylmethyl]-2-oxo-oxazolidin-3-yl}-4H-benzo[1,4]thiazin-3-one;
6-{(R)-5-[(2S,4S)-2-azidomethyl-4-(6-methoxy-quinazolin-4-yloxy)-pyrrolidin-1-ylmethyl]-2-oxo-oxazolidin-3-yl}-4H-benzo[1,4]thiazin-3-one;
1-[(R)-2-oxo-3-(3-oxo-3,4-dihydro-2H-benzo[1,4]thiazin-6-yl)-oxazolidin-5-ylmethyl]-azetidine-3-carboxylic acid (6-methoxy-[1,5]naphthyridin-4-yl)-amide;
1-[(R)-2-oxo-3-(3-oxo-3,4-dihydro-2H-benzo[1,4]thiazin-6-yl)-oxazolidin-5-ylmethyl]-pyrrolidine-3-carboxylic acid (6-methoxy-[1,5]naphthyridin-4-yl)-amide;

6-((R)-5-{3-[(E)-2-(6-methoxy-[1,5]naphthyridin-4-yl)-vinyl]-pyrrolidin-1-ylmethyl}-2-oxo-oxazolidin-3-yl)-4H-benzo[1,4]thiazin-3-one;

6-((R)-5-{3-[2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one;

6-((R)-5-{3-[(1R,2R)-1,2-dihydroxy-2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one;

6-{(R)-5-[4-(3-methoxy-quinoxalin-5-ylmethylene)-piperidin-1-ylmethyl]-2-oxo-oxazolidin-3-yl}-4H-benzo[1,4]thiazin-3-one;

6-((R)-5-{4-hydroxy-4-[hydroxy-(3-methoxy-quinoxalin-5-yl)-methyl]-piperidin-1-ylmethyl}-2-oxo-oxazolidin-3-yl)-4H-benzo[1,4]thiazin-3-one;

6-((R)-5-{3-[(6-methoxy-[1,5]naphthyridin-4-ylamino)-methyl]-azetidin-1-ylmethyl}-2-oxo-oxazolidin-3-yl)-4H-benzo[1,4]thiazin-3-one;

6-{(R)-5-[(2S,4S)-2-aminomethyl-4-(6-methoxy-quinazolin-4-yloxy)-pyrrolidin-1-ylmethyl]-2-oxo-oxazolidin-3-yl}-4H-benzo[1,4]thiazin-3-one;

6-{(R)-5-[(3R*,4R*)-3-(6-methoxy-quinazolin-4-yloxy)-4-[1,2,3]triazol-1-yl-pyrrolidin-1-ylmethyl]-2-oxo-oxazolidin-3-yl}-4H-benzo[1,4]thiazin-3-one;

N-{(2S,4S)-4-(6-methoxy-quinazolin-4-yloxy)-1-[(R)-2-oxo-3-(3-oxo-3,4-dihydro-2H-benzo[1,4]thiazin-6-yl)-oxazolidin-5-ylmethyl]-pyrrolidin-2-ylmethyl}-acetamide;

6-{(R)-5-[(3R*,4R*)-3-amino-4-(6-methoxy-quinazolin-4-yloxy)-pyrrolidin-1-ylmethyl]-2-oxo-oxazolidin-3-yl}-4H-benzo[1,4]thiazin-3-one;

6-{(R)-5-[(2S,4S)-4-(6-methoxy-quinazolin-4-yloxy)-2-[1,2,3]triazol-1-ylmethyl-pyrrolidin-1-ylmethyl]-2-oxo-oxazolidin-3-yl}-4H-benzo[1,4]thiazin-3-one;

6-{(R)-5-[4-(6-methoxy-quinazolin-4-yloxy)-piperidin-1-ylmethyl]-2-oxo-oxazolidin-3-yl}-4H-benzo[1,4]thiazin-3-one;

6-{(R)-5-[(3R*,4S*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one;

6-{(R)-5-[(3R*,4R*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one;

as well as the salts (in particular the pharmaceutically acceptable salts) thereof.

xxx) Furthermore, the following compounds of formula I as defined in one of embodiments i) to iv) are particularly preferred:

6-{(R)-5-[3-(6-methoxy-[1,5]naphthyridin-4-yloxy)-azetidin-1-ylmethyl]-2-oxo-oxazolidin-3-yl}-4H-benzo[1,4]thiazin-3-one;

6-{(R)-5-[(R)-3-(6-methoxy-quinazolin-4-yloxy)-pyrrolidin-1-ylmethyl]-2-oxo-oxazolidin-3-yl}-4H-benzo[1,4]thiazin-3-one;

6-{(R)-5-[(S)-3-(6-methoxy-quinazolin-4-yloxy)-pyrrolidin-1-ylmethyl]-2-oxo-oxazolidin-3-yl}-4H-benzo[1,4]thiazin-3-one;

(R)-3-(2,3-dihydro-benzo[1,4]dioxin-6-yl)-5-[(R)-3-(6-methoxy-quinazolin-4-yloxy)-pyrrolidin-1-ylmethyl]-oxazolidin-2-one;

(R)-3-(2,3-dihydro-benzo[1,4]dioxin-6-yl)-5-[(S)-3-(6-methoxy-quinazolin-4-yloxy)-pyrrolidin-1-ylmethyl]-oxazolidin-2-one;

6-{(R)-5-[(2S,4S)-2-hydroxymethyl-4-(6-methoxy-quinazolin-4-yloxy)-pyrrolidin-1-ylmethyl]-2-oxo-oxazolidin-3-yl}-4H-benzo[1,4]thiazin-3-one;

6-{(R)-5-[(2S,4S)-2-azidomethyl-4-(6-methoxy-quinazolin-4-yloxy)-pyrrolidin-1-ylmethyl]-2-oxo-oxazolidin-3-yl}-4H-benzo[1,4]thiazin-3-one;

1-[(R)-2-oxo-3-(3-oxo-3,4-dihydro-2H-benzo[1,4]thiazin-6-yl)-oxazolidin-5-ylmethyl]-azetidine-3-carboxylic acid (6-methoxy-[1,5]naphthyridin-4-yl)-amide;

(R)-1-[(R)-2-oxo-3-(3-oxo-3,4-dihydro-2H-benzo[1,4]thiazin-6-yl)-oxazolidin-5-ylmethyl]-pyrrolidine-3-carboxylic acid (6-methoxy-[1,5]naphthyridin-4-yl)-amide;

(S)-1-[(R)-2-oxo-3-(3-oxo-3,4-dihydro-2H-benzo[1,4]thiazin-6-yl)-oxazolidin-5-ylmethyl]-pyrrolidine-3-carboxylic acid (6-methoxy-[1,5]naphthyridin-4-yl)-amide;

6-((R)-5-{(R)-3-[(E)-2-(6-methoxy-[1,5]naphthyridin-4-yl)-vinyl]-pyrrolidin-1-ylmethyl}-2-oxo-oxazolidin-3-yl)-4H-benzo[1,4]thiazin-3-one;

6-((R)-5-{(S)-3-[(E)-2-(6-methoxy-[1,5]naphthyridin-4-yl)-vinyl]-pyrrolidin-1-ylmethyl}-2-oxo-oxazolidin-3-yl)-4H-benzo[1,4]thiazin-3-one;

6-((R)-5-{(R)-3-[2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one;

6-((R)-5-{(S)-3-[2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one;

6-((R)-5-{(R)-3-[(1R,2R)-1,2-dihydroxy-2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one;

6-((R)-5-{(S)-3-[(1R,2R)-1,2-dihydroxy-2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one;

6-{(R)-5-[4-(3-methoxy-quinoxalin-5-ylmethylene)-piperidin-1-ylmethyl]-2-oxo-oxazolidin-3-yl}-4H-benzo[1,4]thiazin-3-one;

6-((R)-5-{4-hydroxy-4-[(R)-hydroxy-(3-methoxy-quinoxalin-5-yl)-methyl]-piperidin-1-ylmethyl}-2-oxo-oxazolidin-3-yl)-4H-benzo[1,4]thiazin-3-one;

6-((R)-5-{4-hydroxy-4-[(S)-hydroxy-(3-methoxy-quinoxalin-5-yl)-methyl]-piperidin-1-ylmethyl}-2-oxo-oxazolidin-3-yl)-4H-benzo[1,4]thiazin-3-one;

6-((R)-5-{3-[(6-methoxy-[1,5]naphthyridin-4-ylamino)-methyl]-azetidin-1-ylmethyl}-2-oxo-oxazolidin-3-yl)-4H-benzo[1,4]thiazin-3-one;

6-{(R)-5-[(2S,4S)-2-aminomethyl-4-(6-methoxy-quinazolin-4-yloxy)-pyrrolidin-1-ylmethyl]-2-oxo-oxazolidin-3-yl}-4H-benzo[1,4]thiazin-3-one;

6-{(R)-5-[(3R*,4R*)-3-(6-methoxy-quinazolin-4-yloxy)-4-[1,2,3]triazol-1-yl-pyrrolidin-1-ylmethyl]-2-oxo-oxazolidin-3-yl}-4H-benzo[1,4]thiazin-3-one;

N-{(2S,4S)-4-(6-methoxy-quinazolin-4-yloxy)-1-[(R)-2-oxo-3-(3-oxo-3,4-dihydro-2H-benzo[1,4]thiazin-6-yl)-oxazolidin-5-ylmethyl]-pyrrolidin-2-ylmethyl}-acetamide;

6-{(R)-5-[(3R*,4R*)-3-amino-4-(6-methoxy-quinazolin-4-yloxy)-pyrrolidin-1-ylmethyl]-2-oxo-oxazolidin-3-yl}-4H-benzo[1,4]thiazin-3-one;

6-{(R)-5-[(2S,4S)-4-(6-methoxy-quinazolin-4-yloxy)-2-[1,2,3]triazol-1-ylmethyl-pyrrolidin-1-ylmethyl]-2-oxo-oxazolidin-3-yl}-4H-benzo[1,4]thiazin-3-one;

6-{(R)-5-[4-(6-methoxy-quinazolin-4-yloxy)-piperidin-1-ylmethyl]-2-oxo-oxazolidin-3-yl}-4H-benzo[1,4]thiazin-3-one;

6-{(R)-5-[(3R*,4S*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one;

6-{(R)-5-[(3R*,4R*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one;

as well as the salts (in particular the pharmaceutically acceptable salts) thereof.

xxxi) Furthermore, the following compounds of formula I as defined in one of embodiments i) to iv) are particularly preferred:

6-{(R)-5-[3-(3-fluoro-6-methoxy-[1,5]naphthyridin-4-ylamino)-azetidin-1-ylmethyl]-2-oxo-oxazolidin-3-yl}-4H-benzo[1,4]oxazin-3-one;
6-{(R)-5-[3-(6-methoxy-[1,5]naphthyridin-4-ylamino)-azetidin-1-ylmethyl]-2-oxo-oxazolidin-3-yl}-4H-benzo[1,4]oxazin-3-one;
6-{(R)-5-[3-(6-methoxy-quinolin-4-ylamino)-azetidin-1-ylmethyl]-2-oxo-oxazolidin-3-yl}-4H-benzo[1,4]oxazin-3-one;
6-((R)-5-{3-[(3-fluoro-6-methoxy-[1,5]naphthyridin-4-ylmethyl)-amino]-azetidin-1-ylmethyl}-2-oxo-oxazolidin-3-yl)-4H-benzo[1,4]oxazin-3-one;
6-((R)-5-{3-[(6-methoxy-[1,5]naphthyridin-4-ylmethyl)-amino]-azetidin-1-ylmethyl}-2-oxo-oxazolidin-3-yl)-4H-benzo[1,4]oxazin-3-one;
6-((R)-5-{3-[(3-fluoro-6-methoxy-quinolin-4-ylmethyl)-amino]-azetidin-1-ylmethyl}-2-oxo-oxazolidin-3-yl)-4H-benzo[1,4]oxazin-3-one;
6-((R)-5-{3-[(6-methoxy-quinolin-4-ylmethyl)-amino]-azetidin-1-ylmethyl}-2-oxo-oxazolidin-3-yl)-4H-benzo[1,4]oxazin-3-one;
(R)-3-(2,3-dihydro-benzo[1,4]dioxin-6-yl)-5-[3-(6-methoxy-quinazolin-4-yloxymethyl)-azetidin-1-ylmethyl]-oxazolidin-2-one;
6-{(R)-5-[4-(6-methoxy-quinazolin-4-yloxy)-piperidin-1-ylmethyl]-2-oxo-oxazolidin-3-yl}-4H-benzo[1,4]oxazin-3-one;
N-{(3R*,4R*)-4-(6-methoxy-quinazolin-4-yloxy)-1-[(R)-2-oxo-3-(3-oxo-3,4-dihydro-2H-benzo[1,4]thiazin-6-yl)-oxazolidin-5-ylmethyl]-pyrrolidin-3-yl}-acetamide;
(R)-3-(6,7-dihydro-[1,4]dioxino[2,3-c]pyridazin-3-yl)-5-[3-(6-methoxy-quinazolin-4-yloxy)-pyrrolidin-1-ylmethyl]-oxazolidin-2-one (such as especially (R)-3-(6,7-dihydro-[1,4]dioxino[2,3-c]pyridazin-3-yl)-5-[(R)-3-(6-methoxy-quinazolin-4-yloxy)-pyrrolidin-1-ylmethyl]-oxazolidin-2-one or (R)-3-(6,7-dihydro-[1,4]dioxino[2,3-c]pyridazin-3-yl)-5-[(S)-3-(6-methoxy-quinazolin-4-yloxy)-pyrrolidin-1-ylmethyl]-oxazolidin-2-one);
6-((R)-5-{3-[(3-methoxy-quinoxalin-5-ylmethyl)-amino]-azetidin-1-ylmethyl}-2-oxo-oxazolidin-3-yl)-4H-benzo[1,4]oxazin-3-one;
6-{(R)-5-[4-(6-methoxy-[1,5]naphthyridin-4-ylamino)-piperidin-1-ylmethyl]-2-oxo-oxazolidin-3-yl}-4H-benzo[1,4]oxazin-3-one;
6-{(R)-5-[3-(6-methoxy-[1,5]naphthyridin-4-ylamino)-azetidin-1-ylmethyl]-2-oxo-oxazolidin-3-yl}-4H-benzo[1,4]thiazin-3-one;
6-{(R)-5-[3-(6-methoxy-quinolin-4-ylamino)-azetidin-1-ylmethyl]-2-oxo-oxazolidin-3-yl}-4H-benzo[1,4]thiazin-3-one;
4-{1-[(R)-2-oxo-3-(3-oxo-3,4-dihydro-2H-benzo[1,4]thiazin-6-yl)-oxazolidin-5-ylmethyl]-azetidin-3-ylamino}-quinoline-6-carbonitrile;
6-{(R)-5-[3-(6-fluoro-quinolin-4-ylamino)-azetidin-1-ylmethyl]-2-oxo-oxazolidin-3-yl}-4H-benzo[1,4]thiazin-3-one;
6-{(R)-5-[4-(6-methoxy-[1,5]naphthyridin-4-ylamino)-piperidin-1-ylmethyl]-2-oxo-oxazolidin-3-yl}-4H-benzo[1,4]thiazin-3-one;
6-{(R)-5-[4-(6-methoxy-quinolin-4-ylamino)-piperidin-1-ylmethyl]-2-oxo-oxazolidin-3-yl}-4H-benzo[1,4]thiazin-3-one;
(R)-3-(2,3-dihydro-benzo[1,4]dioxin-6-yl)-5-[3-(6-methoxy-[1,5]naphthyridin-4-ylamino)-azetidin-1-ylmethyl]-oxazolidin-2-one;
6-{(R)-5-[3-(6-fluoro-quinolin-4-ylamino)-azetidin-1-ylmethyl]-2-oxo-oxazolidin-3-yl}-4H-benzo[1,4]oxazin-3-one;
(R)-3-(2,3-dihydro-benzo[1,4]dioxin-6-yl)-5-[3-(6-methoxy-quinolin-4-yloxy)-azetidin-1-ylmethyl]-oxazolidin-2-one;
as well as the salts (in particular the pharmaceutically acceptable salts) thereof.

The compounds of formula I according to the invention, i.e. according to one of embodiments i) to xxxi), are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtherias*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), *viridans* streptococci, *Corynebacterium minutissimum, Clostridium* spp., or *Bartonella henselae*; uncomplicated acute urinary tract infections related to infection by *Staphylococcus aureus*, coagulase-negative *staphylococcal* species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuber-* culosis, *M. leprae*, *M. paratuberculosis*, *M. kansasii*, or *M. chelonei*; gastroenteritis related to infection by *Campylobacter jejuni*; intestinal protozoa related to infection by *Cryptosporidium* spp.; odontogenic infection related to infection by *viridans* streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament for the treatment of infections that are mediated by bacteria such as *E. coli*, *Klebsiella pneumoniae* and other *Enterobacteriaceae*, *Acinetobacter* spp., *Stenothrophomonas maltophilia*, *Neisseria meningitidis*, *Bacillus cereus*, *Bacillus anthracis*, *Corynebacterium* spp., *Propionibacterium acnes* and bacteroide spp.

The compounds of formula I according to the present invention are further useful to treat protozoal infections caused by *Plasmodium malaria*, *Plasmodium falciparum*, *Toxoplasma gondii*, *Pneumocystis carinii*, *Trypanosoma brucei* and *Leishmania* spp.

The present list of pathogens is to be interpreted merely as examples and in no way as limiting.

One aspect of this invention therefore relates to the use of a compound of formula I according to this invention, or of a pharmaceutically acceptable salt thereof, for the manufacture of a medicament for the prevention or treatment of a bacterial infection.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a compound of formula I or a pharmaceutically acceptable salt thereof.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_{CE}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

DETAILED DESCRIPTION OF THE INVENTION

Preparation of Compounds of Formula I

Abbreviations

The following abbreviations are used throughout the specification and the examples:
Ac acetyl
AcOH acetic acid
aq. aqueous
AD-mix α $(DHQ)_2PHAL$, $K_3Fe(CN)_6$, $K_2CO_3$ and $K_2OsO_4.2H_2O$
AD-mix β $(DHQD)_2PHAL$, $K_3Fe(CN)_6$, $K_2CO_3$ and $K_2OsO_4.2H_2O$
BINAP rac-2,2'-bis(diphenylphosphino)-1,1'-binaphthyl
Boc tert-butoxycarbonyl
Cbz benzyloxycarbonyl
CC column chromatography over silica gel
CDI 1,1'-carbonyldiimidazole
DCC dicyclohexylcarbodiimide
DCM dichloromethane
DCE 1,2-dichloroethane
DEAD diethylazodicarboxylate
$(DHQ)_2PHAL$ 1,4-bis(dihydroquinine)phthalazine
$(DHQD)_2PHAL$ 1,4-bis(dihydroquinidine)phthalazine
DIAD diisobutylazodicarboxylate
DIBAH diisobutylaluminium hydride
DIPEA N,N-diisopropylethylamine
DMA N,N-dimethylacetamide
DMAP 4-dimethylaminopyridine
1,2-DME 1,2-dimethoxyethane
DMF N,N-dimethylformamide
DMSO dimethylsulfoxide
DPEphos bis(2-diphenylphosphinophenyl)ether
EA ethyl acetate
EDCI 1-(3-dimethylaminopropyl)-3-ethylcarbodiimide hydrochloride
eq equivalent
ESI Electron Spray Ionisation
Et ethyl
FC flash chromatography
Fmoc 9-fluorenylmethoxycarbonyl
h hour(s)
HATU (O-(7-azabenzotriazol-1-yl)-1,1,3,3-tetramethyluronium hexafluorophoshate
Hept heptane
Hex hexane HOBT hydroxybenzotriazole
HPLC high performance liquid chromatography
HV high vacuum conditions
KHMDS potassium hexamethyldisilazide
LDA lithium diisopropylamide
mCPBA m-chloroperbenzoic acid
Me methyl
MeCN acetonitrile
min minute(s)
MS mass spectrometry
Ms methanesulfonyl
nBu n-butyl
NMO N-methylmorpholine-N-oxide
NMP N-methylpyrrolidone
org. organic
Pd/C palladium on charcoal
Ph phenyl
rac racemic
rt room temperature
TBAF tetrabutyl ammonium fluoride
TBDMS tert-butyldimethylsilyl
TBDPS tert-butyldiphenylsilyl
tBu tert-butyl
TBDMSOTf tert-butyldimethylsilyltrifluoromethanesulphonate
TEA triethylamine
TEMPO 2,2,4,4-tetramethylpiperidine-1-oxyl
Tf trifluoromethanesulfonyl(triflyl)
TFA trifluoroacetic acid
THF tetrahydrofuran
TMS trimethylsilyl
Ts p-toluenesulfonyl
Z (in amino acids) benzyloxycarbonyl
General Reaction Techniques:
General Reaction Technique 1: Amine Protection:

Amines are usually protected as carbamates such as Alloc, Cbz, Boc or Fmoc. They are obtained by reacting the amine with allyl or benzyl chloroformate, di tert-butyl dicarbonate or Fmoc-Cl in presence of a base such as NaOH, TEA, DMAP or imidazole. They can also be protected as N-benzyl derivatives by reaction with benzyl bromide or chloride in presence of a base such as $Na_2CO_3$ or TEA. Alternatively, N-benzyl derivatives can be obtained through reductive amination in presence of benzaldehyde and a borohydride reagent such as $NaBH_4$, $NaBH_3CN$ or $NaBH(OAc)_3$ in a solvent such as EtOH. Further strategies to introduce other amine protecting groups have been described in *Protecting Groups in Organic Synthesis*, 3rd Ed (1999), 494-653; T. W. Greene, P. G. M. Wuts (Publisher: John Wiley and Sons, Inc., New York, N.Y.).

General Reaction Technique 2: Protection of Alcohols:

The alcohols are protected as silyl ether (usually TBDMS or TBDPS). The alcohol is reacted with the required silyl chloride reagent (TBDMS-Cl or TBDPS-Cl) in presence of a base such as imidazole or TEA in a solvent such as DCM or DMF between +10° C. and +40° C. The TBDMS group can also be introduced by reaction with TBDMSOTf in presence of lutidine. Further strategies to introduce other alcohol protecting groups have been described in *Protecting Groups in Organic Synthesis*, 3rd Ed (1999), 23-147; T. W. Greene, P. G. M. Wuts (Publisher: John Wiley and Sons, Inc., New York, N.Y.).

General Reaction Technique 3: Hydroxy Deprotection:

The silyl ether groups are removed either using fluoride anion sources such as TBAF in THF, HF in MeCN or pyridine. HF in THF between 0° C. and +40° C. or using acidic conditions such as AcOH in THF/MeOH or HCl in MeOH. Further methods to remove the TBDMS and TBDPS groups are given in Protecting Groups in Organic Synthesis 3rd Ed; 1999, 133-139 and 142-143 respectively; T. W. Greene, P. G. M. Wuts; (Publisher: John Wiley and Sons, Inc., New York, N.Y.). Further general methods to remove alcohol protecting groups are described in *Protecting Groups in Organic Synthesis*, 3rd Ed (1999), 23-147; T. W. Greene, P. G. M. Wuts (Publisher: John Wiley and Sons, Inc., New York, N.Y.).

General Reaction Technique 4: Oxazolidinone Formation Via Glycidyl Esters:

The relevant carbamate derived from an aniline or a 2-aminopyridine is reacted in a dry solvent such as THF or DMF with a strong org. base such as n-BuLi between −100° C. and +30° C. or with tBuOLi or tBuOK or KHMDS between −100° C. and −30° C. in DMF or THF The anion is reacted at these temperatures with the required epoxide and allowed to reach rt.

General Reaction Technique 5: Metal Catalyzed Cross-coupling Reactions for N and O Arylation:

The aromatic halide or the triflate is reacted with the corresponding amine in presence of a palladium catalyst (as described in *J. Am. Chem. Soc.* (1997), 119, 3395-96 or *J. Org. Chem.* (2007), 72, 2232-2235) and of a base such as tBuOK or LDA between +20° C. and +100° C. In the Goldberg variant, the reaction is performed between an aromatic halide or triflate and a lactam, a carbamate or an amine in presence of CuI, an inorganic base such as $K_2CO_3$ or $K_3PO_4$ between +40° C. and +110° C., as described in *Tetrahedron Letters* (2006), 47, 1181-86 or *J. Am. Chem. Soc.* (2001), 123, 7727-29. For the metal catalyzed N-arylation of 2-oxazolidinones, the reaction is performed in presence of CuI, 1,1,1-tris(hydroxymethyl)ethane and $Cs_2CO_3$ (*Org. Lett.* (2006), 8, 5609-5612) or $Pd(OAc)_2$ and DPEphos in presence of $K_3PO_4$ (*J. Org. Chem.* (2007), 72, 2232-2235).

General Reaction Technique 6: Mitsunobu Reaction:

Mitsunobu coupling has been reviewed by O. Mitsunobu in *Synthesis* (1981), 1. The reaction between a phenol, a thiol or a sulphonamide and an alcohol is performed in the presence of DEAD or DIAD and $PPh_3$. The reaction may be performed in a wide range of solvents such as DMF, THF or DCM and within a wide range of temperatures (between −78° C. and 50° C.).

General Reaction Technique 7: Alkylation:

The amine derivative is reacted with a compound of formula alkyl-$L^2$, wherein $L^2$ represents OMs, OTf, OTs, Cl, Br or I, or the appropriate derivative having a side group $L^2$ as previously defined, or an allyl or homoallyl halogenide in presence of an inorganic base such as $K_2CO_3$ or an org. base such as TEA in a solvent such as THF between 0° C. and +80° C. Further details can be found in *Comprehensive Organic Transformations. A guide to Functional Group Preparations;* 2nd Edition, R. C. Larock, Wiley-VC; New York, Chichester, Weinheim, Brisbane, Singapore, Toronto, (1999). Section Amines p. 779.

General Reaction Technique 8: Alcohol Activation:

The alcohol is reacted with MsCl, TfCl or TsCl in presence of a base such as TEA in a dry aprotic solvent such as pyridine, THF or DCM between −30° C. and +50° C. In the case of the trifluoromethanesulfonate or methanesulfonate, $Tf_2O$ or $Ms_2O$ can also be used. These sulfonates can be reacted with sodium iodide in acetone between +40° C. and +80° C. delivering the corresponding iodo derivatives.

General Reaction Technique 9: Amide Coupling:

The carboxylic acid is reacted with the amine in presence of an activating agent such as DCC, EDCI, HOBT, n-propylphosphonic cyclic anhydride, HATU, CDI or di-(N-succinimidyl)-carbonate, in a dry aprotic solvent such as DCM, MeCN or DMF between −20° C. and +60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° C. and +60° C. Further activating agents can be found in *Comprehensive Organic Transformations. A guide to Functional Group Preparations; $2^{nd}$ Edition*, R. C. Larock, Wiley-VC; New York, Chichester, Weinheim, Brisbane, Singapore, Toronto, 1999. Section nitriles, carboxylic acids and derivatives p. 1941-1949.

General Reaction Technique 10: Cis-Dihydroxylation:

The diol is obtained by dihydroxylation of the corresponding ethylenic derivative using a catalytic amount of osmium tetroxide in the presence a co-oxidant such as NMO in aq. solvent such as an acetone-water or DCM-water mixture (see Cha, J. K. *Chem. Rev.* (1995), 95, 1761-1795). The chiral cis-diols are obtained by using AD-mix α or AD-mix β in presence of methanesulfonamide in a water/2-methyl-2 propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.

General Reaction Technique 11: Amino Deprotection:

The benzyl carbamates are deprotected by hydrogenolysis over a noble catalyst (e.g. Pd/C or Pd(OH)$_2$/C). The Boc group is removed under acidic conditions such as HCl in an org. solvent such as MeOH or dioxane, or TFA neat or diluted in a solvent such as DCM. Further general methods to remove amine protecting groups have been described in *Protecting Groups in Organic Synthesis, $3^{rd}$ Ed* (1999), 494-653; T. W. Greene, P. G. M. Wuts (Publisher: John Wiley and Sons, Inc., New York, N.Y.).

General Reaction Technique 12: Ketal Deprotection:

The ketal is converted into its corresponding ketone under acidic conditions such as diluted aq. HCl in MeOH, diluted aq. AcOH or by using an acidic resin such as Amberlite IR120H or DOWEX 50W8 in a water-solvent mixture such as MeOH/water or THF/water between 20° C. and 80° C.

General Reaction Technique 13: Oxidation of Alcohols into Acids:

Alcohols can be directly oxydized into their corresponding acids by a variety of methods as described in *Comprehensive Organic Transformations. A guide to Functional Group Preparations; $2^{nd}$ Edition*, R. C. Larock, Wiley-VC; New York, Chichester, Weinheim, Brisbane, Singapore, Toronto, 1999. Section nitriles, carboxylic acids and derivatives p. 1646-1648. Among them, [bis(acetoxy)iodo]benzene in presence of TEMPO, the Jones reagents (CrO$_3$/H$_2$SO$_4$), NaIO$_4$ in presence of RuCl$_3$, KMnO$_4$ or pyridine H$_2$Cr$_2$O$_7$ are frequently used.

General Reaction Technique 14: Formation of Alkene Through Wittig or Julia Coupling:

Wittig Reaction:

The alkene R$^a$CH=CHR$^b$ can be obtained by reacting an aldehyde R$^a$CHO with a phosphorane Ph$_3$P=CHR$^b$. The reaction is performed in a large variety of solvent such as toluene or THF at a temperature ranging between −10° C. and 100° C. The required phosphorane is formed from the corresponding phosphonium halogenide Ph$_3$P$^+$CH$_2$R$^b$Hal$^-$ (Hal being a halogen atom) in presence of a base such as potassium alkylate (e.g. tBuOK), LiRMDS, KHMDS or nBuLi. The phosphonium salt is obtained from the corresponding halogenide HalCH$_2$R$^b$ and PPh$_3$ in a refluxing solvent such as toluene or MeCN.

Julia Coupling:

The alkene R$^a$CH=CHR$^b$ can also be obtained using a Julia coupling reaction between a sulfone R$^b$CH$_2$SO$_2$R$^c$ and an aldehyde R$^a$CHO in presence of a base such as LiHMDS or KHMDS in a solvent such as 1,2-DME, DMF or toluene as reviewed by Blakemore, P. R in *J. Chem. Soc., Perkin Trans.* 1 (2002), 2563-2585. The required sulfone is obtained from the corresponding sulphide R$^b$CH$_2$SR$^c$ via an oxidation reaction. A wide range of oxidizing agents may be used to perform such a reaction, such as mCPBA in a solvent such as DCM, Oxone® in a solvent such as aq. MeOH (see *Tetrahedron Lett.* (1981), 22, 1287), or aq. hydrogen peroxide in presence of ammonium heptamolybdate tetrahydrate in EtOH (see *J. Org. Chem.* (1963), 28, 1140). The sulphide is obtained from the corresponding alcohol R$^b$CH$_2$OH via a Mitsunobu coupling reaction. An alternate route to form the intermediate sulphide requires the activation of the alcohol R$^b$CH$_2$OH as an iodide following general reaction technique 8. The latter serves as an alkylating agent of the 1-phenyl-1H-tetrazole-5-thiol. The alkylation reaction is performed in presence of an inorganic base such as KOH or NaOH in a solvent such as EtOH at a temperature ranging between −20° C. and 70° C. The alkene R$^a$R$^{a'}$C=CHR$^b$ can be obtained by reacting a ketone R$^a$COR$^{a'}$ with a phosphorane Ph$_3$P=CHR$^b$ as described above.

General Reaction Technique 15: Hydrolysis of an Ester into a Carboxylic Acid:

When the ester side chain is a linear alkyl, the hydrolysis is usually performed by treatment with an alkali hydroxide such as LiOH, KOH or NaOH in a water-dioxane or water-THF mixture between 0° C. and +80° C. When the ester side chain is tBu, the hydrolysis can also be performed in neat TFA or diluted TFA or HCl in an org. solvent such as ether or THF. When the ester side chain is the allyl group, the reaction is performed in presence of tetrakis(triphenylphosphine)palladium(0) in presence of an allyl cation scavenger such as morpholine, dimedone or tributyltin hydride between 0° C. and +50° C. in a solvent such as THF. When the ester side chain is benzyl, the reaction is performed under hydrogen in presence of a noble metal catalyst such as Pd/C in a solvent such as MeOH, THF or EA. Further strategies to introduce other acid protecting groups and general methods to remove them have been described in *Protecting Groups in Organic Synthesis, $3^{rd}$ Ed* (1999), 369-441; T. W. Greene, P. G. M. Wuts (Publisher: John Wiley and Sons, Inc., New York, N.Y.).

General Reaction Technique 16: Reduction of Ketones and Aldehydes into Their Corresponding Alcohols:

The aldehydes and ketones can be reduced to the corresponding alcohols using a variety of reducing agents as reviewed by Larock, R. C. in *Comprehensive Organic Transformations A guide to Functional Group Preparations, $2^{nd}$ Ed.*, Wiley, New York, Chichester, Weinheim, Brisbane, Singapore, Toronto (1999), Section Alcohols and phenols; p. 1075 to 1110. Among them LiAlH$_4$ and NaBH$_4$ are the most preferred.

General Reaction Technique 17: Reduction of an Ester into its Corresponding Alcohol:

An ester can be reduced into its corresponding alcohol using a variety of reducing agents as reviewed by Larock, R. C. in *Comprehensive Organic Transformations A guide to Functional Group Preparations, $2^{nd}$ Ed.*, Wiley, New York, Chichester, Weinheim, Brisbane, Singapore, Toronto (1999), Section Alcohols and phenols; p. 1114 to 1120. Among them LiAlH$_4$ or DIBAH are the most preferred.

General Reaction Technique 18: Reductive Amination:

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, DCM or DCE or mixture of solvents such as MeOH-DCE. The reaction can be catalyzed by traces of acid (usually AcOH). The intermediate imine is reduced with a suitable reducing agent (e.g. NaBH$_4$, NaBH$_3$CN, or NaBH(OAc)$_3$ or through hydrogenation over a noble catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (Tetrahedron (2004), 60, 7899-7906).

General Preparation Methods:

Preparation of Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to p) hereafter describe general methods for preparing compounds of formula I. The preparation of elaborated intermediates and basic building blocks is described thereafter. General synthetic methods used repeatedly throughout the schemes below are referenced to and described in the above section entitled "General reaction techniques". If not indicated otherwise, the generic groups or integers U, V, W, X, R$^1$, R$^2$, R$^3$, A, K, G, m and n are as defined for formula I.

a) The compounds of formula I can be obtained by reacting a compound of formula II

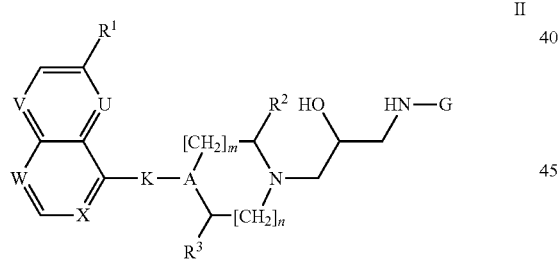

with a carbonic acid derivative of formula III

wherein L$^0$ and L$^{00}$ both represent chloro, OCCl$_3$, imidazolyl or succinimidyloxy, or L$^0$ represents chloro and L$^{00}$ represents OCCl$_3$. This reaction is preferably carried out in a dry aprotic solvent such as DCM or THF in presence of an org. base such as TEA or pyridine and at a temperature range between −30° C. and +80° C. In case there is one or more free alcohol or amino functions on A, K, R$^2$ or R$^3$, these functional groups are protected (see general reaction techniques 1 and 2) prior to the reaction and the protecting groups are removed thereafter (see general reaction techniques 3 and 11).

b) The compounds of formula I can also be obtained by reacting a compound of formula IV

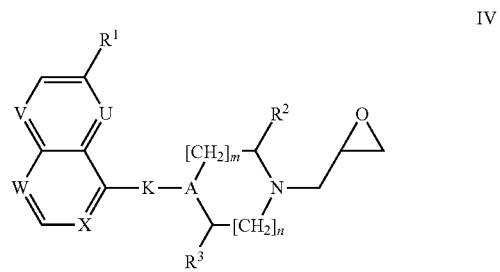

with the anion of a compound of formula V

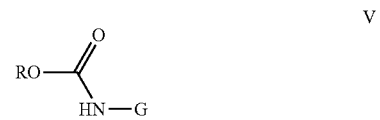

wherein R represents alkyl or benzyl. This reaction is performed following general reaction technique 4.

c) The compounds of formula I wherein A is CH and K is O or OCH$_2$ can be obtained by reacting a compound of formula VI

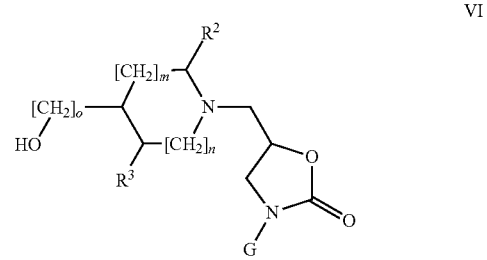

wherein o represents 0 or 1 with a compound of formula VII

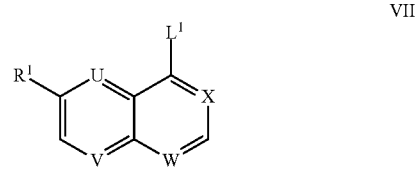

wherein L$^1$ represents chlorine, bromine or OTf, in a solvent such as dioxane, NMP or DMF between about +20° C. and about +120° C., optionally in presence of a catalyst as described in general reaction technique 5 or wherein L$^1$ represents OH under Mitsunobu conditions following general reaction technique 6.

d) The compounds of formula I wherein A is CH and K is NHCO can be obtained by reacting a compound of formula VIII

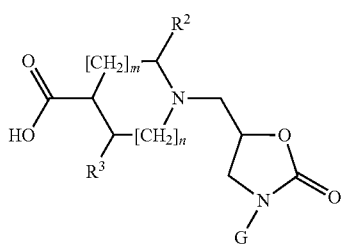

VIII with a compound of formula VIIa

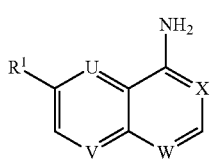

VIIa following general reaction technique 9.

Alternatively, the compounds of formula I wherein A is CH and K is NHCO can also be obtained by reacting the carboxamides derived from the carboxylic acids of formula VIII with the compounds of formula VII wherein $L^1$ represents OTf following general reaction technique 5.

e) The compounds of formula I can furthermore be obtained by coupling a compound of formula IX

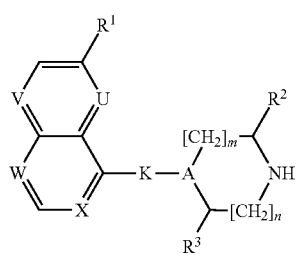

IX with a compound of formula X

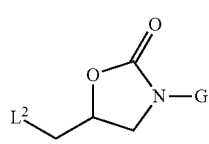

X wherein $L^2$ represents OMs, OTf, OTs, chloro, bromo or iodo following general reaction technique 7.

f) The compounds of formula I wherein A is CH and K is CH=CH can be obtained by reacting a compound of formula XI

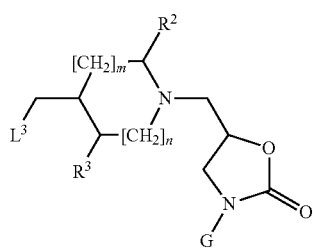

XI wherein $L^3$ represents $P^-Ph_3Hal^-$ or $SO_2R^d$, wherein $R^d$ is 1-phenyl-1H-tetrazol-5-yl or benzothiazol-2-yl and Hal represents a halogen, with a compound of formula XII

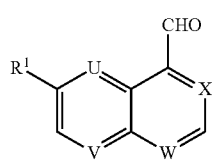

XII in a solvent such as toluene, dioxane or THF between about −20° C. and about +120° C., in presence of a base as described in general reaction technique 14.

g) The compounds of formula I wherein KA is CH=C can be obtained by reacting a compound of formula XIII

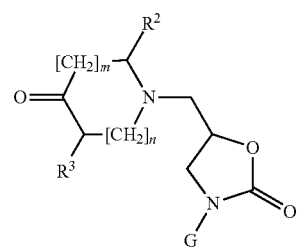

XIII with a compound of formula XIV

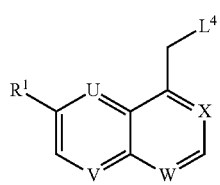

XIV wherein $L^4$ is $P^+Ph_3Hal^-$, Hal representing a halogen, in a solvent such as toluene, dioxane or THF between about −20° C. and about +120° C., in presence of a base as described in general reaction technique 14.

h) The compounds of formula I can moreover be obtained by reacting a compound of formula XV

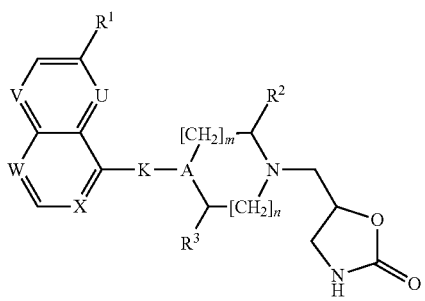

XV with a compound of formula $L^5$-G, wherein $L^5$ represents OTf or halogen such as bromine or iodine. This reaction is performed following general reaction technique 5. In case the group G is such that Z is N, the reaction is performed in presence of NaH.

i) The compounds of formula I wherein A is CH and K is $CH_2CH_2$ can be obtained by hydrogenation of the corresponding compounds of formula I wherein K is CH=CH over a noble metal catalyst such as Pd/C.

j) The compounds of formula I wherein A is CH and K is CH(OH)CH(OH) can be obtained by cis-dihydroxylation of the corresponding compounds of formula I wherein K is CH=CH following general reaction technique 10.

k) The compounds of formula I wherein A is CHOH and K is CH(OH) can be obtained by cis-dihydroxylation of the corresponding compounds of formula I wherein K represents $CHR^5$, A represents $CR^4$ and $R^4$ together with $R^5$ forms a bond (i.e. K-A represents CH=C) following general reaction technique 10.

l) The compounds of formula I wherein K is NH or $NHCH_2$ can be obtained from the amines of formula XIa

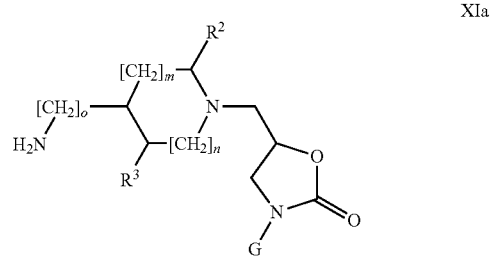

XIa wherein o is 0 or 1, with compounds of formula VII wherein $L^1$ is OTf following general reaction technique 7.

m) The compounds of formula I wherein $R^3$ is $NH_2$ or $R^2$ is $CH_2NH_2$ can be obtained from the corresponding derivatives of formula I wherein $R^3$ is $N_3$ or $R^2$ is $CH_2N_3$ by reaction with $PPh_3$ in presence of water.

n) The compounds of formula I wherein $R^3$ is $NHCOR^6$ are obtained from the corresponding compounds of formula I wherein $R^3$ is $NH_2$ after reaction with a compound of formula $R^6COZ$ wherein Z represents OH or halogen following general reaction technique 9.

o) The compounds of formula I wherein $R^3$ is triazol-1-yl or $R^2$ is triazol-1-ylmethyl can be obtained from the corresponding derivatives of formula I wherein $R^3$ is $N_3$ or $R^2$ is $CH_2N_3$ by reaction with acetylene or bicyclo[2.2.1]hepta-2,5-diene.

p) The compounds of formula I wherein K is $CH_2NH$ and A is CH can be obtained by reductive amination of the amines of formula XIa wherein o is 0 with the aldehydes of formula XII following general reaction technique 18.

The compounds of formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

Preparation of the Compounds of Formulae II and IV:

The compounds of formulae II and IV can be obtained as summarised in Scheme 1 hereafter.

Scheme 1

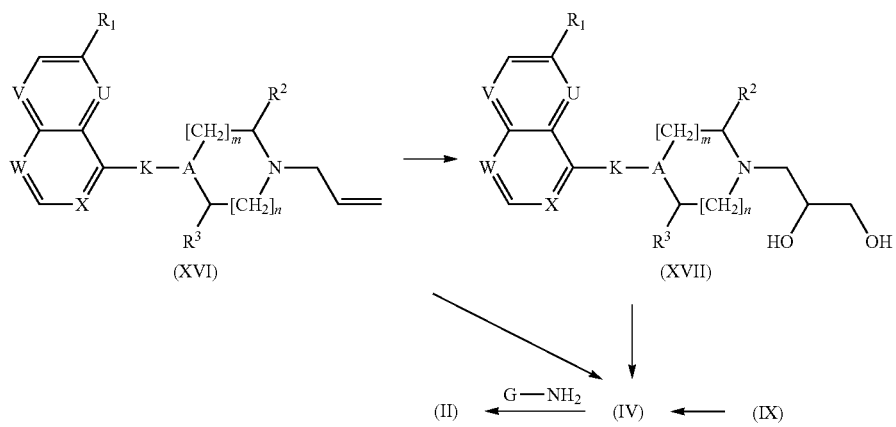

The allyl derivatives of formula XVI can be transformed (Scheme 1) into the corresponding epoxides of formula IV either through direct epoxidation of the terminal double bond or via cis-dihydroxylation with OsO$_4$/NMO following (general reaction technique 10), or as described by V. Van Rheenen et al. in *Tetrahedron Lett.* (1976), 23, 1973-76, followed by conversion into the corresponding epoxides after mesylation, or tosylation, and ring closure under basic conditions such as TEA. In case chiral epoxides are required, they can be obtained by hydrolytic kinetic resolution (HKR) catalyzed by chiral (salen)-Co(III) complex (e.g. [(R,R)—N,N'-bis(3,5-di-tert-butylsalicylidene)-1,2-cyclohexanediaminato(2-)]cobalt(III) of the racemic mixture of epoxides as described by Jacobsen et al. in *J. Am. Chem. Soc.* (2002), 124, 1307-1315 and *Science* (1997), 277, 936-938. Alternatively, the chiral epoxides can also be obtained from the allylic derivatives of formula XVI through either Shi chiral epoxidation using a chiral ketone as described *Acc. Chem Res.* (2004), 37, 488-496 or through chiral cis-dihydroxylation using AD mixtures using general reaction technique 10 followed by formation of the mesylate of the primary alcohol using general reaction technique 8 and epoxide formation under basic conditions.

The epoxides of formula IV can also be obtained (Scheme 1) by reacting the amines of formula IX with epichlorhydrin, or optionally with one of the two enantiomers of epichlorhydrin, optionally in presence of MgSO$_4$, followed by epoxide formation after treatment with a base such as tBuOK in DMF.

The epoxides of formula IV can then be reacted with the amines of formula G-NH$_2$, affording compounds of formula II.

In case an aromatic N-oxide or a tertiary amine N-oxide is formed during an oxidation step it can be reduced to the corresponding naphthyridine, quinoline or quinazoline or to the corresponding tertiary amine by deoxygenation with Zn dust in acidic media and acetic formic anhydride respectively as described in *Bioorg. Med. Chem. Lett.* (2007), (17), 3322-3329 and *Chemistry Letters* (1985), 10, 1517-1520.

Preparation of the Compounds of Formula V:

The carbamates of formula V can be prepared from the corresponding (usually commercially available) amines of formula G-NH$_2$ following general reaction technique 1.

Preparation of the Compounds of Formulae VI and VIII:

The compounds of formulae VI and VIII can be obtained as summarised in Scheme 2 hereafter.

Scheme 2

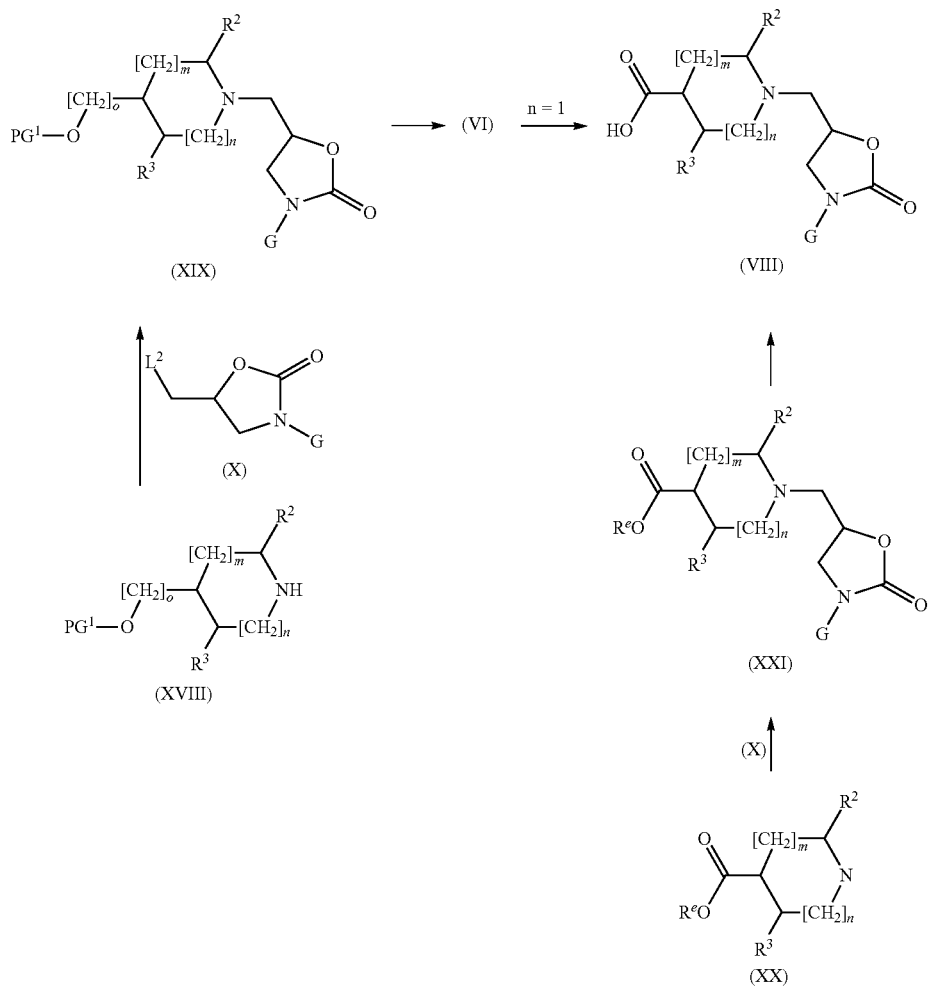

In Scheme 2, $PG^1$ represents a silyl protecting group such as TBDMS or TBDPS, $R^e$ represents an alkyl group such as methyl or ethyl or a benzyl group.

The amines of formula XVIII can be reacted (Scheme 2) with the derivatives of formula X wherein $L^2$ represents OMs, OTf, OTs, chloro, bromo or iodo following general reaction technique 7. The compounds of formula VI are obtained by deprotection of intermediate of formula XIX following general reaction technique 3.

The compounds of formula VIII can be obtained by ester hydrolysis of intermediates of formula XXI following general reaction technique 15. They can also be obtained by oxidation of the compounds of formula VI wherein n=1 using general reaction technique 13. The compounds of formula XXI are obtained from intermediates of formulae XX and X (wherein $L^2$ represents OMs, OTf, OTs, chloro, bromo or iodo) using general reaction technique 7.

Preparation of the Compounds of Formula VII:

The required quinoline, [1,5]-naphthyridine, quinazoline and quinoxaline derivatives of formula VII wherein $L^1$ represents Br are either commercially available or can be prepared following literature procedures. For example, compounds wherein $L^1$=Br, W=N and X=V=U=CH are prepared according to WO 2003/087098, compounds wherein $L^1$=Br, W=V=N and X=U=CH are prepared according to WO 2006/032466, compounds wherein $L^1$=Br, X=N and U=V=W=CH or wherein $L^1$=Cl, W=N and X=V=U=CH are prepared according to WO 2004/089947, and compounds wherein $L^1$=Cl, V=N and X=W=U=CH are prepared according to WO 2005/019215.

The compounds of formula VII wherein $L^1$=Br can be prepared from the compounds of formula VIIb

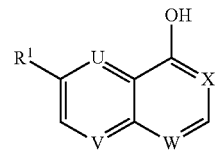

by reaction with $PBr_3$ in DMF at a temperature of about 40° C.

The compounds of formula VII wherein $L^1$=OTf can be prepared from the compounds of formula VIIb as defined above by reaction with $Tf_2O$ (using general reaction technique 8) or N,N-bis(trifluoromethanesulfonyl)aniline in presence of TEA.

Preparation of the Compounds of Formula VIIa:

The compounds of formula VIIa can be obtained by reaction of the corresponding compounds of formula VII wherein $L^1$ represents OTf with ammonia in a solvent like DCM or THF, or with n-propylamine hydrochloride in pyridine between −20° C. and 100° C. (R. Radinov, *Synthesis* (1986), 886). The 4-amino-quinazoline derivatives of formula VIIa can also be obtained from the corresponding compounds of formula VII wherein $L^1$ represents chlorine by reaction with ammonia under the same conditions.

Preparation of the Compounds of Formula VIIb:

The compounds of formula VIIb are commercially available or can be prepared according to routes described in WO 2006/32466 (V=N and X=U=W=CH) or WO 2004/02490 (U=V=N and X=W=CH).

Preparation of the Compounds of Formula IX:

The compounds of formula IX can be obtained as summarised in Scheme 3 hereafter.

Scheme 3

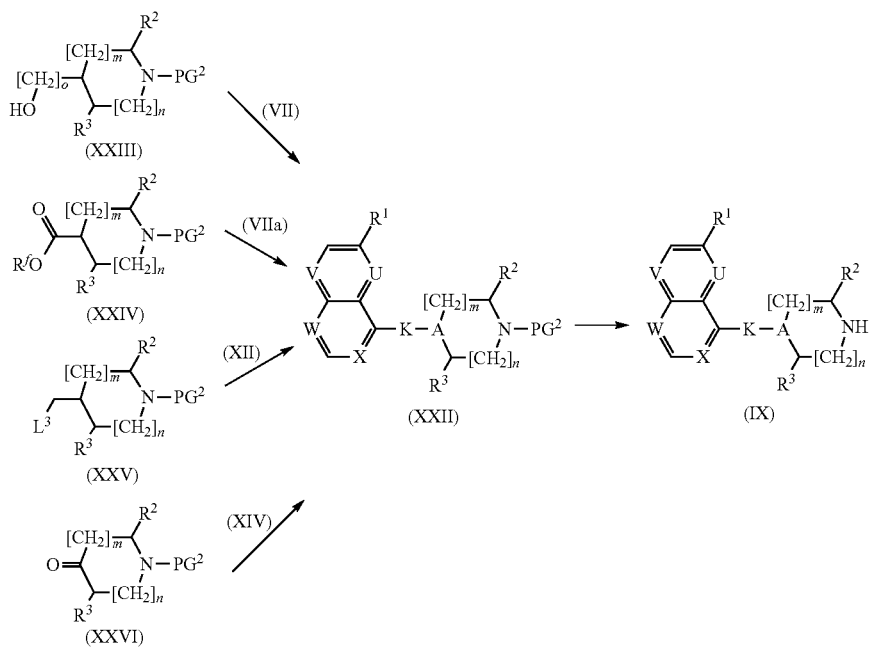

In Scheme 3, $PG^2$ represents an amino protecting group such as Cbz or Boc.

The compounds of formula IX can be obtained (Scheme 3) by deprotection of the compounds of formula XXII following general reaction technique 11.

The compounds of formula XXII wherein K is $O(CH_2)_n$ and n is 0 or 1 can be obtained (Scheme 3) by reacting derivatives of formula VII wherein $L^1$ represents bromine or OTf with the alcohols of formula XXIII wherein n is 0 or 1, as described in section c) of "Preparation of compounds of formula I".

The compounds of formula XXII wherein K is NHCO can be obtained (Scheme 3) by reacting the amino derivatives of formula VIIa with the acids of formula XXIV wherein $R^f$ is H, as described in "Preparation of compounds of formula I", section d).

The compounds of formula XXII wherein K is CH=CH can be obtained (Scheme 3) by reacting the aldehydes of formula XII with compounds of formula XXV wherein $L^3$ represents $P^+Ph_3Hal^-$ or $SO_2R^d$, wherein $R^d$ is 1-phenyl-1H-tetrazol-5-yl or benzothiazol-2-yl, Hal represents a halogen atom, as described in "Preparation of compounds of formula I", section f).

The compounds of formula XXII wherein K-A is CH=C (i.e. wherein K represents $CHR^5$, A represents $CR^4$ and $R^4$ together with $R^5$ forms a bond) can be obtained (Scheme 3) by reacting the ketone derivatives of formula XXVI with the compounds of formula XIV wherein $L^4$ represents $P^+Ph_3Hal^-$, wherein Hal represents a halogen, as described in "Preparation of compounds of formula I", section g).

The compounds of formula XXII wherein K is $CH_2CH_2$ can be obtained by hydrogenation of derivatives of formula XXII wherein K is CH=CH as described in "Preparation of compounds of formula I", section i). In the particular case wherein $PG^2$ is Cbz, compounds of formula IX wherein K is $CH_2CH_2$ are however obtained directly.

Moreover, the compounds of formula XXII wherein KA is CHOHC(OH) can be obtained by cis-hydroxylation of derivatives of formula XXII wherein KA is CH=C as described in "Preparation of compounds of formula I", section k).

Preparation of the Compounds of Formula X:

The compounds of formula X can be obtained either by opening glycidyl tert-butyldimethylsilyl ether with the amines of formula $G-NH_2$ followed by oxazolidinone formation following the method described in section a) of "Preparation of compounds of formula I", and removal of the TBDMS protecting group following general reaction technique 3, or from the carbamates of formula V and glycidyl butyrate following general reaction technique 4, which reaction is followed by conversion of the hydroxy group into a OMs, OTf, OTs, chloro, bromo or iodo group using methods described under general reaction technique 8.

Preparation of the Compounds of Formula XI:

The compounds of formula XI wherein $L^3$ is $PPh_3^-Hal^-$ are obtained from compounds of formula VI wherein o=1 after transformation of the alcohol function into its corresponding mesylate and halogenide following general reaction technique 8 and reaction with $PPh_3$. The compounds of formula XI wherein $L^3$ is $SO_2R^d$ are obtained from the alcohol of formula VI wherein o=1 following general reaction technique 14, section Julia coupling.

Preparation of the Compounds of Formula XIa:

The compounds of formula XIa are obtained by transformation of the compounds of formula VI into their corresponding mesylates using general reaction technique 8 followed by reaction with sodium azide and reduction of the azide group into its corresponding amine with $PPh_3$ and water.

Preparation of the Compounds of Formula XII:

The required quinoline, [1,5]-naphthyridine, quinoxaline and quinazoline derivatives of formula XII wherein $R^1$ is OMe are either commercially available or can be prepared following literature procedures. For example, compounds wherein U=W=N and X=V=CH are prepared according to WO 2006/032466, compounds wherein V=N and W=X=U=CH are prepared according to WO 2006/032466, compounds wherein U=V=N and W=X=CH are prepared according to WO 2006/021448 and compounds wherein U=N and V=W=X=CH are prepared according to WO 2006/046552.

Preparation of the Compounds of Formula XIII:

The compounds of formula XIII wherein $R^3$ is H can be obtained as summarised in Scheme 4 hereafter.

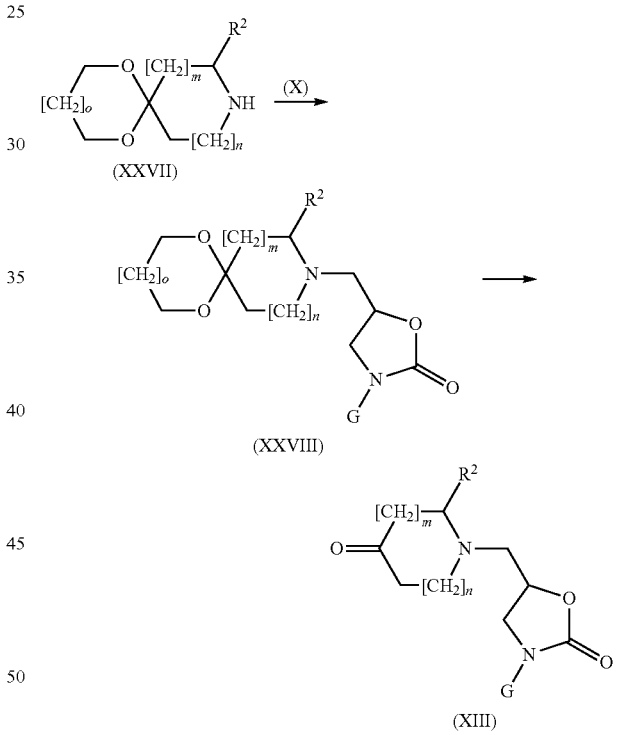

Scheme 4

In Scheme 4, o represents 0 or 1.

The compounds of formula XIII can be obtained (Scheme 4) by acidic deprotection of the ketal function of compounds of formula XXVIII following general reaction technique 12. The compounds of formula XXVIII are obtained from compounds of formulae XXVII and X using general reaction technique 7.

Preparation of the Compounds of Formula XIV:

The required quinoline, [1,5]-naphthyridine, quinoxaline and quinazoline derivatives of formula XIV wherein $R^1$ is OMe and $L^4$ is $P^+PH_3Hal^-$ can be obtained as summarised in Scheme 5 hereafter.

Scheme 5

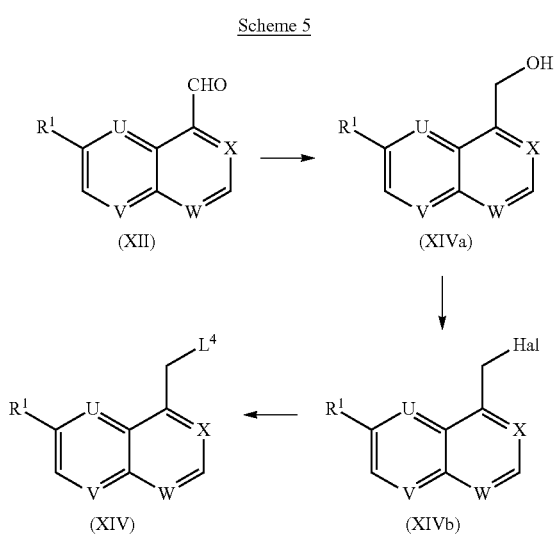

The compounds of formula XII can be reduced (Scheme 5) into the alcohols of formula XIVa (general reaction technique 16) which can be converted into the corresponding compounds of formula XIVb wherein Hal is halogen (e.g., when Hal is bromine, by reaction with PBr$_3$). The compounds of formula XIV can then be obtained by reaction of the compounds of formula XIVb with PPh$_3$.

Preparation of the Compounds of Formula XV:

The intermediates of formula XV can be obtained by reacting the epoxides of formula IV with sodium azide followed by hydrogenation over a noble metal catalyst such as Pd/C and either reaction with CDI or subsequent transformation into its corresponding carbamate with CbzCl or Boc$_2$O. The oxazolidinone ring is then formed by subsequent reaction with NaH. They can also be obtained by reacting the compounds of formula IX with benzyl oxiran-2-ylmethylcarbamate or one of its enantiomers following general reaction technique 4 before treating with NaH.

Preparation of Starting Compounds:

The compounds of formula XVI can be obtained by alkylation of the compounds of formula IX with allylbromide in presence of a base such as TEA.

The compounds of formula XVIII can be obtained by protection of the alcohols of formula XXIII following general reaction technique 2 followed by removal of the amine protecting group following general reaction technique 11.

The compounds of formula XX can be obtained by deprotection of compounds of formula XXIV following general reaction technique 11. The compounds of formula XXIV wherein R$^f$ is methyl can be obtained by esterification of the carboxylic acids of formula XXIV wherein R$^f$ is H, e.g. esterification with diazomethane or TMS diazomethane.

The compounds of formula XXIII wherein o=0 can be obtained by reduction of the ketone function of derivatives of formula XXVI following general reaction technique 16. The compounds of formula XXIII wherein o=1 can be obtained by reduction of the ester function of the compounds of formula XXIV wherein R$^f$ is methyl following general reaction technique 17. The compounds of formula XXIII wherein o=0, m=n=1, R$^3$=H and R$^2$ is CH$_2$N$_3$ can be obtained from the corresponding 4-[[(1,1-dimethylethyl) dimethyl silyl]oxy]-2-(hydroxymethyl)-1-piperidinecarboxylic acid tert-butyl ester prepared as described in WO 2007/122103 after transformation into their corresponding mesylates (following general reaction technique 8 and reaction with sodium azide) and removal of the Boc protecting group as described in general reaction technique 11. The compounds of formula XXIII wherein o=0, m=n=1, R$^2$=H and R$^3$ is NH$_2$ can be obtained by reduction of the corresponding tert-butyl 3-azido-4-hydroxy-1-piperidine carboxylates (prepared according to WO 02/096426) using the abovementioned method followed by further removal of the Boc protecting group as described in general reaction technique 11. The compounds of formula XXIII wherein o=1, m=n=1, R$^2$=H and R$^3$ is NH$_2$ can be prepared according to WO 01/81347.

The carboxylic acids of formula XXIV wherein R$^f$ is H, R$^2$ is H, R$^3$ is H, PG$^2$ is Cbz and m=n=0, or m=n=1 or m=1 and n=0 are commercially available. The other carboxylic acids of formula XXIV can be prepared as summarised in Scheme 6 hereafter.

Scheme 6

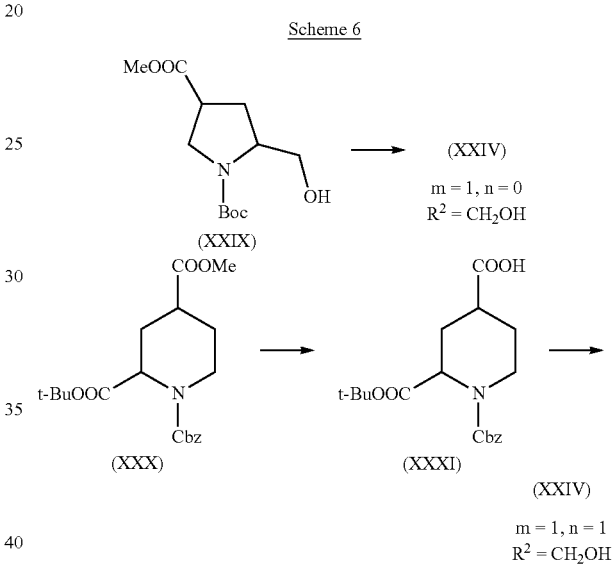

The carboxylic acids of formula XXIV wherein R$^f$ is H, m=n=1 or m=1 and n=0, R$^2$ is CH$_2$OH and R$^3$ is H can be prepared (Scheme 6) from the corresponding esters of formula XXIX or XXX described in EP 334 244 and Tetrahedron (1995), 51(31), 8545-54 respectively, using standard procedures (ester hydrolysis following general reaction technique 15 and ester hydrolysis followed by ester reduction as described in general reaction technique 17).

The precursors of the compounds of formula XXV, i.e. the compounds of formula XXV wherein L$^3$ would be OMs, OTs or halogen such as iodine can be obtained from the alcohols of formula XXIII wherein o=1 following general reaction technique 8. The compounds of formula XXV wherein L$^3$ is PPh$_3^+$Hal$^-$ are obtained by reacting said precursors (L$^3$ being halogen) with PPh$_3$. The compounds of formula XXV wherein L$^3$ is SO$_2$R$^d$ can be obtained from said precursors following general reaction technique 14, section Julia coupling.

The ketones of formula XXVI wherein R$^2$ is H, PG$^2$ is Cbz and m=n=0, or m=n=1 or m=1 and n=0 are commercially available. The ketones of formula XXVI wherein m=n=1 or m=1 and n=0, and R$^2$ is CH$_2$OH can be prepared from the commercially available corresponding esters (R$^2$=COOalkyl) by reduction following general reaction technique 17.

The compounds of formula XXVII can be obtained by protection of the ketone function of compounds of formula XXVI with ethanediol or 1,3-propanediol in presence of p-TsOH, followed by removal of the amino protecting group as described in general reaction technique 11.

Particular embodiments of the invention are described in the following Examples, which serve to illustrate the invention in more detail without limiting its scope in any way.

EXAMPLES

General Methods

Method A: Boc Deprotection

The Boc-protected amine (1 mmol) was dissolved in DCM (2 mL). Et$_3$SiH (1.05 mmol) (optional) and TFA (2 mL) were added. The mixture was stirred at rt for 1 h, concentrated in vacuo and taken up in DCM/NH$_4$OH. The org. layer was washed with water, dried over MgSO$_4$ and concentrated under reduced pressure.

Method B: Alkylation of Amines with Iodides and Mesylates

A solution of the amine (1 mmol, in the case of iodides; 1-2 mmol in the case of mesylates), mesylate/iodide (1 mmol) and DIPEA (1.1 mmol) in dry DMSO was heated to 70° C. until completion of the reaction (1-3 days). After cooling to rt water and EA were added and the phases were separated. The aq. layer was extracted two more times with EA and the combined org. layers were washed with water (3×) and brine, dried over MgSO$_4$ and concentrated under reduced pressure. The residue was purified by CC.

Method C: Nucleophilic Aromatic Substitution of 4-chloro-6-methoxy-quinazoline

To a solution of the hydroxy compound (1 mmol) and 4-chloro-6-methoxy-quinazoline (1 mmol) in NMP (2 mL) at 0° C. was added NaH (1 mmol, 60% in mineral oil). The mixture was stirred at 0° C. until completion of the reaction (usually 1-4 h), quenched with water and extracted with EA. The combined org. layers were washed several times with water and brine, dried over MgSO$_4$ and concentrated under reduced pressure. The residue was purified by CC.

Method D: Amide Coupling with HATU

To a solution of DIPEA (4 mmol) and of the amine (1 mmol) and the acid (1 mmol) to be coupled in DMF (2 mL) was added HATU (2 mmol) at rt. The resulting mixture was stirred at rt until completion of the reaction. Water and EA were added, the phases were separated and the aq. phase was extracted with EA. The combined org. layers were washed several times with water and brine, dried over MgSO$_4$ and concentrated under reduced pressure. The residue was purified by CC.

Method E: Nucleophilic Aromatic Substitution:

A mixture of the aryl halide or the aryl triflate (1 mmol), the amine (1 mmol) and DIPEA (1.2 mmol) in NMP (4 mL) was heated at 70-80° C. until completion of the reaction. Water was added and the mixture was extracted with EA. The combined org. layers were washed with water (3×), brine, dried over MgSO$_4$ and concentrated under reduced pressure. The residue was purified by CC.

Method F: Buchwald Coupling

An oven-dried vial was charged with the aryl bromide or aryl chloride (1 mmol), palladium(II)acetate (0.04 mmol), BINAP (0.08 mmol) or bis((2-diphenylphosphino)phenyl) ether (0.08 mmol), K$_3$PO$_4$ (2.5 mmol) and amine (1 mmol). The resulting mixture was purged with argon for several min. Dioxane (1 mL) was then added via a syringe and the resulting suspension was purged with argon for 3 min. The mixture was then heated at 85° C. until completion of the reaction. The solvent was removed under reduced pressure and the residue was extracted with EA/water. The org. layer was washed with brine, dried over MgSO$_4$ and concentrated under reduced pressure. The residue was purified by CC.

Method G: Hydrogenation of Cbz-Group

A suspension of the benzyl carbamate (1 mmol) in MeOH (6 mL) was hydrogenated over 5 or 10% Pd/C (200 mg) for 2 h. The catalyst was filtered and the filter cake was washed thoroughly with MeOH and DCM. The filtrate was concentrated under reduced pressure.

Method H: Reductive Amination:

A solution of primary amine (1 mmol) and aldehyde or ketone (1 mmol) in DCE/MeOH 1:1 (10 mL) is stirred at rt overnight. NaBH$_4$ (2-5 eq) is added and the reaction allowed to proceed for another hour. The reaction is diluted with DCM and aq. NH$_4$OH. The org. phase is washed with water, dried over MgSO$_4$ and concentrated.

Preparations:

Preparation A: methanesulfonic acid (S)-2-oxo-3-(3-oxo-3,4-dihydro-2H-benzo[1,4]thiazin-6-yl)-oxazolidin-5-ylmethyl ester A.i. 6-[(S)-3-(tert-butyl-dimethyl-silanyloxy)-2-hydroxy-propylamino]-4H-benzo[1,4]thiazin-3-one To a solution of tert-butyl-dimethyl-((S)-1-oxiranylmethoxy)-silane (13.0 g, 69 mmol) in acetonitrile (220 mL) was added LiClO$_4$ (22 g, 207 mmol). 6-amino-4H-benzo[1,4]thiazin-3-one (11.4 g, 64 mmol) was added and the mixture was stirred at 50° C. for 6 h. The solvent was removed in vacuo and the residue was chromatographed (DCM/MeOH/NH$_4$OH 1000/25/2→1000/100/2) to afford the title compound as a pale brown foam (11.16 g, 44% yield).

MS (ESI, m/z): 369.3 [M+H$^+$].

A.ii. 6-[(S)-5-(tert-butyl-dimethyl-silanyloxymethyl)-2-oxo-oxazolidin-3-yl]-4H-benzo[1,4]thiazin-3-one A solution of intermediate A.i (11.60 g, 30 mmol) and CDI (5.57 g, 33 mmol) in THF (130 mL) was heated at 50° C. for 2 h, the mixture was concentrated in vacuo and partitioned between EA and water. Some crystallized product was filtered and washed with H$_2$O and EA to give 5.21 g of product. The org. layer was washed with brine, dried over MgSO$_4$ and concentrated. The residue was purified by CC (DCM/MeOH/NH$_4$OH 1000:50:4) to give additional 2.28 g of product (overall 7.49 g of an off-white solid, 63% yield).

MS (ESI, m/z): 395.1 [M+H$^+$].

A.iii. 6-((S)-5-hydroxymethyl-2-oxo-oxazolidin-3-yl)-4H-benzo[1,4]thiazin-3-one

A suspension of intermediate A.ii (11.49 g, 29.1 mmol) in THF (29 mL) was treated with TBAF (1M in THF, 29.1 mL). The yellow solution was stirred at 0° C. for 3 h and then partitioned between water and EA. Some crystallized product was filtered and washed with H$_2$O and EA to give 6.49 g of product. The aq. phase was extracted with EA (3×). The combined org. layers were washed with brine, dried over MgSO$_4$, filtered and concentrated. The crude product was triturated with EA to give further 1.23 g of product (overall 7.72 g of an off-white solid, 95% yield).

MS (ESI, m/z): 281.3 [M+H$^+$].

A.iv. Methanesulfonic acid (S)-2-oxo-3-(3-oxo-3,4-dihydro-2H-benzo[1,4]thiazin-6-yl)-oxazolidin-5-ylmethyl ester A solution of intermediate A.iii (2.77 g, 9.88 mmol) in anhydrous DCM (100 mL) and DIPEA (4.7 mL, 28.2 mmol) was cooled to 0° C. and MsCl (1.07 mL, 13.8 mmol) was added dropwise. The resulting mixture was stirred at 0° C. for 1 h. Water was added and the mixture was extracted with DCM and the combined org. layers were washed with water. The yellow residue was triturated with EA/DCM/ether to afford the title compound as a colourless solid (2.45 g, 69% yield).
$^1$H NMR (DMSO-d6) δ: 10.57 (s, 1H), 7.31 (m, 2H), 7.10 (dd, J=8.5, 2.3 Hz, 1H), 4.98 (m, 1H), 4.48 (m, 2H), 4.13 (t, J=9.4 Hz, 1H), 3.75 (dd, J=9.4, 6.4 Hz, 1H), 3.43 (s, 2H), 3.23 (s, 3H).
MS (ESI, m/z): 359.3 [M+H$^+$].

Preparation B: 6-((S)-5-iodomethyl-2-oxo-oxazolidin-3-yl)-4H-benzo[1,4]thiazin-3-one

B.i. Toluene-4-sulfonic acid (S)-2-oxo-3-(3-oxo-3,4-dihydro-2H-benzo[1,4]thiazin-6-yl)-oxazolidin-5-ylmethyl ester To a solution of intermediate A.iii (3.2 g, 11.5 mmol) and DMAP (1.40 g, 11.5 mmol) in DCM (80 mL) cooled to 0° C. were added TEA (4.6 mL, 33.3 mmol) and a solution of TsCl (2.2 g, 11.5 mmol) in DCM (15 mL). The mixture was stirred at rt overnight after which water was added. The resulting solid was filtered to afford the title compound as a beige solid (4.19 g, 84% yield).
MS (ESI, m/z): 435.2 [M+H$^+$].

B.ii. 6-((S)-5-iodomethyl-2-oxo-oxazolidin-3-yl)-4H-benzo[1,4]thiazin-3-one A suspension of intermediate B.i (4.19 g, 9.64 mmol) and NaI (5.78 g, 38.57 mmol) in acetone (70 mL) was refluxed for 5 h. The solvent was evaporated and the residue extracted with water/DCM, thus precipitating the desired product as a pale pink solid (3.39 g, 90% yield).
$^1$H NMR (DMSO-d6) δ: 10.54 (s, 1H), 7.30 (m, 2H), 7.11 (dd, J=8.5, 2.1 Hz, 1H), 4.69 (m, 1H), 4.13 (t, J=9.1 Hz, 1H), 3.57 (m, 3H), 3.43 (s, 2H).
MS (ESI, m/z): 391.1 [M+H$^+$].

Preparation C: 6-((R)-5-iodomethyl-2-oxo-oxazolidin-3-yl)-4H-benzo[1,4]thiazin-3-one Starting from tert-butyl-dimethyl-((R)-1-oxiranyl-methoxy)-silane and using the procedure of Preparation B, step B.ii, the title compound (enantiomeric antipode of the compound of Preparation B) was obtained as an off-white solid (120 mg, 33% yield).
MS (ESI, m/z): 391.1 [M+H$^+$].

Preparation D: methanesulfonic acid (S)-2-oxo-3-(3-oxo-3,4-dihydro-2H-benzo[1,4]oxazin-6-yl)-oxazolidin-5-ylmethyl ester

D.i. 6-[(S)-3-(tert-butyl-dimethyl-silanyloxy)-2-hydroxy-propylamino]-4H-benzo[1,4]oxazin-3-one Starting from 6-amino-4H-benzo[1,4]oxazin-3-one and using the procedure of Preparation A, step A.i,. the title compound was obtained as a pale brown foam (5.2 g, 66% yield).
MS (ESI, m/z): 353.3 [M+H$^+$].

D.ii. 6-[(S)-5-(tert-butyl-dimethyl-silanyloxymethyl)-2-oxo-oxazolidin-3-yl]-4H-benzo[1,4]oxazin-3-one Starting from intermediate D.i and using the procedure of Preparation A, step A.ii, the title compound was obtained as a colourless solid (5.15 g, 91% yield).
MS (ESI, m/z): 379.2 [M+H$^+$].

D.iii. 6-((S)-5-hydroxymethyl-2-oxo-oxazolidin-3-yl)-4H-benzo[1,4]oxazin-3-one Starting from intermediate D.ii and using the procedure of Preparation A, step A.iii, the title compound was obtained as a colourless solid (3.14 g, 87% yield).
MS (ESI, m/z): 265.5 [M+H$^+$].

D.iv. Methanesulfonic acid (S)-2-oxo-3-(3-oxo-3,4-dihydro-2H-benzo[1,4]oxazin-6-yl)-oxazolidin-5-ylmethyl ester Starting from intermediate D.iii and using the procedure of Preparation A, step A.iv, the title compound was obtained as an off-white solid (1.40 g, 44% yield).
$^1$H NMR (DMSO-d6) δ: 10.72 (s, 1H), 7.29 (dd, J=2.1, 0.6 Hz, 1H), 6.94 (m, 2H), 4.95 (m, 1H), 4.52 (s, 2H), 4.49 (m, 2H), 4.11 (t, J=9.1 Hz, 1H), 3.73 (m, 2H), 3.23 (s, 3H).
MS (ESI, m/z): 343.2 [M+H$^+$].

Preparation E: (S)-3-(2,3-dihydro-benzo[1,4]dioxin-6-yl)-5-iodomethyl-oxazolidin-2-one

E.i. (S)-3-(2,3-dihydro-benzo[1,4]dioxin-6-yl)-5-hydroxymethyl-oxazolidin-2-one A solution of (2,3-dihydro-benzo[1,4]dioxin-6-yl)-carbamic acid benzyl ester (3.0 g, 10.5 mmol) in THF (60 mL) was cooled to −78° C. before the drop wise addition of n-BuLi (5.1 mL of a 2.5M solution in hexanes, 1.2 eq). The mixture was stirred at −78° C. for 1 h and then warmed to −15° C. At this temperature (S)-glycidyl butyrate (1.98 g, 1.2 eq) was added dropwise. The mixture was stirred at rt overnight. Cs$_2$CO$_3$ (tip of a spatula) was added and the mixture heated at 40° C. until complete conversion. The mixture was diluted with EA and washed with a sat. NH$_4$Cl solution and water. The org. layer was dried over MgSO$_4$ and concentrated. The compound was purified by CC (Hex/EA 2:1, 1:1) affording the desired intermediate as a beige solid (1.09 g, 41% yield).
$^1$H NMR (DMSO d6) δ: 7.13 (d, J=2.5 Hz, 1H), 6.96 (dd, J=2.5, 8.9 Hz, 1H), 6.86 (d, J=8.9 Hz, 1H), 5.16 (t, J=5.8 Hz, 1H), 4.70-4.50 (m, 1H), 4.30-4.10 (m, 4H), 4.10-3.90 (m, 1H), 4.80-4.70 (m, 1H), 4.70-4.60 (m, 1H), 4.60-4.50 (m, 1H).

E.ii. Methanesulfonic acid (S)-3-(2,3-dihydro-benzo[1,4]dioxin-6-yl)-2-oxo-oxazolidin-5-ylmethyl ester A solution of intermediate E.i (1 g, 4 mmol) in DCM (20 mL) was cooled to 0° C. DIPEA (0.62 g, 1.2 eq) and MsCl (0.502 g, 1.1 eq) were added and the mixture stirred for 1 h at 0° C. The mixture was diluted with DCM and washed with water. The org. phase was dried over MgSO$_4$ and concentrated to give the title mesylate as a colourless solid (1.26 g, 97% yield), which was used in the next step without further purification.
MS (ESI, m/z): 329.8 [M+H$^+$].

E.iii. (S)-3-(2,3-dihydro-benzo[1,4]dioxin-6-yl)-5-iodomethyl-oxazolidin-2-one A mixture of intermediate E.ii (509 mg, 1.55 mmol) and NaI (927 mg, 6.18 mmol) in acetone (10 mL) was heated at reflux for 3 h. The solvent was evaporated and the residue extracted with water/DCM. The org. layer was washed with brine, dried over MgSO$_4$ and concentrated under reduced pressure to afford the title compound as a pale beige solid (393 mg, 70% yield).

$^1$H NMR (CDCl$_3$) δ: 7.07 (d, J=2.6 Hz, 1H), 6.98 (dd, J=9.1, 2.6 Hz, 1H), 6.85 (d, J=8.9 Hz, 1H), 4.68 (m, 1H), 4.24 (s, 4H), 4.10 (t, J=9.1 Hz, 1H), 3.72 (dd, J=9.1, 5.9 Hz, 1H), 3.46 (m, 1H), 3.33 (m, 1H).

MS (ESI, m/z): 362.1 [M+H$^+$].

Preparation F: (S)-3-(2,3-dihydro-benzo[1,4]dioxin-6-yl)-2-oxo-oxazolidine-5-carboxylic acid To a solution of intermediate E.i (985 mg, 3.92 mmol) in 1:1 water/MeCN (20 mL) cooled to 0° C. was added diacetoxyiodobenzene (2.83 g, 2.2 eq) and TEMPO (122 mg, 0.2 eq.). The mixture was stirred at 0° C. for 30 min and at rt overnight. EA and sat. Na$_2$CO$_3$ were added and the phases separated. The aq. layer was washed once more with EA and then carefully acidified with 1M HCl. The aq. phase was then extracted twice with EA. The combined org. layers were washed with brine and dried over MgSO$_4$ and concentrated under reduced pressure to afford the title product as a colourless solid (847 mg, 81% yield).

MS (ESI, m/z): 266.3 [M+H$^+$].

EXAMPLES

Example 1

6-{(R)-5-[3-(6-methoxy-[1,5]naphthyridin-4-yloxy)-azetidin-1-ylmethyl]-2-oxo-oxazolidin-3-yl}-4H-benzo[1,4]thiazin-3-one

1.i. 3-(6-methoxy-[1,5]naphthyridin-4-yloxy)-azetidine-1-carboxylic acid tert-butyl ester DIAD (0.69 mL, 3.45 mmol) was added dropwise to a suspension of 6-methoxy-[1,5]naphthyridin-4-ol (507 mg, 2.88 mmol), 3-hydroxy-azetidine-1-carboxylic acid tert-butyl ester (commercial, 500 mg, 2.88 mmol) and PPh$_3$ (906 mg, 3.45 mmol) in THF (5 mL). A clear solution formed which was stirred at rt overnight. The mixture was concentrated under reduced pressure and purified by CC (Hex/EA 1:1) to afford the title intermediate as a yellow solid (590 mg, 62% yield).

MS (ESI, m/z): 332.4 [M+H$^+$].

1.ii. 8-(azetidin-3-yloxy)-2-methoxy-[1,5]naphthyridine

Starting from intermediate 1.i and using method A, the desired intermediate was obtained as a yellow solid (172 mg, 42% yield).

MS (ESI, m/z): 232.5 [M+H$^+$].

1.iii. 6-{(R)-5-[3-(6-methoxy-[1,5]naphthyridin-4-yloxy)-azetidin-1-ylmethyl]-2-oxo-oxazolidin-3-yl}-4H-benzo[1,4]thiazin-3-one Starting from intermediate 1.ii and the compound of Preparation B and using method B, the desired product was obtained as a colourless solid (5 mg, 3% yield).

$^1$H NMR (CDCl$_3$) δ: 8.56 (d, J=5.3 Hz, 1H), 8.42 (s, 1H), 8.15 (d, J=8.8 Hz, 1H), 7.45 (d, J=2.3 Hz, 1H), 7.25 (m, 1H), 7.11 (d, J=9.1 Hz, 1H), 6.88 (dd, J=8.8, 2.3 Hz, 1H), 6.66 (d, J=5.3 Hz, 1H), 5.04 (t, J=5.9 Hz, 1H), 4.71 (m, 1H), 4.06 (m, 6H), 3.90 (dd, J=8.8, 6.7 Hz, 1H), 3.59 (m, 2H), 3.39 (s, 2H), 3.03 (m, 1H), 2.90 (m, 1H).

MS (ESI, m/z): 493.8 [M+H$^+$].

Example 2

6-{(R)-5-[(R)-3-(6-methoxy-quinazolin-4-yloxy)-pyrrolidin-1-ylmethyl]-2-oxo-oxazolidin-3-yl}-4H-benzo[1,4]thiazin-3-one

2.i. (R)-3-(6-methoxy-quinazolin-4-yloxy)-pyrrolidine-1-carboxylic acid tert-butyl ester Starting from (R)-3-hydroxy-pyrrolidine-1-carboxylic acid tert-butyl ester (commercial) and 4-chloro-6-methoxy-quinazoline and using method C, the desired product was obtained as a yellow oil (1.54 g, 42% yield).

MS (ESI, m/z): 346.2 [M+H$^+$].

2.ii. 6-methoxy-4-((R)-pyrrolidin-3-yloxy)-quinazoline

Starting from intermediate 2.i and using method A, the desired intermediate was obtained as an off-white solid (458 mg, 43% yield).

MS (ESI, m/z): 246.4 [M+H$^+$].

2.iii. 6-{(R)-5-[(R)-3-(6-methoxy-quinazolin-4-yloxy)-pyrrolidin-1-ylmethyl]-2-oxo-oxazolidin-3-yl}-4H-benzo[1,4]thiazin-3-one Starting from intermediate 2.ii and the compound of Preparation B and using method B, the desired product was obtained as a brown foam (70 mg, 41% yield).

MS (ESI, m/z): 508.1 [M+H$^+$].

Example 3

6-{(R)-5-[(S)-3-(6-methoxy-quinazolin-4-yloxy)-pyrrolidin-1-ylmethyl]-2-oxo-oxazolidin-3-yl}-4H-benzo[1,4]thiazin-3-one The title compound was obtained as a brown solid (83 mg, 49% yield) starting from the enantiomeric antipode of intermediate 2.ii and using the procedure of Example 2, step 2.iii.

MS (ESI, m/z): 508.2 [M+H$^+$].

Example 4

(R)-3-(2,3-dihydro-benzo[1,4]dioxin-6-yl)-5-[(RS)-3-(6-methoxy-quinazolin-4-yloxy)-pyrrolidin-1-ylmethyl]-oxazolidin-2-one The title compound was obtained as a pale yellow foam (33 mg, 32% yield) starting from the racemate of intermediate 2.ii and using the procedure of Example 2, step 2.iii.

MS (ESI, m/z): 479.3 [M+H$^+$].

Example 5

6-{(R)-5-[(2S,4S)-2-hydroxymethyl-4-(6-methoxy-quinazolin-4-yloxy)-pyrrolidin-1-ylmethyl]-2-oxo-oxazolidin-3-yl}-4H-benzo[1,4]thiazin-3-one

5.i. (2S,4S)-2-(2,2-dimethyl-propionyloxymethyl)-4-hydroxy-pyrrolidine-1-carboxylic acid tert-butyl ester To a stirred solution of (S)-2-(2,2-dimethyl-propionyloxymethyl)-4-oxo-pyrrolidine-1-carboxylic acid tert-butyl ester (50 g, 16.7 mmol; prepared according to WO 2007/017828) in MeOH (40 mL) was added NaBH$_4$ (1.90 g, 3 eq.) in portions within 30 min at 0-5° C. The mixture was stirred at 10° C. for 2 h. Water was added and the mixture was extracted with DCM. The org. layer was dried over MgSO$_4$ and concentrated under reduced pressure to afford the title intermediate as a beige solid (4.13 g, 82% yield).

$^1$H NMR (CDCl3) δ: 4.42 (m, 1H), 4.26 (m, 1H), 4.10-4.00 (m, 1H), 3.60 (m, 1H), 3.36 (m, 1H), 2.19 (m, 2H), 1.95 (m, 1H), 1.46 (s, 9H), 1.21 (s, 9H).

MS (ESI, m/z): 302.2 [M+H$^+$].

5.ii. (2S,4S)-2-(2,2-dimethyl-propionyloxymethyl)-4-(6-methoxy-quinazolin-4-yloxy)-pyrrolidine-1-carboxylic acid tert-butyl ester Starting from intermediate 5.i and using method C, the desired intermediate was obtained as a pale yellow foam (1.56 g, 56% yield).

MS (ESI, m/z): 460.0 [M+H$^+$].

5.iii. (2S,4S)-2-hydroxymethyl-4-(6-methoxy-quinazolin-4-yloxy)-pyrrolidine-1-carboxylic acid tert-butyl ester DIBAH (1.92 mL, 1.7M in toluene) was slowly added to a solution of intermediate 5.ii (500 mg, 1.1 mmol) in toluene (16 mL) at −78° C. The mixture was stirred at −78° C. for 2 h, quenched by the dropwise addition of a sat. solution of Rochelle's salt (1.5 mL). The mixture was allowed to warm to rt and was diluted with EA. The org. layer was dried over MgSO$_4$ and concentrated under reduced pressure to afford the title intermediate as a pale yellow solid (440 mg, 100% yield).

MS (ESI, m/z): 376.5 [M+H$^+$].

5.iv. [(2S,4S)-4-(6-methoxy-quinazolin-4-yloxy)-pyrrolidin-2-yl]-methanol

Starting from intermediate 5.iii and using method A, the desired intermediate was obtained as a pale yellow solid (162 mg, 50% yield).

MS (ESI, m/z): 276.2 [M+H$^+$].

5.v. 6-{(R)-5-[(2S,4S)-2-hydroxymethyl-4-(6-methoxy-quinazolin-4-yloxy)-pyrrolidin-1-ylmethyl]-2-oxo-oxazolidin-3-yl}-4H-benzo[1,4]thiazin-3-one Starting from intermediate 5.iv and the compound of Preparation B and using method B, the desired product was obtained as a colourless foam (40 mg, 41% yield).

$^1$H NMR (CDCl$_3$) δ: 8.60 (s, 1H), 8.41 (s, 1H), 7.80 (d, J=9.1 Hz, 1H), 7.43 (m, 1H), 7.34 (d, J=2.6 Hz, 1H), 7.23 (m, 1H), 7.11 (d, J=8.8 Hz, 1H), 6.82 (m, 1H), 5.71 (m, 1H), 4.74 (m, 1H), 3.97 (m, 1H), 3.91 (s, 3H), 3.76 (m, 2H), 3.59 (m, 2H), 3.39 (s, 2H), 3.17 (m, 1H), 2.97 (m, 2H), 2.80 (m, 2H), 2.54 (m, 1H), 2.22 (m, 1H).

MS (ESI, m/z): 538.2 [M+H$^+$].

Example 6

6-{(R)-5-[(2S,4S)-2-azidomethyl-4-(6-methoxy-quinazolin-4-yloxy)-pyrrolidin-1-ylmethyl]-2-oxo-oxazolidin-3-yl}-4H-benzo[1,4]thiazin-3-one

6.i. (2S,4S)-2-azidomethyl-4-(6-methoxy-quinazolin-4-yloxy)-pyrrolidine-1-carboxylic acid tert-butyl ester A slightly yellow solution of intermediate 5.iii (603 mg, 1.61 mmol) in anhydrous DCM (7 mL) and DIPEA (0.825 mL, 3 eq) was cooled to 0° C. and MsCl (0.15 mL, 1.2 eq) was added dropwise. The resulting mixture was stirred at 0° C. for 1 h. Water was added and the mixture was extracted with DCM. The org. layer was dried over MgSO$_4$ and concentrated under reduced pressure. To a solution of the crude mesylate in DMF (6 mL) was added NaN$_3$ (165 mg, 1.5 eq.). The resulting mixture was stirred at 80° C. overnight. The solvent was evaporated to dryness and dissolved in DCM. The org. layer was washed with water, dried over MgSO$_4$ and evaporated under reduced pressure to afford the title intermediate as a brown oil (621 mg, 92% yield).

MS (ESI, m/z): 401.4 [M+H$^+$].

6.ii. 4-((3S,5S)-5-azidomethyl-pyrrolidin-3-yloxy)-6-methoxy-quinazoline

Starting from intermediate 6.i and using method A, the desired intermediate was obtained as a brown oil (465 mg, 100% yield).

MS (ESI, m/z): 302.3 [M+H$^+$].

6.iii. 6-{(R)-5-[(2S,4S)-2-azidomethyl-4-(6-methoxy-quinazolin-4-yloxy)-pyrrolidin-1-ylmethyl]-2-oxo-oxazolidin-3-yl}-4H-benzo[1,4]thiazin-3-one Starting from intermediate 6.ii and the compound of Preparation B, and using method B and, the desired product was obtained as a pale yellow foam (131 mg, 30% yield).

MS (ESI, m/z): 563.3 [M+H$^+$].

Example 7

1-[(R)-2-oxo-3-(3-oxo-3,4-dihydro-2H-benzo[1,4]thiazin-6-yl)-oxazolidin-5-ylmethyl]-azetidine-3-carboxylic acid (6-methoxy-[1,5]naphthyridin-4-yl)-amide

7.i. 3-(6-methoxy-[1,5]naphthyridin-4-ylcarbamoyl)-azetidine-1-carboxylic acid tert-butyl ester Starting from 6-methoxy-[1,5]naphthyridin-4-ylamine and azetidine-1,3-dicarboxylic acid mono-tert-butyl ester and using method D, the desired product was obtained as a beige solid (1.60 g, 60% yield).

MS (ESI, m/z): 359.4 [M+H$^+$].

7. ii. Azetidine-3-carboxylic acid (6-methoxy-[1,5]naphthyridin-4-yl)-amide

Starting from intermediate 7.i and using method A, the desired intermediate was obtained as a brown solid (1.25 g, 100% yield).
$^1$H NMR (CDCl$_3$) δ: 10.35 (br. s, 1H), 8.71 (d, J=5.3 Hz, 1H), 8.53 (d, J=5.3 Hz, 1H), 8.21 (d, J=9.1 Hz, 1H), 7.15 (d, J=8.8 Hz, 1H), 4.10 (s, 3H), 3.97 (m, 4H), 3.55 (m, 1H).
MS (ESI, m/z): 259.3 [M+H$^+$].

7. iii. 1-[(R)-2-oxo-3-(3-oxo-3,4-dihydro-2H-benzo[1,4]thiazin-6-yl)-oxazolidin-5-ylmethyl]-azetidine-3-carboxylic acid (6-methoxy-[1,5]naphthyridin-4-yl)-amide Starting from intermediate 7.ii and the compound of Preparation A and using method B, the desired product was obtained as a pale yellow foam (37 mg, 34% yield).
MS (ESI, m/z): 521.4 [M+H$^+$].

Example 8

(RS)-1-[(R)-2-oxo-3-(3-oxo-3,4-dihydro-2H-benzo[1,4]thiazin-6-yl)-oxazolidin-5-ylmethyl]-pyrrolidine-3-carboxylic acid (6-methoxy-[1,5]naphthyridin-4-yl)-amide The title compound was obtained as a colourless solid (25 mg, 22% yield) using the procedures of Example 7, starting however the synthetic sequence with rac-pyrrolidine-1,3-dicarboxylic acid 1-tert-butyl ester.
MS (ESI, m/z): 535.4 [M+H$^+$].

Example 9

6-((R)-5-{(RS)-3-[(E)-2-(6-methoxy-[1,5]naphthyridin-4-yl)-vinyl]-pyrrolidin-1-ylmethyl}-2-oxo-oxazolidin-3-yl)-4H-benzo[1,4]thiazin-3-one

9.i. (RS)-3-(1-phenyl-1H-tetrazole-5-sulfonylmethyl)-pyrrolidine-1-carboxylic acid tert-butyl ester To a solution of 1-phenyl-1H-tetrazole-5-thiol (5.92 g, 33 mmol) in EtOH (80 mL) was added KOH (2.1 g, 38 mmol) and the mixture was heated at reflux for 1 h. (RS)-3-iodomethyl-pyrrolidine-1-carboxylic acid tert-butyl ester (9.0 g, 29 mmol) was added and refluxing was continued for 3 h. Water (70 mL) was added and the majority of EtOH was removed under reduced pressure. The residue was extracted with EA and the org. layer was washed with water and brine, dried over MgSO$_4$ and concentrated. To the crude sulfide thus obtained in EtOH (200 mL) was added ammonium molybdate (7.0 g, 0.2 eq) and 30% H$_2$O$_2$ (15 mL) and the mixture was heated to 65° C. and stirred at that temperature for 3 h. Water (500 mL) was added and the majority of EtOH was removed under reduced pressure. The residue was extracted with EA. The org. layer was washed with 10% Na$_2$S$_2$O$_3$, water and brine, dried over MgSO$_4$ and concentrated under reduced pressure to afford the title intermediate as a pale yellow oil (9.48 g, 85% yield).
MS (ESI, m/z): 394.3 [M+H$^+$].

9.ii. (RS)-3-[(E)-2-(6-methoxy-[1,5]naphthyridin-4-yl)-vinyl]-pyrrolidine-1-carboxylic acid tert-butyl ester To a suspension of 6-methoxy-[1,5]naphthyridine-4-carbaldehyde (2.0 g, 10.6 mmol) and intermediate 9.i (4.40 g, 1.05 eq.) in 1,2-DME (60 mL), cooled to −78° C., was added a solution of KHMDS (0.5M in toluene, 34 mL) dropwise. The mixture was stirred 1 h at this temperature before warming to rt. After further stirring for 45 min, water (150 mL) and EA (150 mL) were added. The two layers were separated and the aq layer was extracted twice with EA (200 mL). The combined org. layers were dried over MgSO$_4$, filtered and concentrated under reduced pressure. The residue was purified by CC (Hept-EA 1-1) to afford the title intermediate as a yellow oil (2.1 g, 56% yield).
MS (ESI, m/z): 356.3 [M+H$^+$].

9.iii. (RS)-2-methoxy-8-((E)-2-pyrrolidin-3-yl-vinyl)-[1,5]naphthyridine

Starting from intermediate 9.ii and using method A, the desired intermediate was obtained as a yellow oil (187 mg, 100% yield).
MS (ESI, m/z): 256.5 [M+H$^+$].

9.iv. 6-((R)-5-{(RS)-3-[(E)-2-(6-methoxy-[1,5]naphthyridin-4-yl)-vinyl]-pyrrolidin-1-ylmethyl}-2-oxo-oxazolidin-3-yl)-4H-benzo[1,4]thiazin-3-one Starting from intermediate 9.iii and the compound of Preparation A and using method B, the desired product was obtained as a pale yellow solid (28 mg, 22% yield).
$^1$H NMR (CDCl$_3$) δ: 8.67 (dd, J=4.4, 2.3 Hz, 1H), 8.38 (m, 1H), 8.18 (d, J=9.1 Hz, 1H), 7.56 (dd, J=4.7, 2.9 Hz, 1H), 7.45 (m, 2H), 7.26 (m, 1H), 7.11 (d, J=9.1 Hz, 1H), 6.96 (dd, J=8.8, 2.3 Hz, 1H), 6.71 (m, 1H), 4.78 (m, 1H), 4.07 (m, 4H), 3.87 (ddd, J=8.8, 6.7, 4.7 Hz, 1H), 3.41 (s, 2H), 3.20-2.80 (m, 6H), 2.62 (m, 1H), 2.22 (m, 1H), 1.81 (m, 1H).
MS (ESI, m/z): 518.3 [M+H$^+$].

Example 10

6-((R)-5-{(RS)-3-[2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one

10.i. (RS)-3-[2-(6-methoxy-[1,5]naphthyridin-4-yl)-ethyl]-pyrrolidine-1-carboxylic acid tert-butyl ester A solution of intermediate 9.ii (287 mg, 0.78 mmol) in EA (10 mL) was hydrogenated over Pd/C (10%; 100 mg) for 1 h. The catalyst was filtered and the filter cake was washed with EA. The filtrate was concentrated under reduced pressure to afford the title intermediate as a grey oil (267 mg, 96% yield).
MS (ESI, m/z): 358.3 [M+H$^+$].

10.ii. (RS)-2-methoxy-8-(2-pyrrolidin-3-yl-ethyl)-[1,5]naphthyridine

Starting from intermediate 10.i and using method A, the desired intermediate was obtained as a yellow oil (165 mg, 86% yield).
MS (ESI, m/z): 258.2 [M+H$^+$].

10.iii. 6-((R)-5-{(RS)-3-[2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one Starting from intermediate 10.ii and intermediate A and using method B, the desired product was obtained as a colourless solid (25 mg, 20% yield).
MS (ESI, m/z): 520.5 [M+H$^+$].

Example 11

6-((R)-5-{(RS)-3-[(1R,2R)-1,2-dihydroxy-2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one

11.i. (RS)-3-[(1R,2R)-1,2-dihydroxy-2-(6-methoxy-[1,5]naphthyridin-4-yl)-ethyl]-pyrrolidine-1-carboxylic acid tert-butyl ester To a suspension of intermediate 9.ii (662 mg, 1.86 mmol) in tBuOH (10 mL) and water (10 mL) were added methanesulfonamide (213 mg, 1.2 eq) and AD-mix β (2.7 g). The reaction mixture was vigorously stirred at rt overnight. The reaction mixture was diluted with water and EA. The two layers were decanted and the aq. layer was extracted twice with EA. The combined org. layers were washed with 10% aq. NaHSO₃, water (50 mL) and brine, dried over MgSO₄, filtered and concentrated to dryness under reduced pressure to afford the title intermediate as a colourless foam (660 mg, 91% yield).

MS (ESI, m/z): 390.4 [M+H$^+$].

11.ii. (RS)-3-[(4R,5R)-5-(6-methoxy-[1,5]naphthyridin-4-yl)-2,2-dimethyl-[1,3]dioxolan-4-yl]-pyrrolidine-1-carboxylic acid tert-butyl ester To a solution of intermediate 11.i (371 mg, 0.95 mmol) in THF (10 mL) were added TsOH (199 mg, 1.1 eq.) and 2,2-dimethoxypropane (0.35 mL, 3 eq.). The mixture was stirred at rt for 36 h. Sat. sodium bicarbonate and EA were added. The two layers were decanted and the aq. layer was extracted once with EA. The combined org. layers were washed with brine, dried over MgSO₄, filtered and concentrated to dryness. The residue was chromatographed (DCM-MeOH—NH₄OH 1000-50-4) to afford the title intermediate as a colourless foam (265 mg, 65% yield).

MS (ESI, m/z): 430.3 [M+H$^+$].

11.iii. 6-((R)-5-{(RS)-3-[(4R,5R)-5-(6-methoxy-[1,5]naphthyridin-4-yl)-2,2-dimethyl-[1,3]dioxolan-4-yl]-pyrrolidin-1-ylmethyl}-2-oxo-oxazolidin-3-yl)-4H-benzo[1,4]thiazin-3-one To an ice-chilled solution of intermediate 11.ii.) (220 mg, 0.51 mmol) in DCM (3 mL), were added dropwise under N₂, 2,6-lutidine (0.24 mL, 4 eq) and TBDMSOTf (0.24 mL, 2 eq). After 1 h at 0° C., the reaction mixture was quenched by adding sodium bicarbonate and DCM. The two layers were decanted and the org. layers were dried over MgSO₄, filtered and concentrated to dryness under reduced pressure. To a solution of the crude silyl carbamate thus obtained in THF (3 mL) was added TBAF (1M in THF, 1.05 mL, 2 eq.). The reaction proceeded for 30 min. The solvent was evaporated and the residue chromatographed (DCM-MeOH—NH₄OH 1000-100-8) to afford a yellow oil (140 mg, 83% yield).

MS (ESI, m/z): 330.3 [M+H$^+$].

The resulting free amine (81 mg, 0.25 mmol) was reacted with the compound of Preparation A using method B to afford the desired product as a brown oil (78 mg, 54% yield).

MS (ESI, m/z): 592.4 [M+H$^+$].

11.iv. 6-((R)-5-{(RS)-3-[(1R,2R)-1,2-dihydroxy-2-(6-methoxy-[1,5]naphthyridin-4-yl)-ethyl]-pyrrolidin-1-ylmethyl}-2-oxo-oxazolidin-3-yl)-4H benzo[1,4]thiazin-3-one A solution of intermediate 11.iii (70 mg, 0.12 mmol) in aq. TFA (80%, 2 mL) was stirred at 40° C. for 1 h. The volatiles were removed in vacuo and the residue was taken in sat. sodium bicarbonate. The solid was filtered off, washed with water and lyophilized. The residue was chromatographed (DCM-MeOH—NH₄OH 1000-100-8) to afford the title compound as a beige solid (34 mg, 52%).

$^1$H NMR (DMSO-d6) δ: 10.52 (m, 1H), 8.74 (d, J=4.7 Hz, 1H), 8.24 (dd, J=9.1, 0.6 Hz, 1H), 7.72 (d, J=4.4 Hz, 1H), 7.27 (m, 3H), 7.09 (m, 1H), 5.53 (m, 1H), 5.30 (m, 1H), 4.76 (m, 1H), 4.32 (m, 1H), 4.02 (m, 5H), 3.68 (m, 2H), 3.42 (s, 2H), 2.65 (m, 6H), 1.81 (m, 2H).

MS (ESI, m/z): 552.5 [M+H$^+$].

Example 12

6-{(R)-5-[4-(3-methoxy-quinoxalin-5-ylmethylene)-piperidin-1-ylmethyl]-2-oxo-oxazolidin-3-yl}-4H-benzo[1,4]thiazin-3-one

12.i. (3-methoxy-quinoxalin-5-yl)-methanol

To a stirred suspension of 3-methoxy-quinoxaline-5-carbaldehyde (5.0 g, 26.6 mmol, prepared according to WO 2007/107965) in EtOH (200 mL) cooled at 0° C., NaBH₄ (1.1 g, 1.1 eq.) was added in one portion. The reaction mixture was warmed to rt and THF (50 mL) was added. A clear solution was obtained. The mixture was further stirred at rt for 30 min. Water (200 mL) was added and the volatiles were removed in vacuo. The residue was filtered off, washed with water. The solid was dried under HV to afford the title alcohol as a brown solid (4.8 g, 95% yield).

MS (ESI, m/z): 191.3 [M+H$^+$].

12.ii. 8-bromomethyl-2-methoxy-quinoxaline

To a stirred solution of intermediate 12.i (4.8 g, 25 mmol) in DMF (45 mL), PBr₃ (2.6 mL, 1.1 eq.) was added dropwise at rt. During the course of the addition a solid formed. The reaction was then stirred 30 minutes and sodium bicarbonate was added. The solid that formed was filtered off and thoroughly washed with water. The solid was then lyophilized to afford the title intermediate as a beige solid (5.45 g, 85% yield).

$^1$H NMR (CDCl₃) δ: 8.51 (s, 1H), 7.99 (dd, J=8.2, 1.5 Hz, 1H), 7.78 (dd, J=7.3, 1.5 Hz, 1H), 7.52 (dd, J=8.2, 7.3 Hz, 1H), 5.08 (s, 2H), 4.15 (s, 3H).

12.iii. (3-methoxy-quinoxalin-5-ylmethyl)-triphenyl-phosphonium bromide

A solution of intermediate 12.ii (4.54 g, 17.9 mmol) and PPh₃ (5.65 g, 1.2 eq.) in toluene (100 mL) was heated at reflux for 6 h. After cooling to rt, the resulting precipitate was filtered and washed with EA to afford the title intermediate as a beige solid (8.59 g, 93% yield).

$^1$H NMR (DMSO-d6) δ: 8.43 (s, 1H), 7.96 (dt, J=7.6, 2.1 Hz, 1H), 7.83 (m, 3H), 7.57 (m, 12H), 5.56 (d, J=14.9 Hz, 2H), 3.74 (s, 3H).

12.iv. 4-(3-methoxy-quinoxalin-5-ylmethylene)-piperidine-1-carboxylic acid tert-butyl ester A solution of nBuLi (2 mL, 2.4M in hexanes) was added dropwise, under a nitrogen atmosphere at −78° C. to a suspension of intermediate 12.iii (2.50 g, 4.85 mmol) in dry THF (20 mL). After 15 min a solution of 4-oxo-piperidine-1-carboxylic acid tert-butyl ester (0.97 g, 1 eq.) in dry THF (15 mL) was added at rt. The mixture was stirred at rt overnight after which it was cooled to 0° C. and quenched by the addition of sat. NH$_4$Cl and diluted with EA. The org. layer was washed with sat. NaHCO$_3$ and brine, dried over MgSO$_4$ and concentrated under reduced pressure. The residue was purified by CC (Hept-EA 2-1) to afford the title intermediate as a pale yellow oil (552 mg, 32% yield).

MS (ESI, m/z): 356.2 [M+H$^+$].

12. v. 2-methoxy-8-piperidin-4-ylidenemethyl-quinoxaline

Starting from intermediate 12.iv and using method A, the desired intermediate was obtained as a dark yellow oil (41 mg, 57% yield).

MS (ESI, m/z): 256.3 [M+H$^+$].

12. vi. 6-{(R)-5-[4-(3-methoxy-quinoxalin-5-ylmethylene)-piperidin-1 ylmethyl]-2-oxo-oxazolidin-3-yl}-4H-benzo[1,4]thiazin-3-one Starting from intermediate 12.v and intermediate A and using method B, the desired product was obtained as a beige solid (24 mg, 34% yield).

MS (ESI, m/z): 518.4 [M+H$^+$].

Example 13

6-((R)-5-{4-hydroxy-4-[(RS)-hydroxy-(3-methoxy-quinoxalin-5-yl)-methyl]-piperidin-1-ylmethyl}-2-oxo-oxazolidin-3-yl)-4H-benzo[1,4]thiazin-3-one 13.i. (RS)-4-hydroxy-4-[hydroxy-(3-methoxy-quinoxalin-5-yl)-methyl]-piperidine-1-carboxylic acid tert-butyl ester To a solution of intermediate 12.iv (485 mg, 1.4 mmol) in DCM (3 mL) was added water (1 mL), NMO (192 mg, 1.2 eq.) and the potassium osmate dihydrate (20 mg). The resulting mixture was vigorously stirred at rt over night. The mixture was poured into water and the org. layer was washed with sat. Na$_2$S$_2$O$_3$. The aq. layers were extracted with DCM and the combined org. layers were dried over MgSO$_4$ and concentrated. The residue was purified by CC (DCM-MeOH—NH$_4$OH 1000-100-8) to afford the title intermediate as a colourless foam (318 mg, 60% yield).

MS (ESI, m/z): 390.3 [M+H$^+$].

13. ii. (RS)-4-(3-methoxy-quinoxalin-5-yl)-2,2-dimethyl-1,3-dioxa-8-aza-spiro[4.5]decane-8-carboxylic acid tert-butyl ester Starting from intermediate 13.i and using the procedure of Example 11, step 11.ii, the title intermediate was obtained as a yellow foam (187 mg, 55% yield).

MS (ESI, m/z): 430.3 [M+H$^+$].

13.iii. 6-{(R)-5-[(RS)-4-(3-methoxy-quinoxalin-5-yl)-2,2-dimethyl-1,3-dioxa-8-aza-spiro[4.5]dec-8-ylmethyl]-2-oxo-oxazolidin-3-yl}-4H-benzo[1,4]thiazin-3-one Starting from intermediate 13.ii and using the procedure of Example 11, step 11.iii, the title intermediate was obtained as a colourless solid (130 mg, 81% yield).

MS (ESI, m/z): 592.4 [M+H$^+$].

13.iv. 6-((R)-5-{4-hydroxy-4-[(RS)-hydroxy-(3-methoxy-quinoxalin-5-yl)-methyl]-piperidin-1-ylmethyl}-2-oxo-oxazolidin-3-yl)-4H-benzo[1,4]thiazin-3-one Starting from intermediate 13.iii and using the procedure of Example 11, step 11.iv, the title compound was obtained as a beige solid (56 mg, 48% yield).

$^1$H NMR (CDCl$_3$) δ: 8.49 (m, 1H), 7.97 (m, 2H), 7.58 (m, 2H), 7.36 (s, 1H), 7.23 (m, 1H), 6.88 (dd, J=8.8, 2.3 Hz, 1H), 5.13 (s, 1H), 4.70 (m, 1H), 4.06 (s, 3H), 3.95 (t, J=8.5 Hz, 1H), 3.67 (m, 1H), 3.46 (s, 2H), 3.37 (s, 2H), 3.23 (m, 1H), 2.62 (m, 5H), 1.86 (m, 1H), 1.63 (m, 2H), 1.31 (m, 1H).

MS (ESI, m/z): 552.5 [M+H$^+$].

Example 14

6-((R)-5-{3-[(6-methoxy-[1,5]naphthyridin-4-ylamino)-methyl]-azetidin-1-ylmethyl}-2-oxo-oxazolidin-3-yl)-4H-benzo[1,4]thiazin-3-one 14.i. (1-benzhydryl-azetidin-3-ylmethyl)-(6-methoxy-[1,5]naphthyridin-4-yl)-amine Starting from trifluoromethanesulfonic acid 6-methoxy-quinolin-4-yl ester (prepared according to WO 00/40554) and 3-aminomethyl-1-diphenylmethylazetidine (commercial) and using method E, the desired intermediate was isolated after CC (DCM/MeOH/NH$_4$OH 100/50/4) as a colourless oil (1.25 g, 35% yield).

MS (ESI, m/z): 411.1 [M+H$^+$].

14.ii. Azetidin-3-ylmethyl-(6-methoxy-[1,5]naphthyridin-4-yl)-amine

A solution of intermediate 14.i (50 mg, 0.085 mmol) in DCM (0.5 mL), cooled to 0° C., is treated with 1-chloroethylchloroformate (35 mg, 2.5 eq) and allowed to warm to rt. The reaction mixture was stirred overnight and then concentrated under reduced pressure. The residue was dissolved in MeOH and stirred at rt for 3.5 h. The solution was concentrated and the residue was purified by column chromatography (DCM/MeOH/NH$_4$OH 1000/200/16) to afford the title intermediate as a colourless solid (5 mg, 24% yield).

MS (ESI, m/z): 245.1 [M+H$^+$].

14.iii. 6-((R)-5-{3-[(6-methoxy-[1,5]naphthyridin-4-ylamino)-methyl]-azetidin-1-ylmethyl}-2-oxo-oxazolidin-3-yl)-4H-benzo[1,4]thiazin-3-one Starting from intermediate 14.ii and the compound of Preparation B and using method B, the desired product was obtained as a colourless solid (2 mg, 19% yield).

MS (ESI, m/z): 507.1 [M+H$^+$].

Example 15

6-{(R)-5-[(2S,4S)-2-aminomethyl-4-(6-methoxy-quinazolin-4-yloxy)-pyrrolidin-1-ylmethyl]-2-oxo-oxazolidin-3-yl}-4H-benzo[1,4]thiazin-3-one To a solution of compound 6.iii (35 mg, 0.065 mmol) in THF (1.5 mL) were added PPh$_3$ (33 mg, 2 eq.) and water (0.01 mL). The mixture was heated at 50° C. for 3 h. The reaction mixture was concentrated to dryness and the residue was purified by CC (DCM/MeOH/NH$_4$OH 1000/200/16) to afford the title compound as a colourless solid (5 mg, 24% yield).
MS (ESI, m/z): 537.3 [M+H$^+$].

Example 16

6-{(R)-5-[(3R*,4R*)-3-(6-methoxy-quinazolin-4-yloxy)-4-[1,2,3]triazol-1-yl-pyrrolidin-1-ylmethyl]-2-oxo-oxazolidin-3-yl}-4H-benzo[1,4]thiazin-3-one

16.i. (3R*,4R*)-3-azido-4-(6-methoxy-quinazolin-4-yloxy)-pyrrolidine-1-carboxylic acid tert-butyl ester Starting from (3R*,4R*)-3-azido-4-hydroxy-pyrrolidine-1-carboxylic acid tert-butyl ester (prepared according to *Tetrahedron Asymmetry* (2001), 12, 2989) and using method C, the desired intermediate was obtained as a yellow oil (2.18 g, 69% yield).
MS (ESI, m/z): 387.3 [M+H$^+$].

16.ii. 4-((3R*,4R*)-4-azido-pyrrolidin-3-yloxy)-6-methoxy-quinazoline

Starting from intermediate 16.i and using method A, the desired intermediate was obtained as a yellowish solid (984 mg, 61% yield).
MS (ESI, m/z): 287.3 [M+H$^+$].

16.iii. 6-{(R)-5-[(3R*,4R*)-3-azido-4-(6-methoxy-quinazolin-4-yloxy)-pyrrolidin-1-ylmethyl]-2-oxo-oxazolidin-3-yl}-4H-benzo[1,4]thiazin-3-one Starting from intermediate 16.ii and the compound of Preparation B and using method B, the desired product was isolated as a colourless solid (61 mg, 20% yield).
MS (ESI, m/z): 549.3 [M+H$^+$].

16.iv. 6-{(R)-5-[(3R*,4R*)-3-(6-methoxy-quinazolin-4-yloxy)-4-[1,2,3]triazol-1-yl-pyrrolidin-1-ylmethyl]-2-oxo-oxazolidin-3-yl}-4H-benzo[1,4]thiazin-3-one A solution of intermediate 16.iii (30 mg, 0.055 mmol) and bicyclo[2.2.1]hepta-2,5-diene (20 mg, 4 eq.) in dioxane (0.5 mL) was refluxed overnight. The mixture was concentrated and was purified by CC (DCM/MeOH/NH$_4$OH 1000/50/4) to afford the title compound as a yellow solid (9 mg, 29% yield).
MS (ESI, m/z): 575.2 [M+H$^+$].

Example 17

N-{(2S,4S)-4-(6-methoxy-quinazolin-4-yloxy)-1-[(R)-2-oxo-3-(3-oxo-3,4-dihydro-2H-benzo[1,4]thiazin-6-yl)-oxazolidin-5-ylmethyl]-pyrrolidin-2-ylmethyl}-acetamide To a solution of the compound of Example 15 (13 mg, 0.024 mmol) in DMF (0.5 mL) was added AcOH (1 L, 1 eq.), DIPEA (9 L, 3 eq.), HOBT (3 mg, 1 eq.) and EDC (6 mg, 1.2 eq.) at rt. After stirring for 8 h at rt water was added and the mixture was extracted with EA. The org. layer was washed with water and brine, dried over MgSO$_4$ and concentrated. The residue was purified by CC (DCM/MeOH/NH$_4$OH 1000/50/4) to afford the title compound as a yellow foam (6 mg, 43% yield).
MS (ESI, m/z): 579.2 [M+H$^+$].

Example 18

6-{(R)-5-[(3R*,4R*)-3-amino-4-(6-methoxy-quinazolin-4-yloxy)-pyrrolidin-1-ylmethyl]-2-oxo-oxazolidin-3-yl}-4H-benzo[1,4]thiazin-3-one To a solution of compound 16.iii (20 mg, 0.36 mmol) in THF (1.5 mL) were added PPh$_3$ (19 mg, 2 eq.) and water (0.007 mL). The mixture was heated at 50° C. for 3 h. The reaction mixture was concentrated to dryness and the residue was purified by CC (DCM/MeOH/NH$_4$OH 1000/100/8) to afford the title compound as a yellow foam (15 mg, 79% yield).
MS (ESI, m/z): 523.0 [M+H$^+$].

Example 19

6-{(R)-5-[(2S,4S)-4-(6-methoxy-quinazolin-4-yloxy)-2-[1,2,3]triazol-1-ylmethyl-pyrrolidin-1-ylmethyl]-2-oxo-oxazolidin-3-yl}-4H-benzo[1,4]thiazin-3-one A solution of the compound of Example 6 (30 mg, 0.053 mmol) and bicyclo[2.2.1]hepta-2,5-diene (20 mg, 4 eq.) in dioxane (0.5 mL) was refluxed overnight. The mixture was concentrated and was purified by CC (DCM/MeOH/NH$_4$OH 1000/50/4) to afford the title compound as a yellow foam (17 mg, 54% yield).
$^1$H NMR (CDCl$_3$) δ: 8.64 (s, 1H), 8.21 (d, J=0.6 Hz, 1H), 7.86 (d, J=9.1 Hz, 1H), 7.66 (m, 2H), 7.49 (m, 1H), 7.33 (m, 2H), 7.23 (m, 1H), 6.99 (m, 1H), 5.77 (m, 1H), 4.63 (m, 2H), 4.00-3.60 (m, 6H), 3.58-3.36 (m, 4H), 3.06 (m, 2H), 2.90 (m, 2H), 2.58 (m, 1H), 2.05 (m, 1H).
MS (ESI, m/z): 589.1 [M+H$^+$].

Example 20

6-{(R)-5-[4-(6-methoxy-quinazolin-4-yloxy)-piperidin-1-ylmethyl]-2-oxo-oxazolidin-3-yl}-4H-benzo[1,4]thiazin-3-one

20.i. 4-(6-methoxy-quinazolin-4-yloxy)-piperidine-1-carboxylic acid tert-butyl ester Starting from 4-hydroxy-piperidine-1-carboxylic acid tert-butyl ester (commercial) and 4-chloro-6-methoxy-quinazoline and using method C, the desired product was obtained as a yellow solid (649 mg, 50% yield).
MS (ESI, m/z): 360.5 [M+H$^+$].

20.ii. 6-methoxy-4-(piperidin-4-yloxy)-quinazoline

Starting from intermediate 20.i and using method A, the desired intermediate was obtained as a yellow solid (469 mg, 100% yield).
MS (ESI, m/z): 260.2 [M+H$^+$].

20.iii. 6-{(R)-5-[4-(6-methoxy-quinazolin-4-yloxy)-piperidin-1-ylmethyl]-2 oxo-oxazolidin-3-yl}-4H-benzo[1,4]thiazin-3-one Starting from intermediate 20.ii and the compound of Preparation B and using method B, the desired product was obtained as an off-white solid (66 mg, 49% yield).
$^1$H NMR (DMSO-d6) δ: 10.53 (s, 1H), 8.64 (s, 1H), 7.83 (d, J=9.1 Hz, 1H), 7.56 (dd, J=9.1, 2.9 Hz, 1H), 7.34 (m, 3H), 7.12 (dd, J=8.8, 2.3 Hz, 1H), 5.36 (m, 1H), 4.84 (m, 1H), 4.08 (m, 1H), 3.89 (s, 3H), 3.73 (m, 1H), 3.42 (s, 2H), 2.85 (m, 2H), 2.76 (m, 2H), 2.49 (m, 2H), 2.05 (m, 2H), 1.84 (m, 2H).

MS (ESI, m/z): 522.2 [M+H$^+$].

Example 21

6-{(R)-5-[(3R*,4S*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one

21.i. (3R*,4S*)-3,4-dihydroxy-pyrrolidine-1-carboxylic acid tert-butyl ester To a solution of 2,5-dihydro-pyrrole-1-carboxylic acid tert-butyl ester (commercial, 1.0 g, 5.91 mmol) in tBuOH (25 mL) and water (25 mL) was added AD-mix α (0.75 g) and AD-mix β (0.75 g). The resulting mixture was stirred at rt overnight. Again AD-mix α (0.5 g) and AD-mix β (0.5 g) were added and stirring was continued at rt overnight. Sodium bisulfate (10 g) was added and the mixture was stirred for 30 min. The phases were separated and the aq. layer was extracted with DCM-MeOH 9-1 (2×40 mL). The org. layer was dried over MgSO$_4$, filtered and concentrated under reduced pressure. The residue was purified by CC (DCM/MeOH/NH$_4$OH 1000/100/8) to afford the title intermediate as a colourless oil (390 mg, 32% yield).

$^1$H NMR (CDCl$_3$) δ: 4.21 (br. t, J=3.8 Hz, 2H), 3.55 (m, 2H), 3.31 (m, 2H), 1.44 (s, 9H).

21.ii. (3R*,4S*)-3-hydroxy-4-(6-methoxy-quinazolin-4-yloxy)-pyrrolidine-1-carboxylic acid tert-butyl ester Starting from intermediate 21.i (386 mg, 3.90 mmol) and 4-chloro-6-methoxy-quinazoline (370 mg, 3.90 mmol) and using method C, the desired product was isolated as a yellow oil (346 mg, 50% yield).

MS (ESI, m/z): 362.2 [M+H$^+$].

21.iii. (3R*,4S*)-4-(6-methoxy-quinazolin-4-yloxy)-pyrrolidin-3-ol

Starting from intermediate 21.ii and using method A, the desired intermediate was obtained as a yellow solid (101 mg, 40% yield).

MS (ESI, m/z): 262.3 [M+H$^+$].

21.iv. 6-{(R)-5-[(3R*,4S*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one Starting from intermediate 21.iii and the compound of Preparation B and using method B, the desired product was obtained as a light yellow foam (66 mg, 66% yield).

MS (ESI, m/z): 524.0 [M+H$^+$].

Example 22

6-{(R)-5-[(3R*,4R*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one

22.i. (3R*,4R*)-3,4-dihydroxy-pyrrolidine-1-carboxylic acid tert-butyl ester To a solution of (1R*,5S*)-6-oxa-3-aza-bicyclo[3.1.0]hexane-3-carboxylic acid tert-butyl ester (commercial, 1.63 g, 8.80 mmol) in dioxane (8 mL) was added 2M NaOH (30 mL) and the mixture was stirred at 95° C. for 24 h. The mixture was evaporated and extracted with EA (3×). The combined org. layers were washed with brine, dried over MgSO$_4$ and concentrated under reduced pressure. The crude product was triturated with EA, filtered, and washed with EA to afford the title intermediate as a yellow solid (243 mg, 14% yield).

$^1$H NMR (DMSO-d6) δ: 5.09 (s, 2H), 3.84 (s, 2H), 3.31 (m, 2H), 3.09 (m, 2H), 1.37 (s, 9H).

22.ii. (3R*,4R*)-3-hydroxy-4-(6-methoxy-quinazolin-4-yloxy)-pyrrolidine-1-carboxylic acid tert-butyl ester Starting from intermediate 22.i (240 mg, 1.18 mmol) and 4-chloro-6-methoxy-quinazoline (230 mg, 1.18 mmol) and using method C, the desired product was obtained as a yellow oil (189 mg, 44% yield).

MS (ESI, m/z): 362.2 [M+H$^+$].

22.iii. (3R*,4R*)-4-(6-methoxy-quinazolin-4-yloxy)-pyrrolidin-3-ol

Starting from intermediate 22.i and using method A, the desired intermediate was obtained as a yellow foam (74 mg, 54% yield).

MS (ESI, m/z): 262.4 [M+H$^+$].

22.iv. 6-{(R)-5-[(3R*,4R*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one Starting from intermediate 22.iii and the compound of Preparation B and using method B, the desired product was obtained as a light yellow foam (14 mg, 19% yield).

MS (ESI, m/z): 524.2 [M+H$^+$].

Example 23

6-{(R)-5-[3-(3-fluoro-6-methoxy-[1,5]naphthyridin-4-ylamino)-azetidin-1-ylmethyl]-2-oxo-oxazolidin-3-yl}-4H-benzo[1,4]oxazin-3-one

23.i. {1-[(R)-2-oxo-3-(3-oxo-3,4-dihydro-2H-benzo[1,4]oxazin-6-yl)-oxazolidin-5-ylmethyl]-azetidin-3-yl}-carbamic acid benzyl ester Starting with the compound of preparation D and (3-azetidinylmethyl)-carbamic acid phenylmethyl ester (commercially available, CAS 914348-04-2) and using method B, the title intermediate was isolated as a colourless foam (272 mg, 46% yield).

MS (ESI, m/z): 453.1 [M+H$^+$].

23.ii. 6-[(R)-5-(3-amino-azetidin-1-ylmethyl)-2-oxo-oxazolidin-3-yl]-4H-benzo[1,4]oxazin-3-one Starting with intermediate 23.i and using method G, the title intermediate was isolated as a colourless foam (43 mg, 76% yield).

MS (ESI, m/z): 319.1 [M+H$^+$].

23.iii. 6-{(R)-5-[3-(3-fluoro-6-methoxy-[1,5]naphthyridin-4-ylamino)-azetidin-1-ylmethyl]-2-oxo-oxazolidin-3-yl}-4H-benzo[1,4]oxazin-3-one Starting with intermediate 23.ii and 8-bromo-7-fluoro-2-methoxy-[1,5]naphthyridine (commercially available, CAS 724788-70-9) and using method F, the title compound was isolated as a colourless solid (24 mg, 48% yield).

¹H NMR (CDCl₃) δ: 9.22 (s, 1H), 8.37 (d, J=4.4 Hz, 1H), 8.06 (d, J=9.1 Hz, 1H), 7.45 (d, J=2.3 Hz, 1H), 7.00 (d, J=9.1 Hz, 1H), 6.88 (m, 1H), 6.74 (dd, J=8.8, 2.6 Hz, 1H), 6.03 (dd, J=7.0, 2.1 Hz, 1H), 4.68 (m, 2H), 4.55 (s, 2H), 3.91 (m, 7H), 3.28 (t, J=6.7 Hz, 2H), 2.89 (m, 2H).
MS (ESI, m/z): 495.1 [M+H⁺].

Example 24

6-{(R)-5-[3-(6-methoxy-[1,5]naphthyridin-4-ylamino)-azetidin-1-ylmethyl]-2-oxo-oxazolidin-3-yl}-4H-benzo[1,4]oxazin-3-one In analogy to Example 23, step 23.iii, starting from 8-bromo-2-methoxy-1,5-naphthyridine (commercially available; CAS 881658-92-0) and intermediate 23.ii, the title compound was isolated as a colourless solid (14 mg, 26% yield).
¹H NMR (CDCl₃) δ: 9.36 (s, 1H), 8.38 (d, J=5.3 Hz, 1H), 8.12 (d, J=9.1 Hz, 1H), 7.50 (d, J=2.6 Hz, 1H), 7.05 (d, J=9.1 Hz, 1H), 6.88 (m, 1H), 6.71 (dd, J=8.8, 2.6 Hz, 1H), 6.36 (m, 2H), 4.69 (m, 1H), 4.54 (s, 2H), 4.30 (m, 1H), 4.00 (m, 6H), 3.85 (dd, J=8.5, 6.4 Hz, 1H), 3.29 (t, J=6.7 Hz, 2H), 2.97 (m, 1H), 2.85 (m, 1H).
MS (ESI, m/z): 477.0 [M+H⁺].

Example 25

6-{(R)-5-[3-(6-methoxy-quinolin-4-ylamino)-azetidin-1-ylmethyl]-2-oxo-oxazolidin-3-yl}-4H-benzo[1,4]oxazin-3-one In analogy to Example 23, step 23.iii, starting from 4-bromo-6-methoxyquinoline (commercially available; CAS 42881-66-3) and intermediate 23.ii, the title compound was isolated as a colourless solid (16 mg, 30% yield).
MS (ESI, m/z): 476.0 [M+H⁺].

Example 26

6-((R)-5-{3-[(3-fluoro-6-methoxy-[1,5]naphthyridin-4-ylmethyl)-amino]-azetidin-1-ylmethyl}-2-oxo-oxazolidin-3-yl)-4H-benzo[1,4]oxazin-3-one Starting with intermediate 23.ii and 3-fluoro-6-methoxy-[1,5]naphthyridine-4-carbaldehyde (prepared according to WO 2006/032466) and using method H, the title compound was isolated as a colourless solid (14 mg, 77% yield).
MS (ESI, m/z): 509.0 [M+H⁺].

Example 27

6-((R)-5-{3-[(6-methoxy-[1,5]naphthyridin-4-ylmethyl)-amino]-azetidin-1-ylmethyl}-2-oxo-oxazolidin-3-yl)-4H-benzo[1,4]oxazin-3-one Starting with intermediate 23.ii and 6-methoxy-[1,5]naphthyridine-4-carbaldehyde (prepared according to WO 2006/032466) and using method H, the title compound was isolated as a colourless solid (12 mg, 29% yield).
MS (ESI, m/z): 490.9 [M+H⁺].

Example 28

6-((R)-5-{3-[(3-fluoro-6-methoxy-quinolin-4-ylmethyl)-amino]-azetidin-1-ylmethyl}-2-oxo-oxazolidin-3-yl)-4H-benzo[1,4]oxazin-3-one Starting with intermediate 23.ii and 3-fluoro-6-methoxy-quinoline-4-carbaldehyde (prepared according to WO 2007/105154) and using method H, the title compound was isolated as a colourless solid (7 mg, 14% yield).
MS (ESI, m/z): 508.1 [M+H⁺].

Example 29

6-((R)-5-{3-[(6-methoxy-quinolin-4-ylmethyl)-amino]-azetidin-1-ylmethyl}-2-oxo-oxazolidin-3-yl)-4H-benzo[1,4]oxazin-3-one Starting with intermediate 23.ii and 6-methoxy-quinoline-4-carbaldehyde (commercially available, CAS 4363-94-4) and using method H, the title compound was isolated as a colourless solid (8 mg, 31% yield).
MS (ESI, m/z): 490.1 [M+H⁺].

Example 30

(R)-3-(2,3-dihydro-benzo[1,4]dioxin-6-yl)-5-[3-(6-methoxy-quinazolin-4-yloxymethyl)-azetidin-1-ylmethyl]-oxazolidin-2-one 30.i. 3-(6-methoxy-quinazolin-4-yloxymethyl)-azetidine-1-carboxylic acid tert-butyl ester Starting with 1-tert-butoxycarbonyl-3-hydroxymethyl-azetidine (commercially available; CAS 142253-56-3) and 4-chloro-6-methoxyquinazoline (commercially available; CAS 50424-28-7) and using method C, the title intermediate was isolated as a yellow oil (390 mg, 89% yield).
MS (ESI, m/z): 346.2 [M+H⁺].

30.ii. 4-(azetidin-3-ylmethoxy)-6-methoxy-quinazoline

Starting with intermediate 30.i and using method A, the title intermediate was isolated as a colourless oil (148 mg, 48% yield).
MS (ESI, m/z): 246.4 [M+H⁺].

30.iii. (R)-3-(2,3-dihydro-benzo[1,4]dioxin-6-yl)-5-[3-(6-methoxy-quinazolin-4-yloxymethyl)-azetidin-1-ylmethyl]-oxazolidin-2-one Starting with intermediate 30.ii and the compound of preparation E and using method B, the title compound was isolated as a colourless oil (10 mg, 2% yield).
MS (ESI, m/z): 479.3 [M+H⁺].

Example 31

6-{(R)-5-[4-(6-methoxy-quinazolin-4-yloxy)-piperidin-1-ylmethyl]-2-oxo-oxazolidin-3-yl}-4H-benzo[1,4]oxazin-3-one Starting with intermediate 20.ii and compound of preparation D and using method B, the title compound was isolated as a colourless oil (19 mg, 16% yield).
MS (ESI, m/z): 506.2 [M+H⁺].

Example 32

N-{(3R*,4R*)-4-(6-methoxy-quinazolin-4-yloxy)-1-[(R)-2-oxo-3-(3-oxo-3,4-dihydro-2H-benzo[1,4]thiazin-6-yl)-oxazolidin-5-ylmethyl]-pyrrolidin-3-yl}-acetamide To a solution of the compound of Example 18 (4 mg, 0.008 mmol) in DCM (1 mL) was added 1-acetylimidazole (1.1 eq.) and DIPEA (1.2 eq.). After stirring at rt for one day, 1-acetylimidazole (1.1 eq.) and DIPEA (1.2 eq.) were added and stirring was continued at rt for 4 days. The colourless solution was concentrated under reduced pressure and purified by CC (DCM/MeOH/NH$_4$OH 1000-50-4) to afford the title compound as a colourless solid (4 mg, 93% yield).
MS (ESI, m/z): 565.3 [M+H$^+$].

Example 33

(R)-3-(6,7-dihydro-[1,4]dioxino[2,3-c]pyridazin-3-yl)-5-[(RS)-3-(6-methoxy-quinazolin-4-yloxy)-pyrrolidin-1-ylmethyl]-oxazolidin-2-one 33.i. (RS)-3-(6-methoxy-quinazolin-4-yloxy)-pyrrolidine-1-carboxylic acid tert-butyl ester The title intermediate was prepared in analogy to Example 2, step 2.i, starting from (RS)-3-hydroxy-pyrrolidine-1-carboxylic acid tert-butyl ester (commercially available, CAS 103057-44-9), and was isolated as a pale yellow oil (764 mg, 43% yield).
MS (ESI, m/z): 346.3 [M+H$^+$].

33.ii. 6-methoxy-4-((RS)-pyrrolidin-3-yloxy)-quinazoline

Starting from intermediate 33.i and using method A, the title intermediate was obtained as a pale yellow solid (560 mg, 100% yield).
MS (ESI, m/z): 246.5 [M+H$^+$].

33.iii. {(S)-2-hydroxy-3-[(RS)-3-(6-methoxy-quinazolin-4-yloxy)-pyrrolidin-1-yl]-propyl}-carbamic acid benzyl ester A solution of intermediate 33.ii (133 mg, 0.544 mmol) and [(2S)-oxiranylmethyl]-carbamic acid phenylmethyl ester (commercially available; CAS 247050-11-9, 1 eq.) in EtOH/H$_2$O 9:1 was stirred at 80° C. overnight. The mixture was concentrated under reduced pressure and purified by CC (DCM/MeOH/NH$_4$OH 1000/50/4) to afford the title intermediate as a yellow oil (89 mg, 36% yield).
MS (ESI, m/z): 453.1 [M+H$^+$].

33.iv. (S)-5-[(RS)-3-(6-methoxy-quinazolin-4-yloxy)-pyrrolidin-1-ylmethyl]-oxazolidin-2-one To a solution of intermediate 33.iii (89 mg, 0.20 mmol) in DMF (1 mL) was added NaH (55% in mineral oil, 9 mg, 1 eq.). The reaction mixture was stirred at rt for 2 h. Water was added and the mixture was extracted with EA (3×). The combined org. phases were washed with water and brine, dried over MgSO$_4$ and concentrated The residue was purified by CC (DCM/MeOH/NH$_4$OH 1000-50-4) to afford the title intermediate as a yellow oil (12 mg, 18% yield).
MS (ESI, m/z): 345.2 [M+H$^+$].

33.v. (R)-3-(6,7-dihydro-[1,4]dioxino[2,3-c]pyridazin-3-yl)-5-[(RS)-3-(6-methoxy-quinazolin-4-yloxy)-pyrrolidin-1-ylmethyl]-oxazolidin-2-one Starting with intermediate 33.iv and 3-chloro-6,7-dihydro-[1,4]dioxino[2,3-c]pyridazine (commercially available; CAS 943026-40-2) and using method F, the title compound was isolated as a pale yellow solid (3 mg, 21% yield).
MS (ESI, m/z): 481.1 [M+H$^+$].

Example 34

6-((R)-5-{3-[(3-methoxy-quinoxalin-5-ylmethyl)-amino]-azetidin-1-ylmethyl}-2-oxo-oxazolidin-3-yl)-4H-benzo[1,4]oxazin-3-one Starting with intermediate 23.ii and 3-methoxy-quinoxaline-5-carbaldehyde (prepared according to WO 2007/107965) and using method H, the title compound was isolated as a colourless solid (8 mg, 17% yield).
MS (ESI, m/z): 490.9 [M+H$^+$].

Example 35

6-{(R)-5-[4-(6-methoxy-[1,5]naphthyridin-4-ylamino)-piperidin-1-ylmethyl]-2-oxo-oxazolidin-3-yl}-4H-benzo[1,4]oxazin-3-one 35.i. {1-[(R)-2-oxo-3-(3-oxo-3,4-dihydro-2H-benzo[1,4]oxazin-6-yl)-oxazolidin-5-ylmethyl]-piperidin-4-yl}-carbamic acid tert-butyl ester Starting with the compound of preparation D and piperidin-4-yl-carbamic acid tert-butyl ester (commercially available, CAS 73874-95-0) and using method B, the title intermediate was isolated as a pale yellow solid (721 mg, 69% yield).
MS (ESI, m/z): 447.2 [M+H$^+$].

35.ii. 6-[(R)-5-(4-amino-piperidin-1-ylmethyl)-2-oxo-oxazolidin-3-yl]-4H-benzo[1,4]oxazin-3-one Starting with intermediate 35.i and using method A, the title intermediate was isolated as a colourless solid (362 mg, 65% yield).
MS (ESI, m/z): 347.1 [M+H$^+$].

35.iii. 6-{(R)-5-[4-(6-methoxy-[1,5]naphthyridin-4-ylamino)-piperidin-1-ylmethyl]-2-oxo-oxazolidin-3-yl}-4H-benzo[1,4]oxazin-3-one Starting with intermediate 35.ii and 8-bromo-2-methoxy-1,5-naphthyridine (commercially available) and using method F, the title compound was isolated as a pale yellow solid (36 mg, 7% yield).
MS (ESI, m/z): 505.4 [M+H$^+$].

Example 36

6-{(R)-5-[3-(6-methoxy-[1,5]naphthyridin-4-ylamino)-azetidin-1-ylmethyl]-2-oxo-oxazolidin-3-yl}-4H-benzo[1,4]thiazin-3-one 36.i. {1-[(R)-2-oxo-3-(3-oxo-3,4-dihydro-2H-benzo[1,4]thiazin-6-yl)-oxazolidin-5-ylmethyl]-azetidin-3-yl}-carbamic acid tert-butyl ester Starting with the compound of preparation B and azetidin-3-yl-carbamic acid tert-butyl ester (commercially available, CAS 91188-13-5) and using method B, the title intermediate was isolated as a yellow solid (2.04 g, 58% yield).
MS (ESI, m/z): 435.2 [M+H$^+$].

36.ii. 6-[(R)-5-(3-amino-azetidin-1-ylmethyl)-2-oxo-oxazolidin-3-yl]-4H-benzo[1,4]thiazin-3-one Starting with intermediate 36.i and using method A, the title intermediate was isolated as a pale yellow solid (1.22 g, 76% yield).
MS (ESI, m/z): 335.2 [M+H$^+$].

36.iii. 6-{(R)-5-[3-(6-methoxy-[1,5]naphthyridin-4-ylamino)-azetidin-1-ylmethyl]-2-oxo-oxazolidin-3-yl}-4H-benzo[1,4]thiazin-3-one Starting with intermediate 36.ii and 8-bromo-2-methoxy-[1,5]naphthyridine (commercially available) and using method F, the title compound was isolated as a pale yellow solid (612 mg, 85% yield).
$^1$H NMR (CDCl$_3$) δ: 8.74 (s, 1H), 8.39 (d, J=5.3 Hz, 1H), 8.10 (d, J=9.1 Hz, 1H), 7.47 (d, J=2.3 Hz, 1H), 7.25 (m, 1H), 7.06 (d, J=9.1 Hz, 1H), 6.89 (dd, J=8.8, 2.3 Hz, 1H), 6.38 (d, J=5.3 Hz, 1H), 6.31 (d, J=6.2 Hz, 1H), 4.71 (m, 1H), 4.31 (m, 1H), 4.02 (m, 6H), 3.89 (dd, J=8.5, 6.4 Hz, 1H), 3.40 (s, 2H), 3.28 (td, J=6.7, 3.2 Hz, 2H), 2.87 (m, 1H), 2.98 (m, 1H).
MS (ESI, m/z): 493.0 [M+H$^+$].

Example 37

6-{(R)-5-[3-(6-methoxy-quinolin-4-ylamino)-azetidin-1-ylmethyl]-2-oxo-oxazolidin-3-yl}-4H-benzo[1,4]thiazin-3-one Starting with intermediate 36.ii and 4-bromo-6-methoxy-quinoline (commercially available) and using method F, the title compound was isolated as a pale yellow solid (504 mg, 70% yield).
$^1$H NMR (CDCl$_3$) δ: 8.30 (d, J=5.3 Hz, 1H), 7.82 (d, J=9.4 Hz, 1H), 7.40 (d, J=2.3 Hz, 1H), 7.23 (m, 3H), 7.12 (d, J=2.6 Hz, 1H), 6.83 (dd, J=8.5, 2.3 Hz, 1H), 6.14 (d, J=5.3 Hz, 1H), 4.65 (m, 1H), 4.26 (m, 1H), 3.93 (m, 6H), 3.78 (dd, J=8.5, 6.4 Hz, 1H), 3.34 (m, 4H), 2.92 (m, 1H), 2.81 (m, 1H).
MS (ESI, m/z): 492.1 [M+H$^+$].

Example 38

4-{1-[(R)-2-oxo-3-(3-oxo-3,4-dihydro-2H-benzo[1,4]thiazin-6-yl)-oxazolidin-5-ylmethyl]-azetidin-3-ylamino}-quinoline-6-carbonitrile Starting with intermediate 36.ii and 4-bromo-quinoline-6-carbonitrile (commercially available, CAS 642477-82-5) and using method F and, the title compound was isolated as a pale yellow solid (225 mg, 77% yield).
MS (ESI, m/z): 487.5 [M+H$^+$].

Example 39

6-{(R)-5-[3-(6-fluoro-quinolin-4-ylamino)-azetidin-1-ylmethyl]-2-oxo-oxazolidin-3-yl}-4H-benzo[1,4]thiazin-3-one Starting with intermediate 36.ii and 4-bromo-6-fluoroquinoline (commercially available, CAS 661463-17-8) and using method F, the title compound was isolated as a pale yellow solid (93 mg, 32% yield).
MS (ESI, m/z): 480.3 [M+H$^+$].

Example 40

6-{(R)-5-[4-(6-methoxy-[1,5]naphthyridin-4-ylamino)-piperidin-1-ylmethyl]-2-oxo-oxazolidin-3-yl}-4H-benzo[1,4]thiazin-3-one 40.i. {1-[(R)-2-oxo-3-(3-oxo-3,4-dihydro-2H-benzo[1,4]thiazin-6-yl)-oxazolidin-5-ylmethyl]-piperidin-4-yl}-carbamic acid tert-butyl ester Starting with the compound of preparation B and piperidin-4-yl-carbamic acid tert-butyl ester (commercially available, CAS 73874-95-0) and using method B, the title intermediate was isolated as a beige solid (2.88 g, 49% yield).
MS (ESI, m/z): 463.2 [M+H$^+$].

40.ii. 6-[(R)-5-(4-amino-piperidin-1-ylmethyl)-2-oxo-oxazolidin-3-yl]-4H-benzo[1,4]thiazin-3-one Starting with intermediate 40.i and using method A, the title intermediate was isolated as a pale yellow foam (2.27 g, 100% yield).
MS (ESI, m/z): 363.1 [M+H$^+$].

40.iii. 6-{(R)-5-[4-(6-methoxy-[1,5]naphthyridin-4-ylamino)-piperidin-1-ylmethyl]-2-oxo-oxazolidin-3-yl}-4H-benzo[1,4]thiazin-3-one Starting with intermediate 40.ii and 8-bromo-2-methoxy-1,5-naphthyridine (commercially available) and using method F, the title compound was isolated as a pale yellow solid (355 mg, 41% yield).
MS (ESI, m/z): 521.4 [M+H$^+$].

Example 41

6-{(R)-5-[4-(6-methoxy-quinolin-4-ylamino)-piperidin-1-ylmethyl]-2-oxo-oxazolidin-3-yl}-4H-benzo[1,4]thiazin-3-one Starting with intermediate 40.ii and 4-bromo-6-methoxy-quinoline (commercially available) and using method F, the title compound was isolated as a pale yellow solid (102 mg, 12% yield).
MS (ESI, m/z): 520.5 [M+H$^+$].

Example 42

(R)-3-(2,3-dihydro-benzo[1,4]dioxin-6-yl)-5-[3-(6-methoxy-[1,5]naphthyridin-4-ylamino)-azetidin-1-ylmethyl]-oxazolidin-2-one 42.i. {1-[(R)-3-(2,3-dihydro-benzo[1,4]dioxin-6-yl)-2-oxo-oxazolidin-5-ylmethyl]-azetidin-3-yl}-carbamic acid tert-butyl ester A solution of the compound of preparation E (3.16 g, 8.7 mmol) and azetidin-3-yl-carbamic acid tert-butyl ester (1.5 g, 1 eq.) in dry DMSO (30 mL) was treated with DIPEA (1.8 mL) and heated at 80° C. for 72 h. The mixture was partitioned between EA and water and the org. phase was washed with water and brine, dried over MgSO$_4$ and concentrated. The residue was purified by FC (EA, EA/MeOH 9:1+1% NH$_4$OH) to give the desired intermediate as a beige solid (2.5 g, 71% yield).

¹H NMR (DMSO d6) δ: 7.27 (dd, J=7.0, 0.9 Hz, 1H), 7.09 (d, J=2.6 Hz, 1H), 6.94 (m, 1H), 6.83 (m, 1H), 4.57 (m, 1H), 4.21 (m, 1H), 4.00 (m, 4H), 3.66 (dd, J=8.8, 6.4 Hz, 1H), 3.50 (q, J=7.0 Hz, 2H), 2.91 (m, 2H), 2.65 (m, 2H), 1.35 (s, 9H).

42.ii. (R)-5-(3-amino-azetidin-1-ylmethyl)-3-(2,3-dihydro-benzo[1,4]dioxin-6-yl)-oxazolidin-2-one Starting with intermediate 42.i and using method A, the title intermediate was isolated as a colourless resin (1.33 g, 70% yield).
¹H NMR (DMSO d6) δ: 7.09 (d, J=2.6 Hz, 1H), 6.94 (m, 1H), 6.83 (m, 1H), 4.56 (m, 1H), 4.21 (m, 4H), 3.98 (t, J=8.8 Hz, 1H), 3.66 (dd, J=8.8, 6.7 Hz, 1H), 3.50 (m, 3H), 3.38 (d, J=6.7 Hz, 2H), 2.65 (m, 4H).

42.iii. (R)-3-(2,3-dihydro-benzo[1,4]dioxin-6-yl)-5-[3-(6-methoxy-[1,5]naphthyridin-4-ylamino)-azetidin-1-ylmethyl]-oxazolidin-2-one Starting with intermediate 42.ii (61 mg, 0.2 mmol) and 8-bromo-2-methoxy-1,5-naphthyridine (commercially available) and using method F, the title compound was isolated as a pale yellow solid (71 mg, 77% yield).
¹H NMR (CDCl₃) δ: 8.40 (d, J=5.3 Hz, 1H), 8.09 (d, J=9.1 Hz, 1H), 7.04 (m, 3H), 6.85 (d, J=8.8 Hz, 1H), 6.37 (d, J=5.3 Hz, 1H), 6.31 (d, J=6.4 Hz, 1H), 4.65 (m, 1H), 4.30 (m, 1H), 4.25 (s, 4H), 4.05 (s, 3H), 3.98 (m, 4H), 3.84 (dd, J=8.5, 6.7 Hz, 1H), 3.25 (t, J=6.7 Hz, 2H), 2.93 (m, 1H), 2.81 (m, 1H).
MS (ESI, m/z): 464.3 [M+H⁺].

Example 43

6-{(R)-5-[3-(6-fluoro-quinolin-4-ylamino)-azetidin-1-ylmethyl]-2-oxo-oxazolidin-3-yl}-4H-benzo[1,4]oxazin-3-one

43.i. 6-iodo-4-(4-methoxy-benzyl)-4H-benzo[1,4]oxazin-3-one

A solution of 6-iodo-4H-benzo[1,4]oxazin-3-one (6.88 g, 25 mmol) in DMF (50 mL) was treated with 4-methoxy-benzyl chloride (3.8 mL, 28 mmol, 1.1 eq.) and Cs₂CO₃ (9.78 g, 30 mmol, 1.2 eq.). The mixture was stirred at rt for 4 h and partitioned between EA (300 mL) and water (300 mL). The org. phase was washed with water (250 mL) and brine (200 mL), dried over MgSO₄ and concentrated. The residue was triturated with MeOH/Et₂O, the solid was filtered, washed with MeOH/Et₂O and dried under HV to give the title intermediate as a beige solid (7.8 g, 79% yield).
MS (ESI, m/z): 395.7 [M+H⁺].

43.ii. [1-(3-benzyloxycarbonylamino-2-hydroxy-propyl)-azetidin-3-yl]-carbamic acid tert-butyl ester A solution of (S)-oxiranylmethyl-carbamic acid benzyl ester (9.3 g, 45 mmol, 1.5 eq.) and azetidin-3-yl-carbamic acid tert-butyl ester (5.2 g, 30 mmol) in MeOH (60 mL) was treated with MgSO₄ (7.9 g) and heated at 40° C. for 3 h. The mixture was partitioned between EA/MeOH 19:1 (150 mL) and water (200 mL). The aq. layer was washed again with EA/MeOH 19:1 (150 mL) and the combined org. phases were washed with brine (150 mL), dried over MgSO₄ and concentrated. The residue was triturated in EA and filtered to give the title intermediate as a colourless solid (3.4 g, 30% yield).
MS (ESI, m/z): 380.2 [M+H⁺].

43.iii. [1-((S)-2-oxo-oxazolidin-5-ylmethyl)-azetidin-3-yl]-carbamic acid tert-butyl ester A solution of intermediate 43.ii (3.42 g, 9 mmol) in MeOH (100 mL) was treated with K₂CO₃ (1.35 g, 9.8 mmol, 1.09 eq.) and heated at 60° C. for 4 h. The mixture was concentrated in vacuo and purified by FC (EA/MeOH 19:1, 9:1+1% NH₄OH) to give the title intermediate as a colourless solid (2.3 g, 95% yield).
MS (ESI, m/z): 273.3 [M+H⁺].

43.iv. (1-{(R)-3-[4-(4-methoxy-benzyl)-3-oxo-3,4-dihydro-2H-benzo[1,4]oxazin-6-yl]-2-oxo-oxazolidin-5-ylmethyl}-azetidin-3-yl)-carbamic acid tert-butyl ester Intermediate 43.iii (1 g, 3.7 mmol), intermediate 43.i (1.46 g, 3.7 mmol, 1 eq.), CuI (141 mg, 0.74 mmol, 0.2 eq.), and K₂CO₃ (1.02 g, 7.4 mmol, 2 eq) were charged in an Ar-purged vial and 1,2-diaminocyclohexane (0.091 mL, 0.74 mmol, 0.2 eq.) and dioxane (22 mL) were added to the solids. The resulting mixture was purged with Ar and heated to 100° C. for 2 days. The mixture was partitioned between EA and water, the org. phase was washed with water and brine, dried over MgSO₄ and concentrated. The residue was purified by FC (EA, EA/MeOH 9:1+1% NH₄OH) to give the title intermediate as a brown foam (1.14 g, 58% yield).
MS (ESI, m/z): 539.2 [M+H⁺].

43.v. 6-[(R)-5-(3-amino-azetidin-1-ylmethyl)-2-oxo-oxazolidin-3-yl]-4-(4-methoxy-benzyl)-4H-benzo[1,4]oxazin-3-one Starting with intermediate 43.iv (1.13 g) and using method A, the title intermediate was isolated as a colourless resin (0.85 g, 92% yield).
MS (ESI, m/z): 439.5 [M+H⁺].

43.vi. 6-{(R)-5-[3-(6-fluoro-quinolin-4-ylamino)-azetidin-1-ylmethyl]-2-oxo-oxazolidin-3-yl}-4-(4-methoxy-benzyl)-4H-benzo[1,4]oxazin-3-one Starting with intermediate 43.v (429 mg, 1.9 mmol) and 4-bromo-6-fluoroquinoline (commercially available) and using method F, the title intermediate was isolated as a pale yellow solid (929 mg, 84% yield).
MS (ESI, m/z): 584.4 [M+H⁺].

43.vii. 6-{(R)-5-[3-(6-fluoro-quinolin-4-ylamino)-azetidin-1-ylmethyl]-2-oxo-oxazolidin-3-yl}-4H-benzo[1,4]oxazin-3-one A solution of intermediate 43.vi (905 mg, 1.55 mmol) in TFA (15 mL) in a sealed flask was heated at 80° C. overnight. The volatiles were removed under reduced pressure and the residue partitioned between DCM/MeOH 9:1 (130 mL) and NH₄OH (80 mL). The org. phase was washed with water (100 mL), dried over MgSO₄ and concentrated. The residue was crystallized from DCM/MeOH to give the title compound as a colourless solid (0.5 g, 70% yield).
¹H NMR (CDCl₃) δ: 8.40 (d, J=5.3 Hz, 1H), 8.09 (d, J=9.1 Hz, 1H), 7.04 (m, 3H), 6.85 (d, J=8.8 Hz, 1H), 6.37

(d, J=5.3 Hz, 1H), 6.31 (d, J=6.4 Hz, 1H), 4.66 (m, 1H), 4.30 (m, 1H), 4.25 (s, 4H), 4.05 (s, 3H), 3.98 (m, 3H), 3.84 (dd, J=8.5, 6.7 Hz, 1H), 3.25 (t, J=6.7 Hz, 2H), 2.93 (m, 1H), 2.81 (m, 1H).

MS (ESI, m/z): 464.3 [M+H$^+$].

Example 44

(R)-3-(2,3-dihydro-benzo[1,4]dioxin-6-yl)-5-[3-(6-methoxy-quinolin-4-yloxy)-azetidin-1-ylmethyl]-oxazolidin-2-one 44.i. 3-(2,3-dihydro-benzo[1,4]dioxin-6-yl)-5-(3-hydroxy-azetidin-1-ylmethyl)-oxazolidin-2-one The compound of preparation E (9 g, 25 mmol) and 3-hydroxyazetidine hydrochloride (4.1 g, 1.5 eq.) were coupled using method B to give the title intermediate as a beige solid (1.3 g, 17% yield).

MS (ESI, m/z): 307.3 [M+H$^+$].

44.ii. (R)-3-(2,3-dihydro-benzo[1,4]dioxin-6-yl)-5-[3-(6-methoxy-quinolin-4-yloxy)-azetidin-1-ylmethyl]-oxazolidin-2-one DIAD (0.116 mL) was added dropwise to a solution of intermediate 44.i (0.15 g, 0.49 mmol), PPh$_3$ (0.141 g) and 6-methoxy-quinolin-4-ol (0.086 g) in THF (1 mL). The mixture was stirred at rt for 1.5 h, concentrated in vacuo and purified by FC (EA, EA/MeOH 9:1+1% NH$_4$OH) to give the title compound as a yellow oil (12 mg).

MS (ESI, m/z): 464.5 [M+H$^+$].

Pharmacological Properties of the Invention Compounds
In Vitro Assays
Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards: Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All Example compounds were tested against several Gram-positive and Gram-negative bacteria.

Typical antibacterial test results are given in the table hereafter (MIC in mg/l).

| Example No. | M. catarrhalis A894 |
|---|---|
| 1 | ≤0.031 |
| 2 | ≤0.031 |
| 3 | ≤0.031 |
| 4 | ≤0.031 |
| 5 | ≤0.031 |
| 6 | ≤0.031 |
| 7 | ≤0.031 |
| 8 | ≤0.031 |
| 9 | ≤0.031 |
| 10 | ≤0.031 |
| 11 | 0.125 |
| 12 | ≤0.031 |
| 13 | 0.5 |
| 14 | ≤0.031 |
| 15 | ≤0.031 |
| 16 | ≤0.031 |
| 17 | 0.25 |
| 18 | ≤0.031 |
| 19 | 0.063 |
| 20 | ≤0.031 |
| 21 | ≤0.031 |
| 22 | ≤0.031 |
| 23 | ≤0.031 |
| 24 | ≤0.031 |
| 25 | ≤0.031 |
| 26 | ≤0.031 |
| 27 | ≤0.031 |
| 28 | ≤0.031 |
| 29 | 0.063 |
| 30 | 0.063 |
| 31 | ≤0.031 |
| 32 | 0.25 |
| 33 | 0.25 |
| 34 | 0.063 |
| 35 | ≤0.031 |
| 36 | ≤0.031 |
| 37 | 0.125 |
| 38 | 0.125 |
| 39 | 0.063 |
| 40 | ≤0.031 |
| 41 | 0.5 |
| 42 | ≤0.031 |
| 43 | 0.25 |
| 44 | 8 |

The invention claimed is:

1. A compound of formula I wherein
one or two of U, V, W, and X represent N, the rest represent CH or, in the case of X, may also represent CR$^a$ wherein R$^a$ is fluorine;

R$^1$ represents alkoxy, halogen or cyano;

R$^2$ represents H, CH$_2$OH, CH$_2$N$_3$, CH$_2$NH$_2$, alkylcarbonylaminomethyl or triazol-1-ylmethyl;

R$^3$ represents H, or, when n is 1, R$^3$ may also represent OH, NH$_2$, NHCOR$^6$ or triazol-1-yl;

A represents CR$^4$;

K represents O, NH, OCH$_2$, NHCO, NHCH$_2$, CH$_2$NH, CH$_2$CH$_2$, CH=CH, CHOHCHOH or CHR$^5$;

R$^4$ represents H or together with R$^5$ forms a bond, or also R$^4$ can represent OH when K is not O, NH, OCH$_2$ or NHCO;

R⁵ represents OH or together with R⁴ forms a bond;
R⁶ represents alkyl;
m is 0 or 1 and n is 0 or 1; and
G represents the group

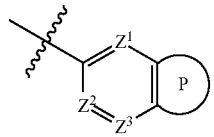

wherein Z¹ represents N, Z² represents CH, and Z³ represents CH; or
Z¹ represents CH, Z² represents N, and Z³ represents CH or N; or
Z¹ represents CH, Z² represents CH, and Z³ represents CH or N;
and the ring P is selected from the following:

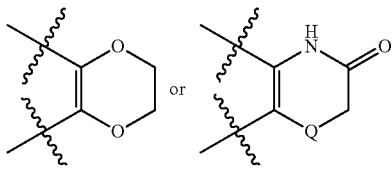

in which Q is O or S;
or a salt thereof.

2. The compound of formula I according to claim 1, wherein
R¹ represents alkoxy;
R³ represents H, or, when n is 1, R³ may also represent OH, NH₂ or triazol-1-yl;
K represents O, NH, OCH₂, NHCO, NHCH₂, CH₂CH₂, CH=CH, CHOHCHOH or CHR⁵, and
G represents the group

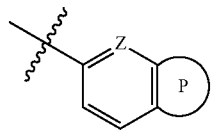

wherein Z is N or CH;
or a salt thereof.

3. The compound of claim 1, wherein R¹ is methoxy; or a salt thereof.

4. The compound of formula I according to claim 1, wherein
U and V each represent N and W and X each represent CH,
U and V each represent CH and W and X each represent N, or
U and W each represent N and V and X each represent CH;
or a salt thereof.

5. The compound of formula I according to claim 1 wherein m and n are each 0;
or a salt thereof.

6. The compound of formula I according to claim 1 wherein m is 1 and n is 0;
or a salt thereof.

7. The compound of formula I according to claim 1 wherein G is 3-oxo-3,4-dihydro-2H-benzo[1,4]thiazine-6-yl;
or a salt thereof.

8. The compound of formula I according to claim 1 wherein the compound is:
6-{(R)-5-[3-(6-methoxy-[1,5]naphthyridin-4-yloxy)-azetidin-1-ylmethyl]-2-oxo-oxazolidin-3-yl}-4H-benzo[1,4]thiazin-3-one;
6-{(R)-5-[(R)-3-(6-methoxy-quinazolin-4-yloxy)-pyrrolidin-1-ylmethyl]-2-oxo-oxazolidin-3-yl}-4H-benzo[1,4]thiazin-3-one;
6-{(R)-5-[(S)-3-(6-methoxy-quinazolin-4-yloxy)-pyrrolidin-1-ylmethyl]-2-oxo-oxazolidin-3-yl}-4H-benzo[1,4]thiazin-3-one;
(R)-3-(2,3-dihydro-benzo[1,4]dioxin-6-yl)-5-[3-(6-methoxy-quinazolin-4-yloxy)-pyrrolidin-1-ylmethyl]-oxazolidin-2-one;
6-{(R)-5-[(2S,4S)-2-hydroxymethyl-4-(6-methoxy-quinazolin-4-yloxy)-pyrrolidin-1-ylmethyl]-2-oxo-oxazolidin-3-yl}-4H-benzo[1,4]thiazin-3-one;
6-{(R)-5-[(2S,4S)-2-azidomethyl-4-(6-methoxy-quinazolin-4-yloxy)-pyrrolidin-1-ylmethyl]-2-oxo-oxazolidin-3-yl}-4H-benzo[1,4]thiazin-3-one;
1-[(R)-2-oxo-3-(3-oxo-3,4-dihydro-2H-benzo[1,4]thiazin-6-yl)-oxazolidin-5-ylmethyl]-azetidine-3-carboxylic acid (6-methoxy-[1,5]naphthyridin-4-yl)-amide;
1-[(R)-2-oxo-3-(3-oxo-3,4-dihydro-2H-benzo[1,4]thiazin-6-yl)-oxazolidin-5-ylmethyl]-pyrrolidine-3-carboxylic acid (6-methoxy-[1,5]naphthyridin-4-yl)-amide;
6-((R)-5-{3-[(E)-2-(6-methoxy-[1,5]naphthyridin-4-yl)-vinyl]-pyrrolidin-1-ylmethy}-2-oxo-oxazolidin-3-yl)-4H-benzo[1,4]thiazin-3-one;
6-((R)-5-{3-[2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one;
6-((R)-5-{3-[(1R,2R)-1,2-dihydroxy-2-(6-methoxy-[1,5]naphthyridin-4-yl)-ethyl]-pyrrolidin-1-ylmethyl}-2-oxo-oxazolidin-3-yl)-4H-benzo[1,4]thiazin-3-one;
6-{(R)-5-[4-(3-methoxy-quinoxalin-5-ylmethylene)-piperidin-1-ylmethyl]-2-oxo-oxazolidin-3-yl}-4H-benzo[1,4]thiazin-3-one;
6-((R)-5-{4-hydroxy-4-[hydroxy-(3-methoxy-quinoxalin-5-yl)-methyl]-piperidin-1-ylmethyl}-2-oxo-oxazolidin-3-yl)-4H-benzo[1,4]thiazin-3-one;
6-((R)-5-{3-[(6-methoxy-[1,5]naphthyridin-4-ylamino)-methyl]-azetidin-1-ylmethyl}-2-oxo-oxazolidin-3-yl)-4H-benzo[1,4]thiazin-3-one;
6-{(R)-5-[(2S,4S)-2-aminomethyl-4-(6-methoxy-quinazolin-4-yloxy)-pyrrolidin-1-ylmethyl]-2-oxo-oxazolidin-3-yl}-4H-benzo[1,4]thiazin-3-one;
6-{(R)-5-[(3R*,4R*)-3-(6-methoxy-quinazolin-4-yloxy)-4-[1,2,3]triazol-1-yl-pyrrolidin-1-ylmethyl]-2-oxo-oxazolidin-3-yl}-4H-benzo[1,4]thiazin-3-one;
N-{(2S,4S)-4-(6-methoxy-quinazolin-4-yloxy)-1-[(R)-2-oxo-3-(3-oxo-3,4-dihydro-2H-benzo[1,4]thiazin-6-yl)-oxazolidin-5-ylmethyl]-pyrrolidin-2-ylmethyl}-acetamide;
6-{(R)-5-[(3R*,4R*)-3-amino-4-(6-methoxy-quinazolin-4-yloxy)-pyrrolidin-1-ylmethyl]-2-oxo-oxazolidin-3-yl}-4H-benzo[1,4]thiazin-3-one;
6-{(R)-5-[(2S,4S)-4-(6-methoxy-quinazolin-4-yloxy)-2-[1,2,3]triazol-1-ylmethyl-pyrrolidin-1-ylmethyl]-2-oxo-oxazolidin-3-yl}-4H-benzo[1,4]thiazin-3-one;

6-{(R)-5-[4-(6-methoxy-quinazolin-4-yloxy)-piperidin-1-ylmethyl]-2-oxo-oxazolidin-3-yl}-4H-benzo[1,4]thiazin-3-one;

6-{(R)-5-[(3R*,4S*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one; or 6-{(R)-5-[(3R*,4R*)-3-hydroxy-4-(6-methoxy-quinazolin-4-yloxy)-pyrrolidin-1-ylmethyl]-2-oxo-oxazolidin-3-yl}-4H-benzo[1,4]thiazin-3-one;

or a salt thereof.

9. The compound of formula I according to claim 1 wherein the compound is:

6-{(R)-5-[3-(3-fluoro-6-methoxy-[1,5]naphthyridin-4-ylamino)-azetidin-1-ylmethyl]-2-oxo-oxazolidin-3-yl}-4H-benzo[1,4]oxazin-3-one;

6-{(R)-5-[3-(6-methoxy-[1,5]naphthyridin-4-ylamino)-azetidin-1-ylmethyl]-2-oxo-oxazolidin-3-yl}-4H-benzo[1,4]oxazin-3-one;

6-{(R)-5-[3-(6-methoxy-quinolin-4-ylamino)-azetidin-1-ylmethyl]-2-oxo-oxazolidin-3-yl}-4H-benzo[1,4]oxazin-3-one;

6-((R)-5-{3-[(3-fluoro-6-methoxy-[1,5]naphthyridin-4-ylmethyl)-amino]-azetidin-1-ylmethyl}-2-oxo-oxazolidin-3-yl)-4H-benzo[1,4]oxazin-3-one;

6-((R)-5-{3-[(6-methoxy-[1,5]naphthyridin-4-ylmethyl)-amino]-azetidin-1-ylmethyl}-2-oxo-oxazolidin-3-yl)-4H-benzo[1,4]oxazin-3-one;

6-((R)-5-{3-[(3-fluoro-6-methoxy-quinolin-4-ylmethyl)-amino]-azetidin-1-ylmethyl}-2-oxo-oxazolidin-3-yl)-4H-benzo[1,4]oxazin-3-one;

6-((R)-5-{3-[(6-methoxy-quinolin-4-ylmethyl)-amino]-azetidin-1-ylmethyl}-2-oxo-oxazolidin-3-yl)-4H-benzo[1,4]oxazin-3-one;

(R)-3-(2,3-dihydro-benzo[1,4]dioxin-6-yl)-5-[3-(6-methoxy-quinazolin-4-yloxymethyl)-azetidin-1-ylmethyl]-oxazolidin-2-one;

6-{(R)-5-[4-(6-methoxy-quinazolin-4-yloxy)-piperidin-1-ylmethyl]-2-oxo-oxazolidin-3-yl}-4H-benzo[1,4]oxazin-3-one;

N-{(3R*,4R*)-4-(6-methoxy-quinazolin-4-yloxy)-1-[(R)-2-oxo-3-(3-oxo-3,4-dihydro-2H-benzo[1,4]thiazin-6-yl)-oxazolidin-5-ylmethyl]-pyrrolidin-3-yl}-acetamide;

(R)-3-(6,7-dihydro-[1,4]dioxino[2,3-c]pyridazin-3-yl)-5-[3-(6-methoxy-quinazolin-4-yloxy)-pyrrolidin-1-ylmethyl]-oxazolidin-2-one;

6-((R)-5-{3-[(3-methoxy-quinoxalin-5-ylmethyl)-amino]-azetidin-1-ylmethyl}-2-oxo-oxazolidin-3-yl)-4H-benzo[1,4]oxazin-3-one;

6-{(R)-5-[4-(6-methoxy-[1,5]naphthyridin-4-ylamino)-piperidin-1-ylmethyl]-2-oxo-oxazolidin-3-yl}-4H-benzo[1,4]oxazin-3-one;

6-{(R)-5-[3-(6-methoxy-[1,5]naphthyridin-4-ylamino)-azetidin-1-ylmethyl]-2-oxo-oxazolidin-3-yl}-4H-benzo[1,4]thiazin-3-one;

6-{(R)-5-[3-(6-methoxy-quinolin-4-ylamino)-azetidin-1-ylmethyl]-2-oxo-oxazolidin-3-yl}-4H-benzo[1,4]thiazin-3-one;

4-{1-[(R)-2-oxo-3-(3-oxo-3,4-dihydro-2H-benzo[1,4]thiazin-6-yl)-oxazolidin-5-ylmethyl]-azetidin-3-ylamino}-quinoline-6-carbonitrile;

6-{(R)-5-[3-(6-fluoro-quinolin-4-ylamino)-azetidin-1-ylmethyl]-2-oxo-oxazolidin-3-yl}-4H-benzo[1,4]thiazin-3-one;

6-{(R)-5-[4-(6-methoxy-[1,5]naphthyridin-4-ylamino)-piperidin-1-ylmethyl]-2-oxo-oxazolidin-3-yl}-4H-benzo[1,4]thiazin-3-one;

6-{(R)-5-[4-(6-methoxy-quinolin-4-ylamino)-piperidin-1-ylmethyl]-2-oxo-oxazolidin-3-yl}-4H-benzo[1,4]thiazin-3-one;

(R)-3-(2,3-dihydro-benzo[1,4]dioxin-6-yl)-5-[3-(6-methoxy-[1,5]naphthyridin-4-ylamino)-azetidin-1-ylmethyl]-oxazolidin-2-one;

6-{(R)-5-[3-(6-fluoro-quinolin-4-ylamino)-azetidin-1-ylmethyl]-2-oxo-oxazolidin-3-yl}-4H-benzo[1,4]oxazin-3-one; or (R)-3-(2,3-dihydro-benzo[1,4]dioxin-6-yl)-5-[3-(6-methoxy-quinolin-4-yloxy)-azetidin-1-ylmethyl]-oxazolidin-2-one;

or a salt thereof.

10. A pharmaceutical composition comprising as an active principal the compound of formula I according to claim 1 or a pharmaceutically acceptable salt thereof, and at least one therapeutically inert excipient.

11. A method of treating a bacterial infection comprising the administration of a therapeutically effective amount of the compound of claim 1 or a pharmaceutically acceptable salt thereof.

12. A method of treating a bacterial infection comprising the administration of a therapeutically effective amount of the composition of claim 10.

* * * * *